United States Patent
Ianchulev et al.

(10) Patent No.: US 12,318,328 B2
(45) Date of Patent: Jun. 3, 2025

(54) SYSTEM FOR SHAPING AND IMPLANTING BIOLOGIC INTRAOCULAR STENT FOR INCREASED AQUEOUS OUTFLOW AND LOWERING OF INTRAOCULAR PRESSURE

(71) Applicant: Iantrek, Inc., Harrison, NY (US)

(72) Inventors: Tsontcho Ianchulev, Harrison, NY (US); Daniel Nelsen, Harrison, NY (US); David Robson, Harrison, NY (US)

(73) Assignee: Iantrek, Inc., Harrison, NY (US)

( * ) Notice: Subject to any disclaimer, the term of this patent is extended or adjusted under 35 U.S.C. 154(b) by 341 days.

(21) Appl. No.: 17/325,785

(22) Filed: May 20, 2021

(65) Prior Publication Data

US 2021/0361484 A1  Nov. 25, 2021

Related U.S. Application Data

(60) Provisional application No. 63/163,623, filed on Mar. 19, 2021, provisional application No. 63/027,689, filed on May 20, 2020.

(51) Int. Cl.
*A61F 9/00* (2006.01)
*A61F 9/007* (2006.01)

(52) U.S. Cl.
CPC ...... *A61F 9/00781* (2013.01); *A61F 9/00754* (2013.01)

(58) Field of Classification Search
CPC ............. A61F 9/00781; A61F 9/00754; A61F 9/0017; A61M 2210/0612
See application file for complete search history.

(56) References Cited

U.S. PATENT DOCUMENTS

| | | |
|---|---|---|
| 4,154,239 A | 5/1979 | Turley |
| 4,288,066 A | 9/1981 | Treace |
| 5,300,079 A | 4/1994 | Niezink et al. |
| 5,342,370 A | 8/1994 | Simon et al. |
| 5,662,661 A | 9/1997 | Boudjema |
| 5,702,441 A | 12/1997 | Zhou |
| 5,868,697 A | 2/1999 | Richter et al. |
| 5,868,728 A | 2/1999 | Giungo et al. |
| 5,941,250 A | 8/1999 | Aramant et al. |
| 6,036,678 A | 3/2000 | Giungo |

(Continued)

FOREIGN PATENT DOCUMENTS

| | | |
|---|---|---|
| CN | 86102079 A | 11/1986 |
| CN | 2044479 U | 9/1989 |

(Continued)

OTHER PUBLICATIONS

U.S. Appl. No. 16/699,039, filed Nov. 28, 2019, US 20210022919 A1.

(Continued)

*Primary Examiner* — Rebecca E Eisenberg
*Assistant Examiner* — Kate Elizabeth Strachan
(74) *Attorney, Agent, or Firm* — Mintz Levin Cohn Ferris Glovsky and Popeo, P.C.

(57) ABSTRACT

Systems and methods for preparation of an implant and ab interno insertion of the implant into an eye of a patient including a tissue cartridge configured to receive and hold a patch of a material; a cutting device; and a delivery device. Related devices, systems, and methods are provided.

26 Claims, 28 Drawing Sheets

(56) References Cited

U.S. PATENT DOCUMENTS

| | | |
|---|---|---|
| 6,205,177 B1 | 3/2001 | Girod et al. |
| 7,207,965 B2 | 4/2007 | Simon |
| 7,291,125 B2 | 11/2007 | Coroneo |
| 7,815,592 B2 | 10/2010 | Coroneo |
| 7,850,638 B2 | 12/2010 | Theodore Coroneo |
| 7,909,789 B2 | 3/2011 | Badawi et al. |
| 8,128,588 B2 | 3/2012 | Coroneo |
| 8,167,939 B2 | 5/2012 | Silvestrini et al. |
| 8,172,899 B2 | 5/2012 | Silvestrini et al. |
| 8,262,726 B2 | 9/2012 | Silvestrini et al. |
| 8,337,393 B2 | 12/2012 | Silverstrini et al. |
| 8,353,856 B2 | 1/2013 | Baerveldt |
| 8,372,437 B2 | 2/2013 | Daniel |
| 8,377,122 B2 | 2/2013 | Silvestrini et al. |
| 8,444,588 B2 | 5/2013 | Yablonski |
| 8,444,589 B2 | 5/2013 | Silvestrini |
| 8,535,333 B2 | 9/2013 | de Juan, Jr. et al. |
| 8,574,294 B2 | 11/2013 | Silvestrini et al. |
| 8,617,139 B2 | 12/2013 | Silvestrini et al. |
| 8,672,870 B2 | 3/2014 | Silvestrini et al. |
| 8,721,656 B2 | 5/2014 | De Juan, Jr. et al. |
| 8,728,021 B2 | 5/2014 | Theodore Coroneo |
| 8,734,378 B2 | 5/2014 | De Juan, Jr. et al. |
| 8,758,289 B2 | 6/2014 | Theodore Coroneo |
| 8,758,290 B2 | 6/2014 | Horvath et al. |
| 8,771,218 B2 | 7/2014 | Coroneo |
| 8,801,649 B2 | 8/2014 | De Juan, Jr. et al. |
| 8,808,219 B2 | 8/2014 | Bergheim et al. |
| 8,814,819 B2 | 8/2014 | De Juan, Jr. et al. |
| 8,852,137 B2 | 10/2014 | Horvath et al. |
| 8,932,205 B2 | 1/2015 | Silvestrini et al. |
| 8,945,038 B2 | 2/2015 | Yablonski |
| 8,961,617 B2 | 2/2015 | Young |
| 8,974,511 B2 | 3/2015 | Horvath et al. |
| 9,155,656 B2 | 10/2015 | Schaller et al. |
| 9,173,774 B2 | 11/2015 | Yaron et al. |
| 9,192,516 B2 | 11/2015 | Horvath et al. |
| 9,216,107 B2 | 12/2015 | Silvestrini et al. |
| 9,241,832 B2 | 1/2016 | Schaller et al. |
| 9,351,873 B2 | 5/2016 | Coroneo |
| 9,398,977 B2 | 7/2016 | de Juan, Jr. et al. |
| 9,421,130 B2 | 8/2016 | de Juan, Jr. |
| 9,549,845 B2 | 1/2017 | de Juan, Jr. et al. |
| 9,554,940 B2 | 1/2017 | Haffner et al. |
| 9,554,941 B2 | 1/2017 | Silvestrini et al. |
| 9,585,789 B2 | 3/2017 | Silvestrini et al. |
| 9,592,151 B2 | 3/2017 | Rangel-Friedman et al. |
| 9,636,254 B2 | 5/2017 | Yu et al. |
| 9,763,828 B2 | 9/2017 | Silvestrini et al. |
| 9,788,999 B2 | 10/2017 | Schaller |
| 9,789,000 B2 | 10/2017 | de Juan, Jr. et al. |
| 9,877,866 B2 | 1/2018 | Horvath et al. |
| 9,907,697 B2 | 3/2018 | Schaller et al. |
| 9,962,290 B2 | 5/2018 | Burns et al. |
| 9,987,472 B2 | 6/2018 | Tu et al. |
| 10,085,633 B2 | 10/2018 | Schaller et al. |
| 10,154,924 B2 | 12/2018 | Clauson et al. |
| 10,159,600 B2 | 12/2018 | Horvath et al. |
| 10,188,551 B2 | 1/2019 | Rangel-Friedman et al. |
| 10,285,853 B2 | 5/2019 | Rangel-Friedman et al. |
| 10,406,030 B2 | 9/2019 | Badawi et al. |
| 10,531,983 B2 | 1/2020 | Silvestrini et al. |
| 10,617,558 B2 | 4/2020 | Schieber et al. |
| 10,695,218 B1 | 6/2020 | Ianchulev |
| 10,888,460 B2 * | 1/2021 | Sorensen ............ A61B 18/1482 |
| 10,905,591 B1 | 2/2021 | Ianchulev |
| 10,940,087 B2 | 3/2021 | Thorne et al. |
| 11,045,355 B2 | 6/2021 | Ianchulev |
| 11,376,040 B2 | 7/2022 | Kalina, Jr. et al. |
| 11,419,762 B2 | 8/2022 | Ianchulev |
| 11,426,307 B2 | 8/2022 | Jacob |
| 11,517,476 B2 | 12/2022 | Pinchuk |
| 2002/0133168 A1 | 9/2002 | Smedley et al. |
| 2002/0193886 A1 | 12/2002 | Claeson et al. |
| 2003/0139809 A1 | 7/2003 | Worst et al. |
| 2004/0167623 A1 | 8/2004 | Peyman |
| 2004/0254520 A1 | 12/2004 | Porteous et al. |
| 2007/0179455 A1 | 8/2007 | Geliebter et al. |
| 2007/0219564 A1 | 9/2007 | Rue et al. |
| 2008/0208176 A1 | 8/2008 | Loh |
| 2008/0221501 A1 | 9/2008 | Cote et al. |
| 2009/0143712 A1* | 6/2009 | Tu .................. A61M 27/00 604/8 |
| 2010/0125237 A1 | 5/2010 | Schocket |
| 2011/0112546 A1* | 5/2011 | Juan, Jr. ............ A61F 9/00781 606/108 |
| 2012/0035743 A1 | 2/2012 | Young et al. |
| 2014/0236066 A1 | 8/2014 | Horvath et al. |
| 2014/0379015 A1* | 12/2014 | Sorensen ....... A61B 17/320016 606/170 |
| 2015/0065940 A1 | 3/2015 | Rangel-Friedman et al. |
| 2015/0238687 A1* | 8/2015 | Novakovic ......... A61F 9/0017 604/502 |
| 2017/0095369 A1 | 4/2017 | Andino et al. |
| 2017/0258727 A1 | 9/2017 | Tseng et al. |
| 2018/0036173 A1 | 2/2018 | Olson et al. |
| 2019/0038399 A1* | 2/2019 | Muller ............... A61F 9/00836 |
| 2019/0336335 A1 | 11/2019 | de Juan, Jr. et al. |
| 2020/0390601 A1 | 12/2020 | Ianchulev |
| 2020/0390602 A1 | 12/2020 | Ianchulev |
| 2021/0022919 A1 | 1/2021 | Ianchulev |
| 2021/0196516 A1 | 7/2021 | Ianchulev |
| 2021/0290435 A1 | 9/2021 | Ianchulev |
| 2022/0001085 A1 | 1/2022 | Shi et al. |
| 2022/0395397 A1 | 12/2022 | Chu |
| 2023/0000680 A1 | 1/2023 | Ianchulev et al. |
| 2023/0009442 A1 | 1/2023 | Ianchulev |
| 2023/0101775 A1 | 3/2023 | Detry et al. |
| 2023/0248569 A1 | 8/2023 | Vandiest et al. |
| 2023/0255807 A1 | 8/2023 | Detry et al. |

FOREIGN PATENT DOCUMENTS

| | | |
|---|---|---|
| CN | 101099695 A | 1/2008 |
| CN | 102431830 A | 5/2012 |
| CN | 102481404 A | 5/2012 |
| CN | 104540472 A | 4/2015 |
| CN | 105236005 A | 1/2016 |
| CN | 105434103 A | 3/2016 |
| CN | 107847243 A | 3/2018 |
| CN | 109561987 A | 4/2019 |
| GB | 2551102 A | 12/2017 |
| JP | 2013-059677 A | 4/2013 |
| KR | 10-2114787 B1 | 5/2020 |
| WO | WO-2014/089548 A1 | 6/2014 |
| WO | PCT/US20/15935 | 1/2020 |
| WO | PCT/US20/42594 | 7/2020 |
| WO | PCT/US22/42856 | 9/2022 |
| WO | PCT/US22/43002 | 9/2022 |
| WO | PCT/US2023/80677 | 11/2023 |
| WO | PCT/US2024/29419 | 5/2024 |

OTHER PUBLICATIONS

U.S. Appl. No. 17/164,122, filed Feb. 1, 2021, US 20210290435 A1.

Regulatory Considerations for Human Cells, Tissues, and Cellular and Tissue-Based Products: Minimal Manipulation and Homologous Use. Guidance for Industry and Food and Drug Administration Staff. (Jul. 2020). 28 pages. Available at: www.fda.gov/regulatory-information/search-fda-guidance-documents/regulatory-considerations-human-cells-tissues-and-cellular-and-tissue-based-products-minimal. Web. Dec. 6, 2022.

"Preloaded Dsaek Tissue" Product sheet, Eversight Services, revised Sep. 23, 2019, 1 page. https://www.eversightvision.org/wp-content/uploads/2019/10/Preloaded_DSAEK_23Sept19.pdf (last accessed Nov. 11, 2019).

Einmahl et al. (2002). "Evaluation of a novel biomaterial in the suprachoroidal space of the rabbit eye" Invest Ophthalmol Vis Sci. 43:1533-1539.

Karlen et al. (Jan. 1999). "Deep sclerectomy with collagen implant: medium term results" Br. J. Ophthalmol, 83(1):6-11.

(56) References Cited

OTHER PUBLICATIONS

Krejci L. (1974). "Microdrainage of anterior chamber of eye glaucoma operation using hydron capillary drain." Acta Univ Carol Med Monogr.;(61):1-90.
Larrañeta, E. et al. (2018). "Synthesis and characterization of hyaluronic acid hydrogels crosslinked using a solvent-free process for potential biomedical applications." Carbohydrate Polymers, 181, 1194-1205. https://doi.org/10.1016/j.carbpol.2017.12.015.
Nesterov,AP et al. (1979). "Surgical stimulation of the uveoscleral outflow. Experimental studies on enucleated human eyes" Acta Opthalmol (Copenh) June; 57(3):409-17.
U.S. Appl. No. 16/777,648, filed Jan. 30, 2020, US 20200390601 A1.
U.S. Appl. No. 17/178,066, filed Feb. 17, 2021, US 20210196516 A1.
U.S. Appl. No. 17/865,059, filed Jul. 14, 2022, US 20230009442 A1.
U.S. Appl. No. 17/940,380, filed Sep. 8, 2022, US 20230000680 A1.
U.S. Appl. No. 17/941,307, filed Sep. 9, 2022, US 20230082713 A1.
U.S. Appl. No. 18/430,141, filed Feb. 1, 2024, US 20240164943 A1.
U.S. Appl. No. 18/651,341, filed Apr. 30, 2024, US 20240277524 A1.
Sun S.Y. et al. (2008). "Therapeutic experience of avoiding faulty formation of anterior chamber after glaucoma operation." International Journal of Ophthalmology, 8(4); 838-840. [English abstract].
Zhao, C. et al. (2004). "Clinical observation of different implants in non-penetrating trabecular surgery," Journal of Clinical Ophthalmology, 04 Aug. 5, 2004; 356-358. [English abstract].
Nesterov, AP et al. (1978). "Implantation of a scleral strip into the supraciliary space and cyclodialysis in glaucoma." Acta Ophthalmol (Copenh) 56(5):697-704.

\* cited by examiner

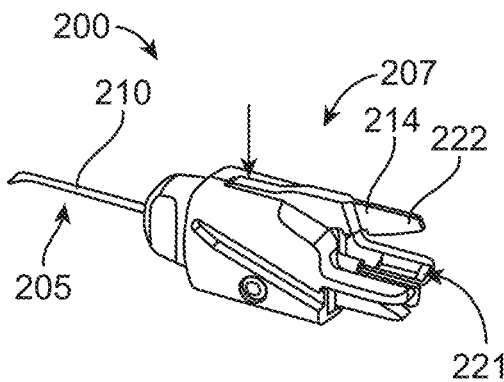
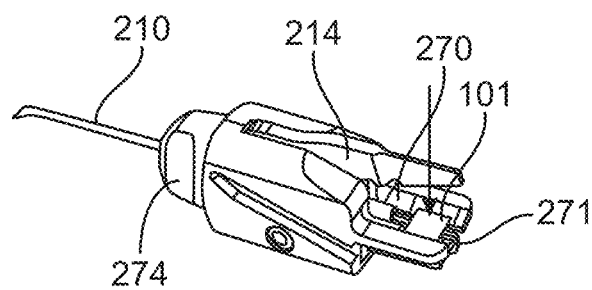
FIG. 7A
FIG. 7B
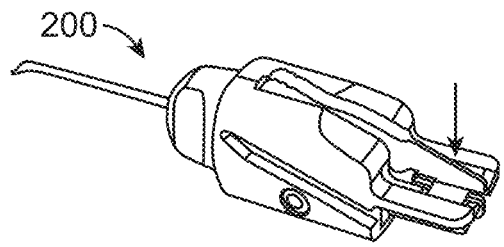
FIG. 7C
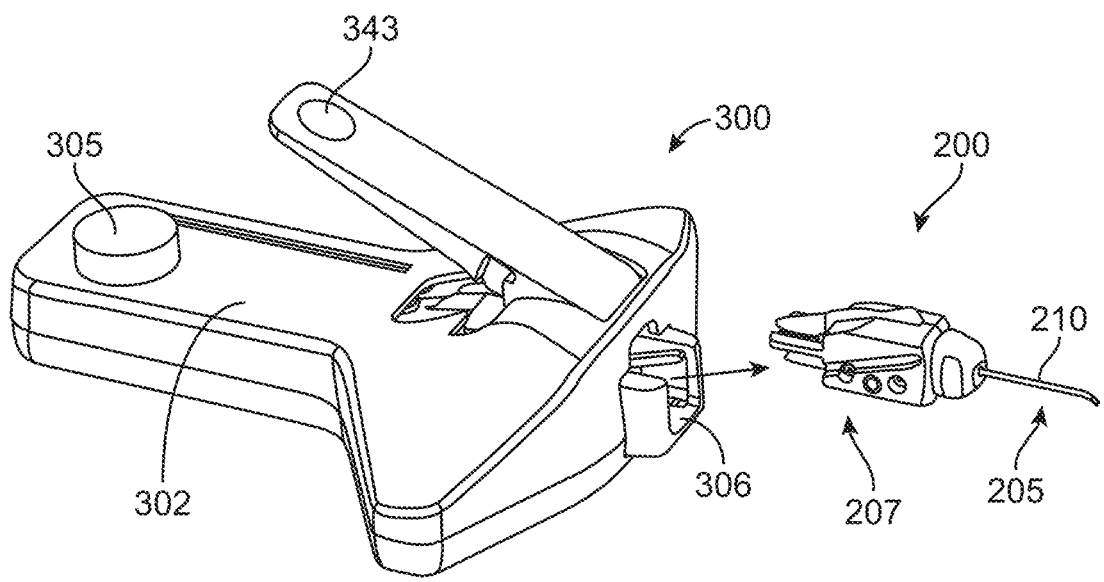
FIG. 8

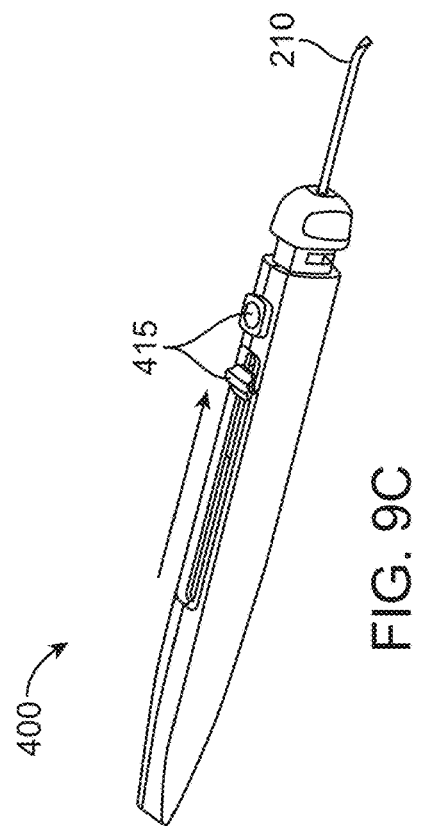
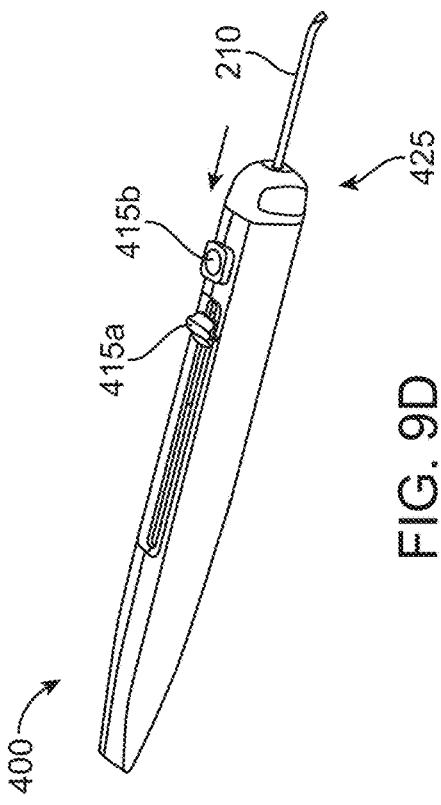
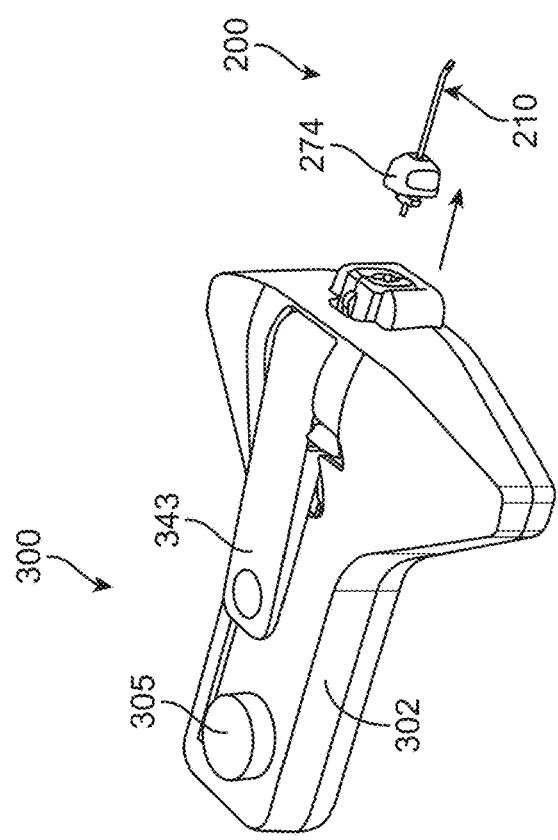
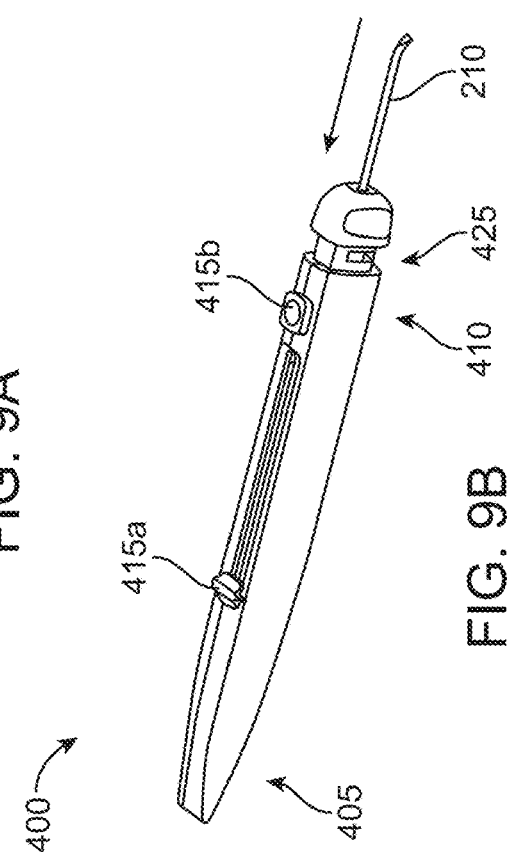
FIG. 9A
FIG. 9B
FIG. 9C
FIG. 9D

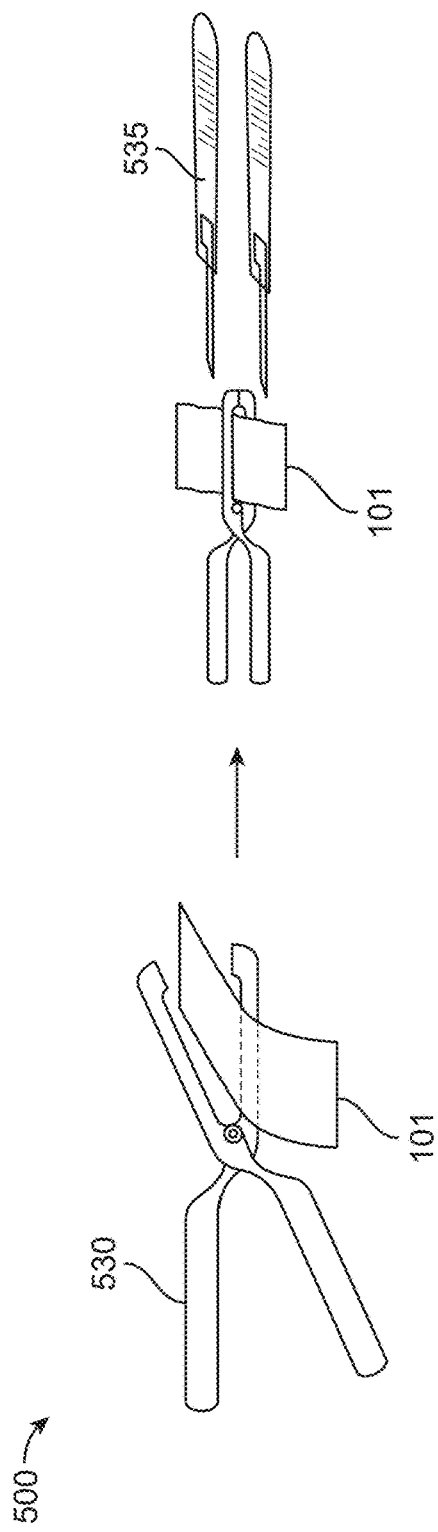
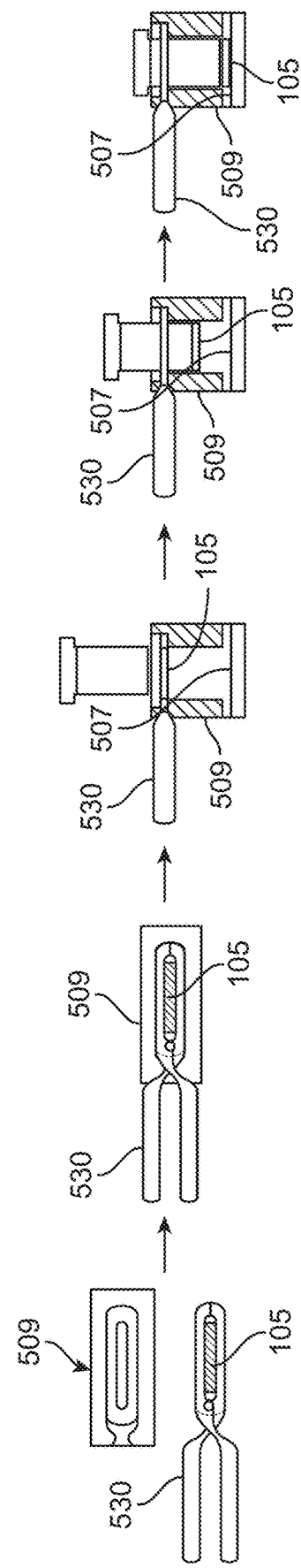
FIG. 14F-1
FIG. 14F-2

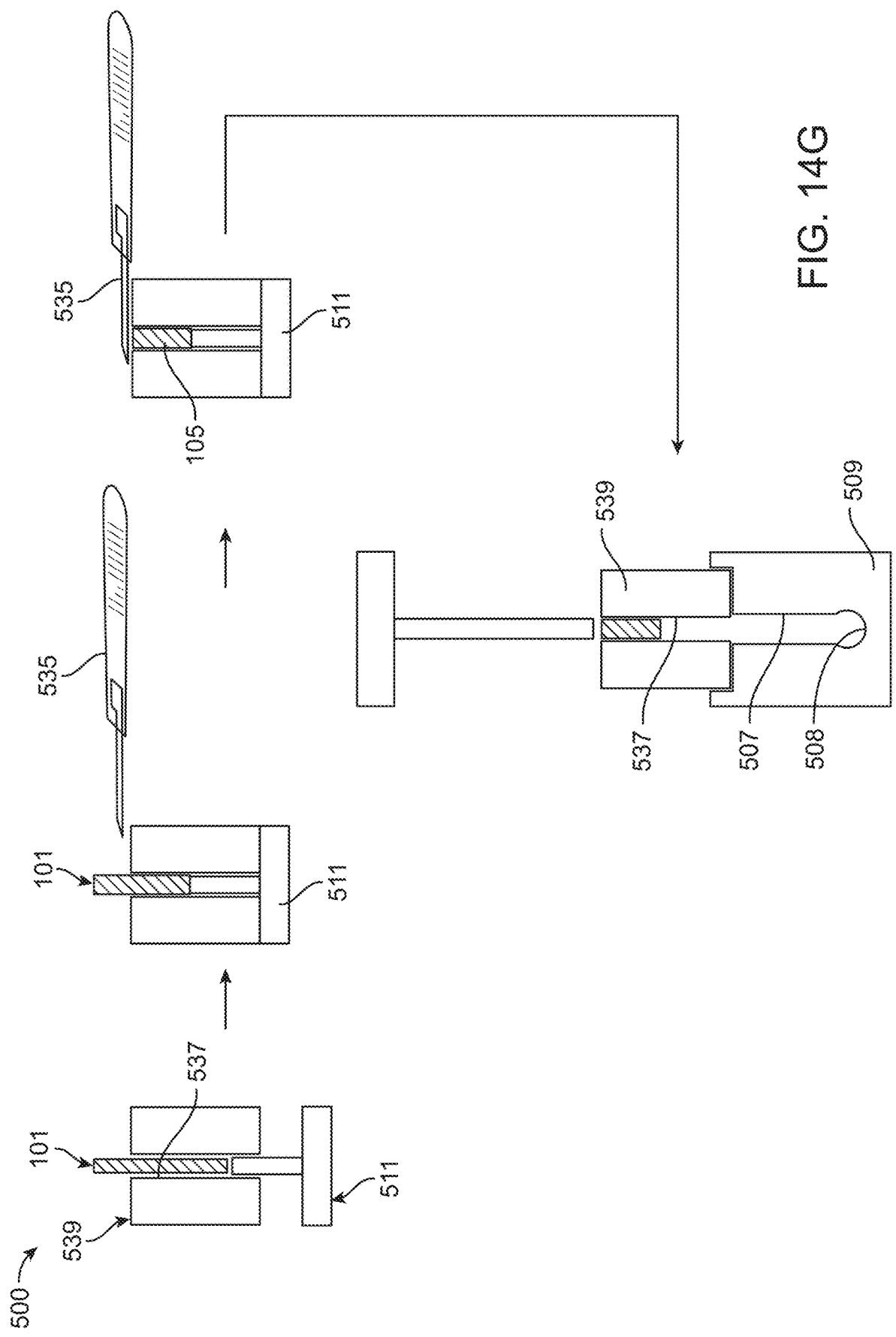

SYSTEM FOR SHAPING AND IMPLANTING BIOLOGIC INTRAOCULAR STENT FOR INCREASED AQUEOUS OUTFLOW AND LOWERING OF INTRAOCULAR PRESSURE

CROSS-REFERENCE TO RELATED APPLICATIONS

This application claims the benefit of priority under 35 U.S.C. § 119(e) to U.S. Provisional Patent Application Serial Nos. 63/027,689, filed May 20, 2020, and 63/163,623, filed Mar. 19, 2021. The disclosures of the applications are incorporated by reference in their entireties.

BACKGROUND

The mainstay of ophthalmic surgery for glaucoma is the enhancement of aqueous outflow from the eye. There are various approaches to such surgery, including: 1) ab externo trabeculectomy or shunting, which requires cutting the conjunctiva and the sclera to penetrate the eye and provide a trans-scleral outflow path; 2) ab interno trabecular or trans-scleral outflow stenting or shunting of aqueous with hardware-based implantable devices or with ablating, non-implantable cutters such as dual-blade and trabectome; and 3) ab interno supraciliary stenting using implantable non-biological hardware implants.

Current ab interno stenting devices and methods are based on non-biological hardware materials such as polyimide, polyethersulphone, titanium, poly styrene-blocks-isobutylene-block-styrene and others. There are significant drawbacks with such non-biological hardware-based implantable devices as such devices can lead to major erosion, fibrosis and ocular tissue damage such as endothelial cell loss.

In view of the foregoing, there is a need for improved devices and methods related to ophthalmic surgery for the treatment of glaucoma.

SUMMARY

In an aspect, described is a system for preparation of an implant and ab interno insertion of the implant into an eye of a patient. The system includes a tissue cartridge configured to receive and hold a patch of a material; a cutting device; and a delivery device.

The tissue cartridge can include a shaft extending from a distal end of the tissue cartridge. At least a distal end region of the shaft is sized and shaped for insertion into an anterior chamber of the eye. The shaft can include a lumen. The tissue cartridge can further include a base and a cover. The base can be configured to receive the patch and the cover configured to hold the patch fixed against the base. The cutting device can include a cutting member configured to cut the patch of a material positioned within the tissue cartridge. Cutting the patch of a material with the cutting member can form an implant from the patch. The implant can be configured for implantation into the eye of the patient. The delivery device can include an actuator configured to deploy the implant positioned within the cartridge through the lumen of the shaft into the eye.

In an interrelated implementation, described is a method of preparing an implant for implantation into, and of inserting said implant into, an eye of a patient. The method includes inserting a patch of a material into a tissue cartridge. The tissue cartridge includes a shaft extending from a distal end of the tissue cartridge. At least a distal end region of the shaft is sized and shaped for insertion into an anterior chamber of the eye. The shaft includes a lumen. The method further includes coupling the tissue cartridge with a cutting device. The cutting device has a cutting member configured to cut the patch of a material within the tissue cartridge. The method further includes cutting the patch with the cutting member to form the implant from the patch while the tissue cartridge is coupled with the cutting device; decoupling the tissue cartridge from the cutting device; coupling the tissue cartridge to a delivery device; inserting the distal end region of the shaft into the anterior chamber of the eye; positioning the distal end region adjacent eye tissue; and actuating the delivery device to deploy the implant from the cartridge through at least a portion of the lumen such that the implant engages the eye tissue. The method can further include delivering a viscous material through the shaft.

In an interrelated implementation, described is a system for preparation of an implant and ab interno insertion of the implant into an eye of a patient. The system includes a tissue cartridge configured to receive and hold a patch of a material; and a delivery device.

The tissue cartridge can include a shaft extending from a distal end of the tissue cartridge. At least a distal end region of the shaft can be sized and shaped for insertion into an anterior chamber of the eye. The shaft can include a lumen. The tissue cartridge can further include a base and a cover. The base can be configured to receive the patch and the cover configured to hold the patch fixed against the base. The system can further include a cutting device. The cutting device can include a cutting member configured to cut the patch of a material positioned within the tissue cartridge. Cutting the patch of a material with the cutting member can form an implant from the patch. The implant can be configured for implantation into the eye of the patient. The delivery device can include an actuator configured to deploy the implant positioned within at least a portion of the cartridge through the lumen of the shaft into the eye. The tissue cartridge can include a nose cone assembly having the distal end region of the tissue cartridge and the shaft. The nose cone assembly can be reversibly coupled to the tissue cartridge and reversibly coupled to the delivery device. The shaft of the tissue cartridge can be configured to deliver a viscous material.

In an interrelated implementation, described is a method preparing an implant for implantation into, and of inserting said implant into, an eye of a patient. The method includes inserting a patch of a material into a tissue cartridge. The tissue cartridge includes a shaft extending from a distal end of the tissue cartridge. At least a distal end region of the shaft is sized and shaped for insertion into an anterior chamber of the eye. The shaft includes a lumen. The method incudes coupling the tissue cartridge with a cutting device. The cutting device has a cutting member configured to cut the patch of a material within the tissue cartridge. The method includes cutting the patch with the cutting member to form the implant from the patch while the tissue cartridge is coupled with the cutting device; decoupling at least a portion of the tissue cartridge from the cutting device; coupling the at least a portion of the tissue cartridge to a delivery device; inserting the distal end region of the shaft into the anterior chamber of the eye; positioning the distal end region adjacent eye tissue; and actuating the delivery device to deploy the implant from the cartridge through at least a portion of the lumen such that the implant engages the eye tissue. The method can further include delivering a viscous material through the shaft.

In an interrelated implementation, described is a system for preparation of an implant from a patch of a material and ab interno insertion of the implant into an eye of a patient that includes a tissue cartridge having a nose cone and a distal shaft defining a lumen between the nose cone and a distal end region of the distal shaft; a cutting device configured to couple to the nose cone; and a delivery device configured to couple to the nose cone.

At least the distal end region of the distal shaft can be sized and shaped for insertion into an anterior chamber of the eye. The cutting device can include a base configured to receive the patch. The cutting device can include a cutting member configured to cut the patch of a material into the implant. The cutting device can further include a compacting tool configured to urge the implant into the lumen of the distal shaft. The delivery device can include an actuator configured to deploy the implant compacted within the lumen of the distal shaft into the eye.

In an interrelated implementation, described is a method of preparing an implant from a patch of a material for implantation into, and of inserting said implant into, an eye of a patient. The method includes coupling a tissue cartridge with a cutting device, the tissue cartridge having a shaft extending from a distal end of the tissue cartridge, at least a distal end region of the shaft sized and shaped for insertion into an anterior chamber of the eye. The shaft includes a lumen and the cutting device has a cutting member configured to cut the patch of a material. The method further includes cutting the patch with the cutting member to form the implant from the patch; compacting the implant within the lumen of the shaft; decoupling the tissue cartridge from the cutting device; coupling the tissue cartridge to a delivery device; inserting the distal end region of the shaft into the anterior chamber of the eye; positioning the distal end region adjacent eye tissue; and actuating the delivery device to deploy the implant from the lumen such that the implant engages the eye tissue. The method can further include delivering a viscous material through the shaft.

In an interrelated implementation, described is a system for preparation of an implant and ab interno insertion of the implant into an eye of a patient including a tissue cartridge; and a delivery device. The tissue cartridge can include a shaft extending from a distal end of the tissue cartridge, at least a distal end region of the shaft sized and shaped for insertion into an anterior chamber of the eye. The shaft can include a lumen. The system can further include a cutting device having a cutting member configured to cut the patch of a material. Cutting the patch of a material with the cutting member can form an implant from the patch that is configured for implantation into the eye of the patient. The delivery device can include an actuator configured to deploy the implant positioned within the shaft through the lumen of the shaft into the eye. The tissue cartridge can include a nose cone assembly having the distal end region of the tissue cartridge and the shaft. The nose cone assembly can be reversibly coupled to the tissue cartridge and reversibly coupled to the delivery device. The shaft of the tissue cartridge can be configured to deliver a viscous material.

In an interrelated implementation, described is a method of preparing an implant for implantation into, and of inserting said implant into, an eye of a patient including cutting a patch of a material with a cutting member of a cutting device to form an implant from the patch; compacting the implant within a lumen of a shaft extending from a distal end of a tissue cartridge; decoupling at least a portion of the tissue cartridge from the cutting device; coupling the at least a portion of the tissue cartridge to a delivery device; inserting a distal end region of the shaft into the anterior chamber of the eye; positioning the distal end region adjacent eye tissue; and actuating the delivery device to deploy the implant from the tissue cartridge through at least a portion of the lumen such that the implant engages the eye tissue. The method can further include delivering a viscous material through the shaft.

In an interrelated implementation, described is a method of treating an eye with minimally-modified biological tissue. The biological tissue can be scleral tissue. Minimally-modifying the scleral tissue can include compressing the scleral tissue from a first size into a second, smaller size within a distal shaft. The distal shaft can be sized and shaped to be inserted through a self-sealing incision in a cornea of the eye into the anterior chamber. The method can further include deploying the compressed scleral tissue from the distal shaft between tissue layers near the iridocorneal angle. The compressed scleral tissue deployed from the distal shaft can return towards the first size. The method can further include treating glaucoma with the compressed scleral tissue.

In some variations, one or more of the following can optionally be included in any feasible combination in the above methods, apparatus, devices, and systems. More details are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally, the figures are not to scale in absolute terms or comparatively, but are intended to be illustrative. Also, relative placement of features and elements may be modified for the purpose of illustrative clarity.

FIGS. 7A and 7B illustrate a tissue cartridge having a cover in a loading configuration;

FIG. 7C illustrates the tissue cartridge of FIGS. 7A-7B with the cover installed;

FIG. 8 illustrates an implementation of a cutting device and a tissue cartridge;

FIG. 9A illustrates an implementation of the cutting device having the tissue cartridge installed, the cutter in the cut configuration, and a nose cone of the tissue cartridge detached;

FIG. 9B illustrates an implementation of a delivery device having the nose cone of the tissue cartridge engaged and the pusher in the retracted configuration;

FIG. 9C illustrates the delivery device of FIG. 9B with the pusher advanced to the primed configuration;

FIG. 9D illustrates the delivery device of FIG. 9C with the nose cone retracted relative to the pusher;

FIGS. 14A-14H illustrate implementations of a cutting assembly for cutting and transferring a stent to a portion of the tissue cartridge;

Figure 1A:
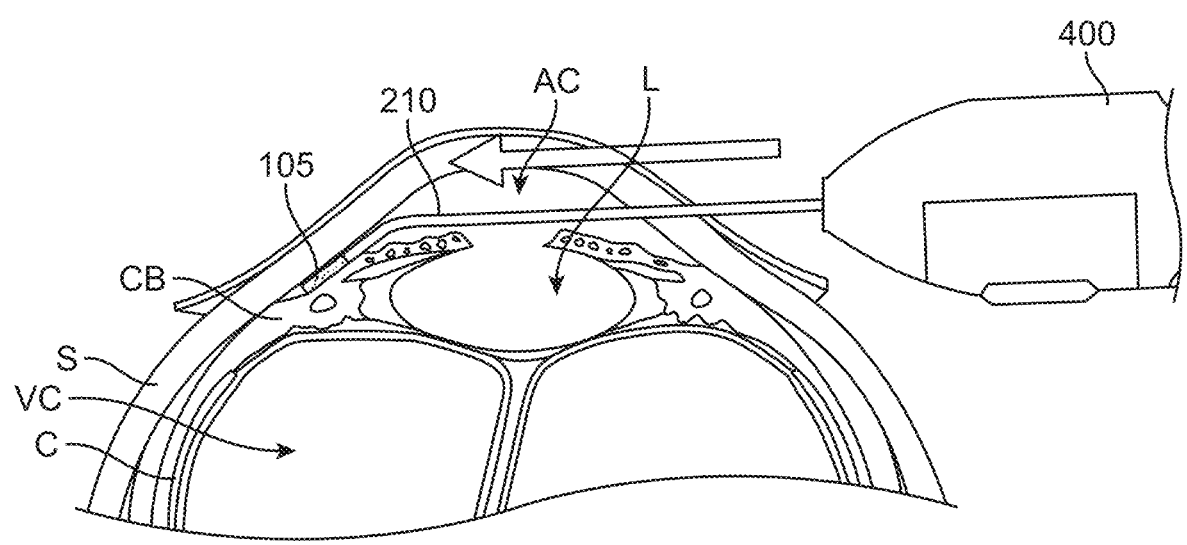
FIGS. 1A-1B are cross-sectional views of a human eye showing the anterior and vitreous chambers of the eye with a stent being positioned in the eye in an example location.

It should be appreciated that the drawings are for example only and are not meant to be to scale. It is to be understood that devices described herein may include features not necessarily depicted in each figure.

DETAILED DESCRIPTION

Disclosed are implants, systems, and methods for increasing aqueous outflow from the anterior chamber of an eye. As will be described in detail below, ab interno outflow stenting using biological, cell-based or tissue-based materials provides biocompatible aqueous outflow enhancement with improved tolerability and safety over conventional shunts. In an example implementation, a biologic tissue or biologically-derived material is harvested or generated in vitro and formed into an implant, also referred to herein as a stent, using a cutting device, also referred to herein as a trephining device or cutting tool. In an implementation, the stent is an elongated body or material that has an internal lumen to provide a pathway for drainage. In a preferred implementation, the stent is an elongated body or strip of tissue that does not have an internal lumen and is configured to maintain the cleft and provide supraciliary stenting. Lumen-based devices can be limited by the lumen acting as a tract for fibrotic occlusion. The stent formed from the tissue is then implanted into the eye via an ab interno delivery pathway to provide aqueous outflow from the anterior chamber. The stents described herein can be used as a phacoemulsification adjunct or stand-alone treatment to glaucoma as a micro-invasive glaucoma surgery (MIGS) treatment.

Use of the terms like stent, implant, shunt, bio-tissue, or tissue is not intended to be limiting to any one structure or material. The structure implanted can, but need not be a material that is absorbed substantially into the eye tissue after placement in the eye such that, once absorbed, a space may remain where the structure was previously located. The structure once implanted may also remain in place for an extended period and not substantially erode or absorb.

As will be described in more detail below, the stents described herein can be made from biologically-derived material that does not cause toxic or injurious effects once implanted in a patient.

The term "biologically-derived material" includes naturally-occurring biological materials and synthesized biological materials and combinations thereof that are suitable for implantation into the eye. Biologically-derived material includes a material that is a natural biostructure having a biological arrangement naturally found within a mammalian subject including organs or parts of organs formed of tissues, and tissues formed of materials grouped together according to structure and function. Biologically-derived material includes tissues such as corneal, scleral, or cartilaginous tissues. Tissues considered herein can include any of a variety of tissues including muscle, epithelial, connective, and nervous tissues. Biologically-derived material includes tissue harvested from a donor or the patient, organs, parts of organs, and tissues from a subject including a piece of tissue suitable for transplant including an autograft, allograft, and xenograft material. Biologically-derived material includes naturally-occurring biological material including any material naturally found in the body of a mammal. Biologically-derived material as used herein also includes material that is engineered to have a biological arrangement similar to a natural biostructure. For example, the material can be synthesized using in vitro techniques such as by seeding a three-dimensional scaffold or matrix with appropriate cells, engineered or 3D printing material to form a bio-construct suitable for implantation. Biologically-derived material as used herein also includes material that is cell-derived including stem cell(s)-derived material. In some implementations, the biologically-derived material includes an injectable hyaluronate hydrogels or viscomaterials such as GEL-ONE Cross-linked Hyaluronate (Zimmer).

In some implementations, the biostent may be an engineered or 3D printed material formed in the shape of a tube with a lumen extending from a proximal opening to a distal opening. The tube may also be printed to incorporate a plurality of openings throughout. For example, a wall of the printed material can be designed to have a plurality of openings such that a liquid within the lumen can seep or flow outward through the wall of the tube such that the tube is sufficiently porous to ensure drainage of aqueous from the eye. The tube may be printed to have a dimension that is modified at or near the time of delivery. For example, a 3D printed material may be engineered to have a first dimension that is convenient for manipulating manually. At or near the time of delivery, the 3D printed material may be cut to a size more suitable for implantation in the eye. Where a patch of material is described as being cut or trephined into a stent prior to implantation it should be appreciated that the patch of material can be a printed material having a particular 3-dimensional shape (e.g., including tubular) and is cut into a stent by cutting to a shorter, desired length. Thus, in certain implementations, the stents described herein need not be solid and can also incorporate a lumen.

The biologically-derived material, sometimes referred to herein as bio-tissue or bio-material, that is used to form the stent can vary and can be, for example, corneal tissue, scleral tissue, cartilaginous tissue, collagenous tissue, or other firm biologic tissue. The bio-tissue can be of hydrophilic or hydrophobic nature. The bio-tissue can include or be impregnated with one or more therapeutic agents for additional treatment of an eye disease process.

The bio-stent material can be used in combination with one or more therapeutic agents such that it can be used to additionally deliver the agent to the eye. In an implementation, the bio-tissue can be embedded with slow-release pellets or soaked in a therapeutic agent for slow-release delivery to the target tissue.

Non-biologic material includes synthetic materials prepared through artificial synthesis, processing, or manufacture that may be biologically compatible, but that are not cell-based or tissue-based. For example, non-biologic material includes polymers, copolymers, polymer blends, and plastics. Non-biologic material includes inorganic polymers such as silicone rubber, polysiloxanes, polysilanes, and organic polymers such as polyethylene, polypropylene, polyvinyls, polyimide, etc.

Regardless the source or type of biologically-derived material, the material can be cut or trephined into an elongated shape suitable for stenting and implantation in the eye. This cutting process of the tissue can be performed before the surgical implantation process or during the surgical implantation process. The stent(s) implanted in the eye may have a structure and/or permeability that allows for aqueous outflow from the anterior chamber when positioned within a cyclodialysis cleft.

The biologically-derived material can be minimally modified or minimally manipulated tissue for use in the eye. The minimally modified biologically-derived material does not involve the combination of the material with another article, except, for example, water, sterilizing, preserving, cryopreservatives, storage agent, and/or pharmaceutical or therapeutic agent(s), and the like. The minimally modified biologically-derived material does not have a systemic effect once implanted and is not dependent upon the metabolic activity of any living cells for its primary function. The biologically-derived material can be minimally manipulated during each step of the method of preparation and use so that the original relevant characteristics of the biologic tissue is maintained. The cut stent can be a structural tissue that physically supports or serves as a barrier or conduit, for example, by maintaining at least in part a ciliary cleft formed in the eye. The stent cut from the biologically-derived material can be minimally manipulated such as by compressing, compacting, folding, rolling, or other sort of temporary manipulation of the cut stent that once freed from the forces applying the compression or compaction allows for the material to return towards its original structure. Thus, the minimal manipulation can mechanically change the size or shape of the cut tissue temporarily while still maintaining the original relevant characteristics of the tissue relating to its utility for reconstruction, repair, or replacement once freed from that mechanical change. As an example, the biologically-derived material can be sclera that is cut into a shape that is oversized in relation to an inner diameter of a delivery tube through which the stent is implanted. The minimal manipulation of the cut stent can include temporarily compacting the scleral material into a lumen of the delivery shaft such that after implantation in the eye, the cut stent tends to return towards its original cut size. Although the biologically-derived material is described herein in the context of being cut into a stent like implant that can maintain a cleft for outflow of aqueous, other methods are considered herein. For example, the biologically-derived material can be compressed into a plug that is then implanted in a region of the eye for another purpose such as stenting, occlusion of traumatic ruptures, over-filtering bleb, posterior wall rupture, and other indications.

Figure 1B:
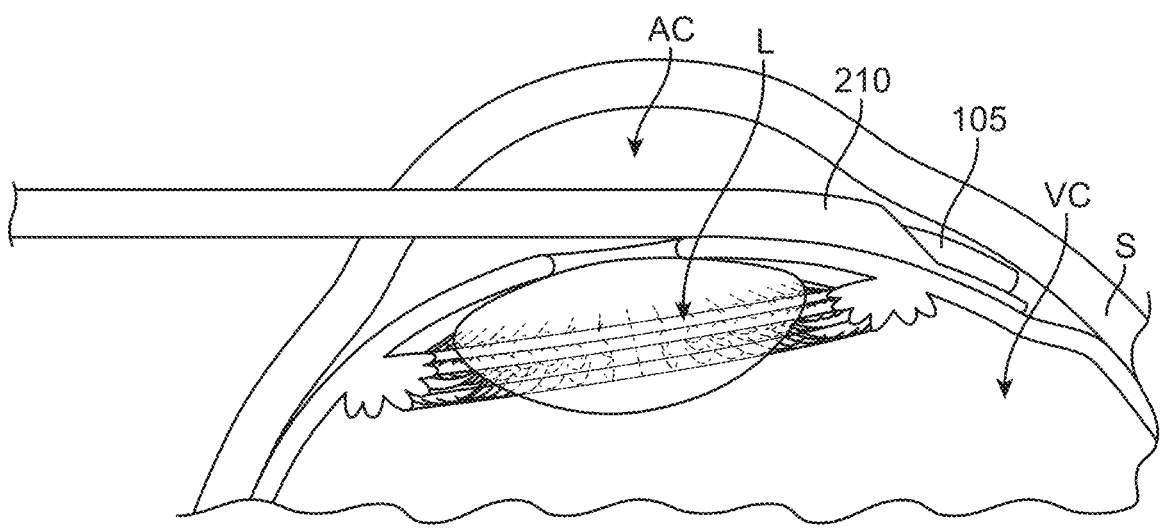

FIGS. 1A-1B are cross-sectional views of a human eye showing the anterior chamber AC and vitreous chamber VC of the eye. A stent 105 can be positioned inside the eye in an implanted location such that at least a first portion of the stent 105 is positioned in the anterior chamber AC and a second portion of the stent 105 is positioned within tissues such as within the supraciliary space and/or suprachoroidal space of the eye. The stent 105 is sized and shaped such that the stent 105 can be positioned in such a configuration. The stent 105 provides or otherwise serves as a passageway for the flow of aqueous humor away from the anterior chamber AC (e.g. to the supraciliary space and/or suprachoroidal space). In FIGS. 1A-1B, the stent 105 is represented schematically as an elongated body relative to a delivery shaft 210. It should be appreciated that the size and shape of the stent 105 can vary. Additionally, the size and shape of the stent 105 prior to insertion within the delivery shaft 210 can change upon insertion into the delivery shaft 210 and can change after deployment from the delivery shaft 210.

The stent 105 can be implanted ab interno, for example, through a clear corneal incision or a scleral incision. The stent can be implanted to create an opening or cleft for augmented outflow communication between the anterior chamber AC and the supraciliary space, the anterior chamber AC and the suprachoroidal space, the anterior chamber AC and Schlemm's Canal, or the anterior chamber AC and the sub-conjunctival space, or any other ocular compartment, tissue or interface where trans-scleral, sub-scleral, or suprascleral occlusion, stenting, and/or tissue reinforcing are clinically indicated. In a preferred implementation, the stent 105 is implanted such that a distal end is positioned within a supraciliary position and the proximal end is positioned within the anterior chamber AC to provide a supraciliary cleft. The distal end of the stent 105 can be positioned between other anatomical parts of the eye.

Conventional glaucoma stenting devices are typically formed of non-biological materials such as polyimide or other synthetic materials that can cause endothelial tissue damage leading to progressive, long-term, and irreversible corneal endothelial loss. The stent materials described herein can reduce and/or eliminate these risks of tissue damage while still providing enhanced aqueous humor outflow.

The stent 105 described herein can be formed of any of a variety of biologically-derived materials having a permeability and/or structure that allows for aqueous filtration therethrough. The stent 105 can be formed of a biologically-derived material that is harvested, engineered, grown, or otherwise manufactured. The biologically-derived stent material can be obtained or harvested from a patient or from donors. The biologically-derived stent material can be harvested before or during surgery. The biologically-derived stent material can be synthetic bio-tissue created using in vitro techniques. The biologically-derived material can be stem cell generated or bioengineered. The tissue can be generated via in situ cellular or non-cellular growth. In an example implementation, the tissue can be 3D printed during manufacture. The biologically-derived material can be minimally manipulated material and retain its original structural characteristic as a tissue.

The 3D printed tissue can be printed as a larger patch of material that is then cut at the time of surgery as described elsewhere herein. Alternatively, the 3D printed tissue can be printed to have the dimensions of the final implantable stent. In this implementation, the 3D printed material need not be cut before implantation, but can be implanted directly. For example, the 3D printed stent can be printed directly into a cartridge that is configured to operatively couple with the delivery device described herein, which is in turn used to deploy the 3D printed stent into the eye. The 3D printed stent can be generated using the 3D printing process described in Biofabrication, 2019; 11 (3).

In an example implementation, the stent 105 is made of a bio-tissue. The biologically-derived material can be corneal tissue and/or non-corneal tissue. The biologically-derived material may include corneal, scleral, collagenous or cartilaginous tissue. In an implementation, the biologically-derived stent material can be denuded corneal stromal tissue without epithelium and endothelium that is porous and has hydrophilic permeability to allow aqueous filtration. The biologically-derived material can be minimally manipulated sclera that retains its original structural characteristic as a tissue. The biologically-derived material of the stent 105 can, but need not be incorporated into the eye's inherent anatomy after placement in the eye. The stent can cause the surrounding tissue to form a pathway that remains open for an extended period, even after absorption of the stent. The biologically-derived stent material may not significantly absorb or be incorporated into the eye's anatomy such that the stent 105 remains implanted for an extended period of time or indefinitely, as needed.

In other implementations, the stent 105 material may be manufactured of a complex carbohydrate or a collagen that is non-inflammatory. The stent 105 may also be formed of a biodegradable or bioabsorbable material including biodegradable polymers including hydroxyaliphatic carboxylic acids, either homo- or copolymers, such as polylactic acid, polyglycolic acid, polylactic glycolic acid; polysaccharides such as cellulose or cellulose derivatives such as ethyl cellulose, cross-linked or uncross-linked sodium carboxymethyl cellulose, sodium carboxymethylcellulose starch, cellulose ethers, cellulose esters such as cellulose acetate, cellulose acetate phthallate, hydroxypropylmethyl cellulose phthallate and calcium alginate, polypropylene, polybutyrates, polycarbonate, acrylate polymers such as polymethacrylates, polyanhydrides, polyvalerates, polycaprolactones such as poly-c-caprolactone, polydimethylsiloxane, polyamides, polyvinylpyrollidone, polyvinylalcohol phthallate, waxes such as paraffin wax and white beeswax, natural oils, shellac, zein, or a mixture. The stent 105 may be formed of hyaluronate hydrogels or viscomaterials.

As mentioned, the biologically-derived stent material can have a permeability or porosity that allows for aqueous filtration for sufficient control or regulation of intraocular pressure. Permeable bio-tissues described herein (e.g. sclera, cornea, collagen, etc.) are preferred stent materials, however, any bio-tissue, even if impermeable, is considered herein as a potential stent material to serve as a structural spacer that keeps the cyclodialysis open. Preferably, the material of the stent can create a gap that allows fluid to flow. The gap created can run longitudinally along each side of the stent. If the material of the stent is permeable, more fluid can pass through the cyclodialysis than if the stent material is impermeable and the fluid is required to pass along the outside of the stent. Thus, the material considered herein need not be porous in order to provide the desired function, however, the function can be enhanced by the porosity of the material.

Generally, the biologically-derived stent material has some firmness and intraocular durability such that it can maintain outflow from the anterior chamber, however, is less stiff than conventional non-biologically-derived polyimide shunts used in the treatment of glaucoma (e.g. CYPASS, Alcon). The stent material may have a sufficient structure to serve as a spacer to prop open a sustained supraciliary outflow. The stent material can maintain its structural height or thickness once implanted within the cyclodialysis such that fluid flow through or around the stent is provided. In some implementations, the cut stent is minimally manipulated by compressing or compacting into a delivery shaft so that the size and/or shape of the cut stent is reduced from a first size into a second, smaller size within the shaft. The delivery shaft can be sized and shaped to be inserted through a cornea (such as a self-sealing incision in a cornea) into the anterior chamber and advanced towards the iridocorneal angle. The delivery shaft can deploy the compacted stent between tissue layers near the angle. Once the compacted stent is deployed from the delivery shaft it can begin to return towards its original shape and/or size. The cut stent, once implanted, can take on a shape and/or size that is smaller from its original shape and/or size or that is the same as its original shape and/or size. The minimally-modified biological tissue can be used to treat glaucoma. Biologically-derived stent material provides advantages in terms of biocompatibility, anatomic conformity, and aqueous permeability compared to conventional non-biological materials such as polyimide. Biologically-derived stent material can provide better conformability and compliance to the scleral wall and can be less likely to cause endothelial and scleral erosion/loss over time and with chronic eye rubbing and blinking.

Typically, allograft tissue for implantation into the eye is handled delicately so as not to modify it from its original state. The cut stents described herein need not be handled so delicately and instead can be minimally-modified by compressing or compacting or otherwise wedging into a smaller space for ab-interno delivery into the eye for intraocular stenting, occlusion, reinforcement through a corneal or scleral incision or puncture (less than about 3.5 mm).

In an implementation, the material used to form the stent is provided as an uncut patch of material configured to be manually loaded within a cartridge 200. The uncut patch of material can also be cut by a cutting assembly that is independent of a cartridge 200 and then transferred into a region of a cartridge 200. As will be discussed in greater detail below, the cutting can be done at the time of surgery or prior to surgery. In certain implementations, the stent is formed by 3D printing and can be printed into a desired final dimension for the stent or can be printed as a patch of material that is then cut at the time of or prior to surgery. The cutting achieved by the devices described herein can provide thin strips of material that can be implanted in the eye to provide regulation of aqueous outflow. The process of cutting or trephining can position the cut implant within a conduit or lumen of the cartridge such that the cut implant held within the cartridge may be subsequently delivered from the delivery device without needing to remove or transfer the cut implant from the cartridge. Alternatively, the cutting can be performed independently of transferring the cut implant into a delivery device. The cutting and transferring of the cut implant into a delivery device can be independent steps performed by independent tools or assemblies. For example, the system can incorporate a first device that is used for cutting the patch of material into a cut implant, a second device used to transfer the cut implant into a delivery device, and a third device used to deploy the cut implant from the delivery device into the eye. It should be appreciated that the cutting, transferring, and deploying can be integrated into a single device or one or more can be independent devices used in conjunction with one another to transition a patch of material into a cut implant for deployment in an eye. In a preferred embodiment, the cutting and transferring of the cut implant are integrated into a first device and the deployment of the cut implant in an eye is in a second device.

The term "patch of material" as used herein refers to a piece of biologically-derived material having a size along at least one dimension that is greater than a size of the stent cut from the patch of material and implanted in the subject. In some implementations, the patch of material can have a generally square shape and the stent cut or trephined from the patch of material can have a generally rectangular shape. For example, the patch of material can be about 7 mm wide×7 mm long×0.55 mm thick and the stent cut from the patch of material can be 0.3-1.0 mm wide×7 mm long×0.55 mm thick. The dimensions of the patch of material and the cut stent can vary. The patch of material prior to cutting can be between about 5 mm to about 10 mm wide, between about 5 mm up to about 10 mm long, and between about 0.25 mm to about 2 mm thick. The stent cut from the patch of material can be between about 0.3 mm up to about 2 mm wide, preferably between 0.7 mm to 1.0 mm wide. The stent cut from the patch of material can be between about 5 mm up to about 10 mm long. The stent cut from the patch of material can be between 0.25 mm to about 2 mm thick. The patch of material and the cut stent can each have the same length and the same thickness, but differ from one another in width. The patch of material and the stent cut from the patch of material can also have different lengths and thicknesses. For example, the patch of material can have a first thickness and the stent cut from the patch of material have the same thickness, but when implanted can be folded or rolled into a different thickness from the patch of material. The cut stent need not be rectangular in shape and can have a non-rectangular shape such as an angular wedge or any of a variety of shapes to provide a particular clinical result. For example, a stent cut to the shape of a "dog bone" having enlarged distal and proximal ends may provide additional fixation within the target tissues. The stent can be cut to have a narrow elongate shape on a leading end and an enlarged dimension on a trailing end to provide ease of insertion as well as at least one end providing fixation.

In some implementations, the patch of material can be a relatively larger width (e.g., 10 mm×10 mm) and the stent cut from the patch to a strip having a much smaller width (e.g., about 1.0 mm to about 1.5 mm) and the cut stent then compacted into a delivery conduit having an inner diameter of about 0.8 mm so that the width of the stent substantially fills the inner diameter. A stent can substantially fill the inner diameter of the delivery conduit even if the stent is not oversized relative to that conduit and thus, remains uncompacted. The stent can be oversized relative to the inner dimension of the conduit and be compacted into the conduit to substantially fill it. Additionally, the dimension of the cut stent can vary depending on the dimension of the conduit the stent is to be deployed through. For example, the inner diameter of the delivery conduit can be about 600 microns to about 800 microns. Thus, the stent can be cut or trephined to any of a variety of sizes depending on whether or not the stent is to be compacted into the delivery conduit and depending upon the inner dimension of that delivery conduit.

The stent cut from the patch of material can have a width, a length, and a thickness. In an implementation, the width of the stent cut from the patch of material using the cutting devices described herein can be at least 100 microns up to about 1500 microns, or between 100 microns up to 1200 microns, or between 100 microns and 900 microns, or between 300 microns and 600 microns. The stent cut from a patch of material can have a width of at least about 100 microns and a width of no more than 1500 microns, 1400 microns, 1300 microns, 1200 microns, 1100 microns, 1000 microns, 900 microns, no more than 800 microns, no more than 700 microns, no more than 600 microns, no more than 500 microns, no more than 400 microns, no more than 300 microns, or no more than 200 microns. The length of the stent cut from a patch of material can vary depending on the location of stent implantation. In some implementations, the stent has a length that is between 1 mm and 10 mm, or more preferably between 3 mm and 8 mm long. The thickness of the stent cut from the patch of material can be from 100 microns up to about 800 microns, or from 150 microns up to about 600 microns. In an implementation, the biological material forming the stent can have a thickness that is no smaller than 100 microns and no larger than 5 mm. The thickness of the stent can also depend on whether the stent is folded or rolled upon implantation such that a patch of material having a thickness of just 250 microns can cut into a stent and the stent folded at implantation to double the thickness to about 500 microns. The thickness of the stent can also depend upon what biologically-derived material is used. For example, scleral tissue or corneal tissue can often have a thickness of around 400 microns, but following harvest can shrink to about 250-300 microns. As such, a stent cut from a shrunken patch of corneal tissue may have a thickness of just 250 microns.

In some implementations, which is described in more detail below, the stent cut from the patch of material is cut so as to substantially fill the conduit through which it is advanced for delivery. In other implementations, the stent can be cut into an implant that is oversized relative to a dimension of a conduit through which it is deployed. In this implementation, the stent can be cut to have a first size, which is oversized compared to the inner dimension of the delivery conduit. The oversized stent can be primed within the delivery conduit such as by compacting or compressing with a tool so that the stent when primed within the conduit takes on a second, smaller size. Upon deployment in the eye and release of the stent from the delivery conduit, the stent may achieve a third size approaching its original first size. This will be described in more detail below.

In a non-limiting example, bio-tissue stent has dimensions no smaller than 0.1 mm and no larger than 8 mm in any direction and a thickness of not smaller than 50 microns and not larger than 8 mm. In a non-limiting example, the stent is about 6 mm in length by 300-600 microns wide by 150-600 microns thick. The cutting can be no smaller than 1 mm and no larger than 8 mm in any direction. In a non-limiting example, the cut tissue has dimensions of 100-800 microns in width and 1 mm-10 mm in length. It should be appreciated that multiple stents may be delivered to one or more target locations during an implantation procedure.

Figure 2:
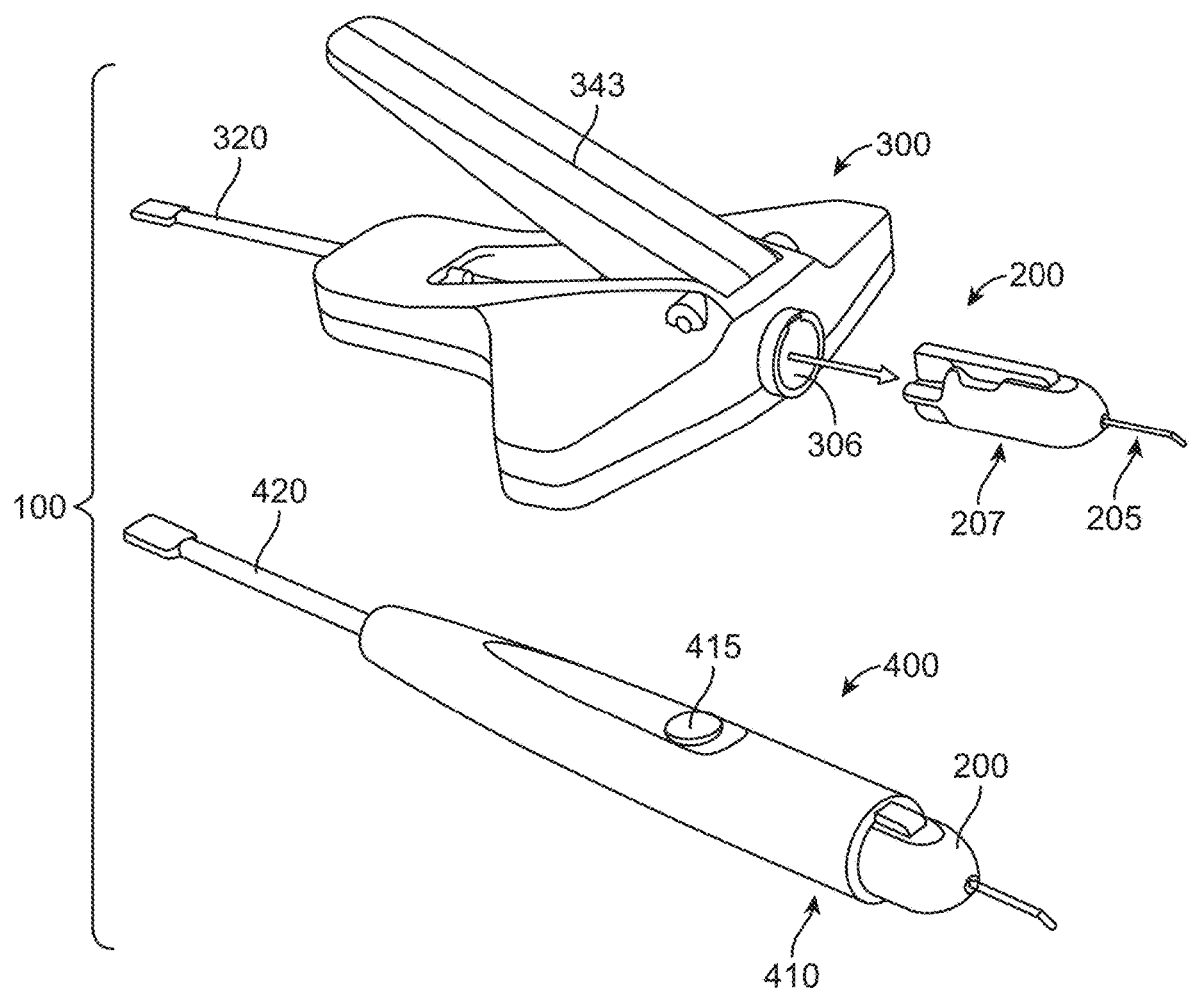
FIG. 2 is a perspective view of a system according to an implementation.
Figure 6:
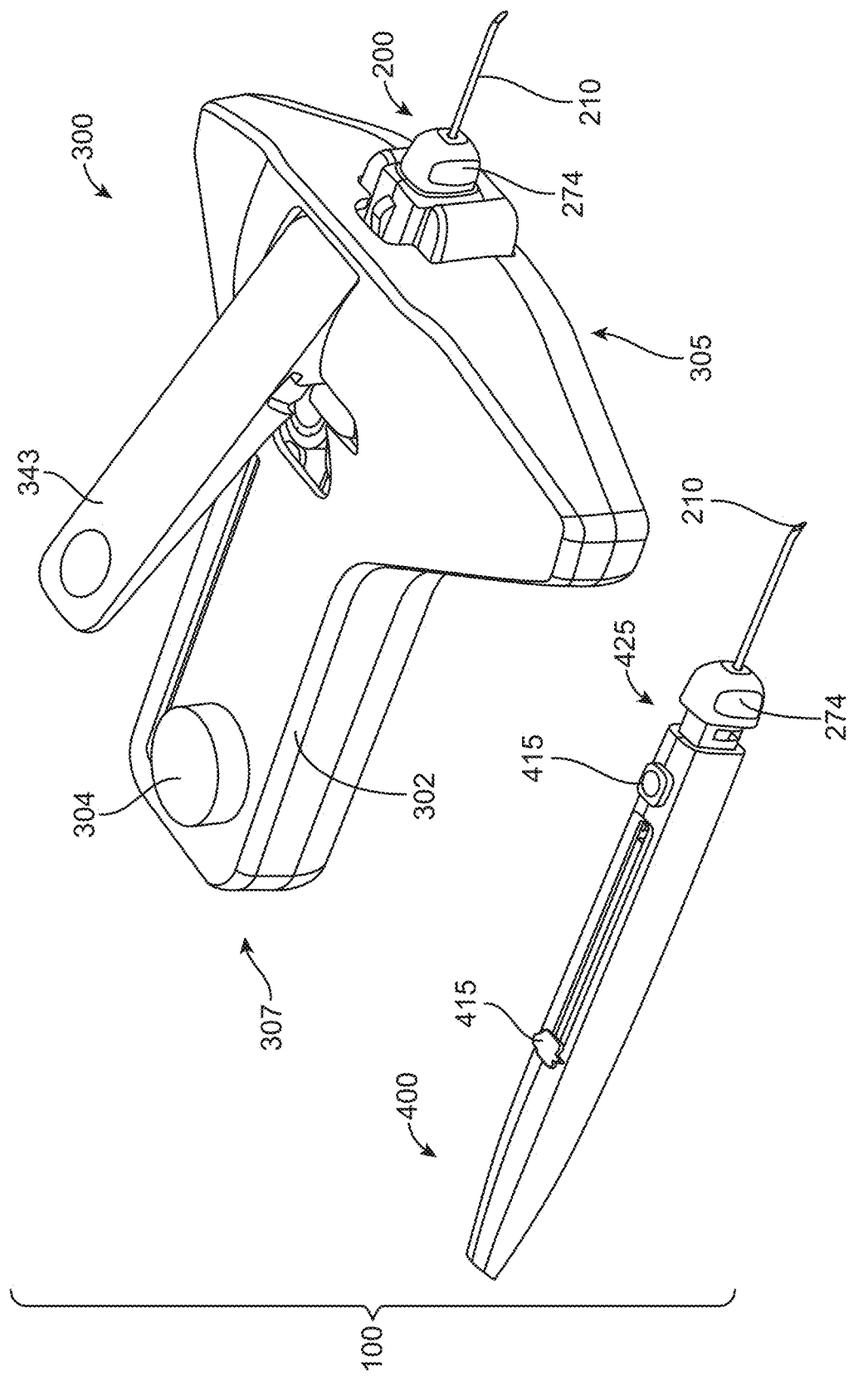
FIG. 6 is a perspective view of a system according to an interrelated implementation.

FIGS. 2 and 6 show interrelated implementations of a system 100 for preparation and delivery of a biologic intraocular stent for increasing aqueous outflow and lowering of intraocular pressure. The system 100 can include a tissue cartridge 200 having at least a portion configured to be reversibly and operatively coupled with a cutting device 300 and a delivery device 400.

Each of the systems 100 can be provided without a cutting device 300 and include only the tissue cartridge 200 and the delivery device 400. In this implementation, the tissue cartridge 200 can include a pre-cut stent 105 within the cartridge 200 that is ready to be engaged with the delivery device 400 for deployment into the eye. The cartridge 200 with the pre-cut stent 105 can be immersed within a stable solution. Thus, where the systems are described as including a cutting device 300, it should be appreciated that the cutting device 300 may not be used at the time of surgery and instead the stent 105 provided in a pre-cut and/or pre-primed configuration within at least a portion of the delivery device 400 or the tissue cartridge 200.

FIG. 2 shows a first cartridge 200 shown separated from the cutting device 300 and another cartridge 200 installed with the delivery device. The cartridge 200 is configured to receive a patch of material 101 within the cartridge 200 and fix the patch of material 101 in preparation for cutting by the cutting device 300. The cutting device 300 when operatively engaged with the cartridge 200 is configured to form the biologic intraocular stent 105 from the patch of material 101 held within the cartridge 200. The delivery device 400 when operatively engaged with the cartridge 200 is configured to deliver the cut implant 105 from the cartridge 200 to the implanted location. The tissue cartridge 200 in the implementation of FIG. 2 is configured to mate with both the cutting device 300 and the delivery device 400 such that the entire tissue cartridge 200 is removed from and transferred between the two devices 300, 400 of the system 100.

FIG. 6 shows an interrelated implementation of the system 100 and includes a tissue cartridge 200 configured to be operatively coupled with a cutting device 300 and the delivery device 400. However, the entire tissue cartridge 200 need not be fully removed from the cutting device 300 in order to couple with the delivery device 400. In this implementation, the tissue cartridge 200 can include a distal nose cone assembly 274 that is configured to uncouple from a proximal portion 207 of the cartridge 200 and couple with the delivery device 400. The nose cone assembly 274 can include at least a portion of the distal portion 205 such as a nose cone 275 and the shaft 210 extending distally from the nose cone 275.

In still further implementations, the cartridge 200 need not include a portion configured to receive a patch of material 101 within the cartridge 200. For example, the cartridge 200 can include only a nose cone assembly 274 including a nose cone 275 having a distal shaft 210. The nose cone 275 with the distal shaft 210 can be coupled to a cutting device 300 that is configured to receive the patch of material 101 within at least a region and fix the patch of material 101 in preparation for cutting by the cutting device 300. The nose cone 275 and distal shaft 210 can be arranged relative to the cutting device 300 so that the cut stent can be transferred into it for deployment in the eye. FIG. 14I illustrates in schematic a nose cone assembly 274 coupled to a cutting assembly 500. The nose cone assembly 274 includes a nose cone 275 having a proximal end coupled to the cutting assembly 500 and a distal shaft 210 extending out from the nose cone 275 along longitudinal axis A. The cutting assembly 500 can be part of a cutting device 300 as described herein.

A cartridge can include any of a variety of structural arrangements as described herein, but generally refers to a component that is transferrable between two or more devices. The cartridge can be transferrable between a cutting device and a delivery device. The cartridge can be configured to hold a patch of material for cutting into a stent as well as provide a conduit for deploying the stent into the eye. The cartridge need not be configured to hold the patch of material for cutting, however. The cartridge can include the shaft configured to receive the cut stent from the cutting assembly to then deploy the stent into the eye from the shaft. Any of a variety of configurations are described and considered herein.

Each of these systems and their respective components will be described in more detail herein.

Figure 3A:
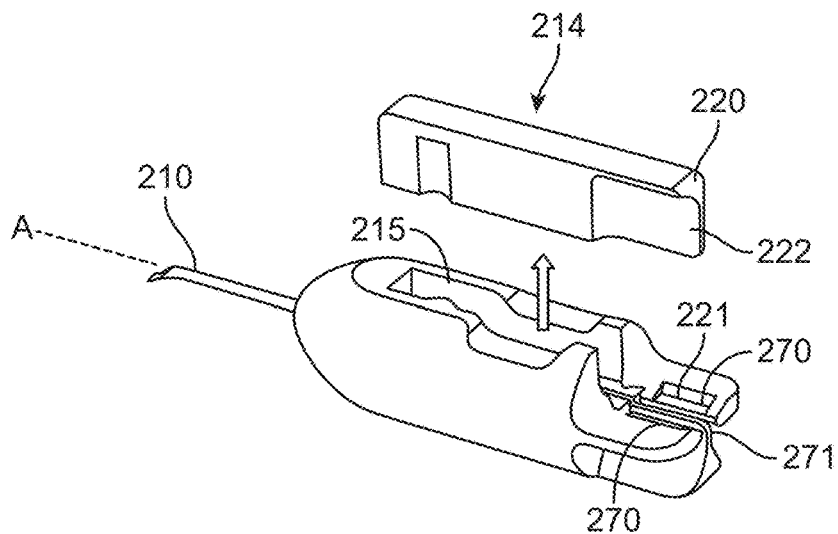
FIGS. 3A and 3B illustrate an implementation of a tissue cartridge having a cover removed.
Figure 3B:
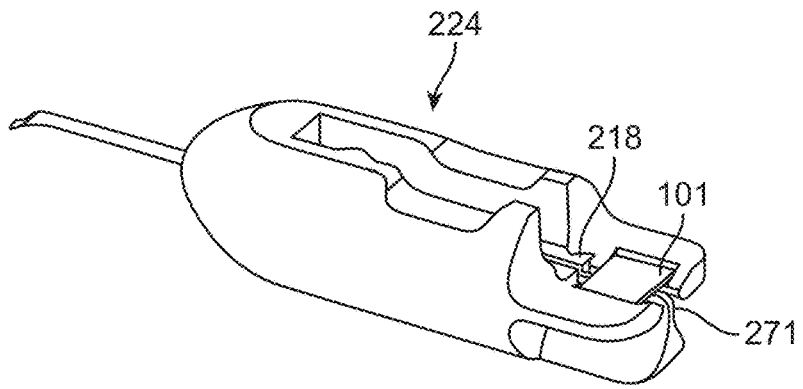
Figure 3C:
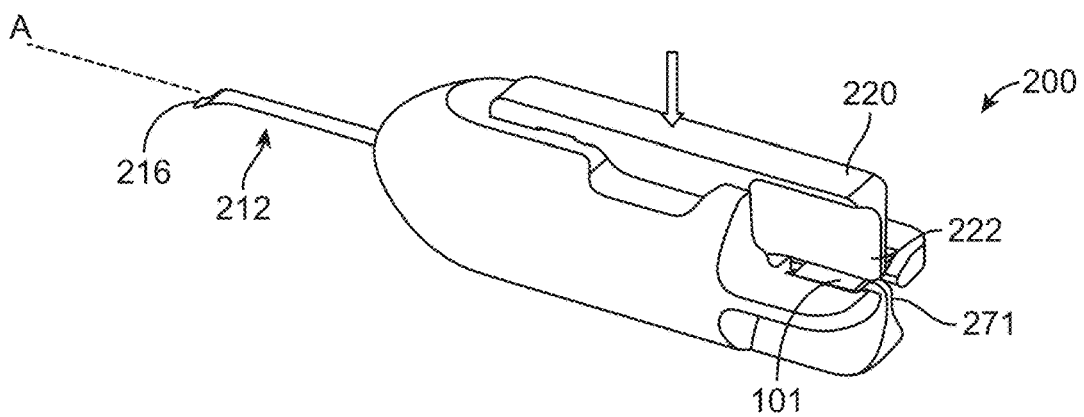
FIG. 3C illustrates the tissue cartridge with the cover installed.

FIG. 2 and also FIGS. 3A-3C show an implementation of the tissue cartridge 200 configured to hold the patch of material for cutting and for providing a conduit for deploying the cut stent into the eye. The cartridge 200 can include a distal portion 205 coupled to and extending distally from a proximal portion 207. The distal portion 205 can include an elongate member or shaft 210 having an inner conduit or lumen 238 that is sized for containing and deploying the stent 105. The proximal portion 207 can include a base 224 and a cover 214 movably attached to the base 224. The proximal portion 207 is intended to remain outside the eye while the distal portion 205 is configured to insert within the eye to deploy the stent 105 within the target tissues. The implant 105 can be advanced from the proximal portion 207 of the cartridge 200 into a deployment positioned within the distal portion 205 of the cartridge 200. The distal portion 205 of the cartridge 200 is insertable into the anterior chamber of the eye so that it may be positioned adjacent eye tissue within which the implant 105 is deployed from the cartridge 200 into the eye tissue. For example, the distal portion 205 of the cartridge 200 can be inserted ab interno into the anterior chamber through a corneal incision, while the proximal portion 207 of the cartridge 200 remains outside the eye (e.g., coupled to the delivery instrument 400).

FIG. 6 and also FIGS. 7A-7C illustrate another implementation of a tissue cartridge 200 configured to hold the patch of material for cutting and for providing a conduit for deploying the cut stent into the eye. The tissue cartridge 200 can include a distal portion 205 coupled to and extending distally from a proximal portion 207 that includes a shaft 210 having an inner conduit or lumen 238 (visible in FIG. 14I) sized for containing and deploying the stent 105. The proximal portion 207 can also include a base 224 and a cover 214 movably attached to the base 224. The distal portion 205 and shaft 210 can be removably attached to the proximal portion 207 of the cartridge 200. For example, the proximal portion 207 can remain within the cutting device 300 and a removable nose cone assembly 274 comprising the nose cone 275 and the shaft 210 can be disengaged from the proximal portion 207 and engaged with the delivery instrument 400 (see FIGS. 9A-9D).

It should be appreciated that the distal portion 205 of the cartridge 200 can be useful for other delivery pathways (e.g., trans-scleral delivery). Deploying the implant 105 into the eye tissue can include the implant 105 residing at least in part between a ciliary body and a sclera of the eye. The implant 105 can reside between the ciliary body and the sclera within a cyclodialysis cleft.

The shaft 210 of the cartridge 200 (also referred to herein as an introducer tube, applicator, conduit, or delivery body) extending in a distal direction outward from the proximal portion 207 of the cartridge 200 includes at least a portion that extends along a longitudinal axis A. At least another portion of the shaft 210 can be angled, curved, or flexible such that it can form a distal curve or a bend away from the longitudinal axis A. In some implementations, the shaft 210 can include a flexible portion and a rigid portion such that depending on relative position of the portions results in a change in shape of the shaft. The implementation shown in FIGS. 3A-3C and also FIGS. 7A-7C has a proximal portion that extends along the longitudinal axis A and a distal end region 212 that curves downward away from the longitudinal axis A. The distal end region 212 can include an opening 230 from the lumen 238 through which the stent 105 can be deployed. The opening 230 from the lumen 238 can be positioned within a plane that is perpendicular to a plane of the longitudinal axis A of the distal end region 212 of the shaft 210. The opening 230 from the lumen 238 can be positioned within a plane that is at an angle relative to the longitudinal axis A of the distal end region 212 of the shaft 210. The distal end region 212 of the shaft 210 can be beveled such that the opening 230 into the lumen 238 is elongated rather than circular and a distal-most tip 216 of the shaft 210 extends beyond the opening 230. The distal-most tip 216 of the shaft 210 can be a pointed tip or a blunt tip that is squared off such that it does not form a point. The shape of the opening 230 can be a function of the overall cross-section of the shaft 210 at the distal end region 212 as well as the angle of the opening 230 relative to the longitudinal axis A of the distal end region 212. For example, if the distal end region 212 of the shaft 210 has a rectangular cross-section and the opening 230 is cut perpendicular relative to the longitudinal axis A, the opening 230 and the cross-sectional shape of the shaft 210 are substantially matched. If the shaft 210 has a rectangular cross-section and the open 230 is cut less than perpendicular relative to the longitudinal axis A, the opening 230 may have an elongated rectangular shape compared to the rectangular shape of the shaft 210. The opening 230 may also have a first shape near the heel of the bevel and a second shape near the distal-most tip 216. For example, the opening 230 near the heel of the bevel may be rounded and the opening 230 near the distal-most tip 216 may be squared-off. It should also be appreciated that the opening 230 need not be at the distal-most end of the shaft 210. The opening 230 can be formed in a sidewall of the shaft 210 such that the stent 210 is urged out of the lumen 238 along a direction that is angled relative to the longitudinal axis of the lumen 230. The opening 230 can be positioned in the shaft 210 relative to the cartridge 200 such that is it positioned on a forward end, a lower side, an upper side, and/or another side of the shaft 210. The distal end region 212 of the shaft 210 can have a cross-sectional shape that is circular, oval, rounded rectangle, rectangle, rounded square, square, diamond, tear drop, or other shape and the distal-most tip 216 have a tip shape that varies, including blunt tip, bullet tip, spatula tip, or pointed tip. The distal end region of the shaft 210 can have any of a variety of configurations known in the ophthalmic arts.

The shaft 210 can be used to create a cyclodialysis cleft within the supraciliary space. The distal end region of the shaft 210 can be shaped to form the cleft as well as provide a conduit for a material to be delivered into the supraciliary space of the eye. The shaft 210 can also be used to deliver a viscous material such as viscoelastic fluid or a non-viscous material such as the sclera tissue. For example, viscoelastic can be delivered to a region of the eye through the shaft 210 prior to, during, and/or after implantation of the stent. The corneal incision can be created with a scalpel or other tool and the shaft 210 inserted through the incision and the distal end of the shaft 210 navigated to a desired location for delivery. The distal end of the shaft 210 can include a spatula that can be used to separate tissue layers and create the cyclodialysis cleft in the supraciliary space between the sclera and ciliary body. The dimensions, surface finish, and shape of the distal end can minimize trauma. The shaft 210 can additionally include one or more markers providing user information regarding distance of insertion. A distal end region of the shaft 210 can include one or more markers for goniometric reference for how deeply the tongue of the shaft 210 has been inserted into the supraciliary space. The length of the shaft 210 is sufficient to allow the device to be used from a temporal or superior position.

The shaft 210 of the cartridge 200 has a size and shape configured for ab interno delivery through a clear corneal incision to permit passage of the stent 105 out the distal end of the shaft 210. In at least some implementations, the distal end region 212 of the shaft 210 is sized to extend through an incision that is about 1 mm in length. In another implementation, the distal end region 212 of the shaft 210 is sized to extend through an incision that is no greater than about 2.5 mm in length. In another implementation, the distal end region 212 of the shaft 210 is sized to extend through an incision that is between 1.5 mm to 2.85 mm in length. In some implementations, the maximum outer diameter of the shaft 210 is no greater than 1.3 mm. The distal-most tip 216 of the shaft 210 can be blunt or sharp. A blunt distal-most tip 216 of the shaft 210 allows for dissecting between tissues of the eye without penetrating or cutting the tissues for positioning the stent 105. For example, the distal-most tip 216 of the shaft 210 can be configured to bluntly dissect between the ciliary body CB and the sclera S (e.g., the supraciliary space) while the stent 105 remains fully encased within the shaft 210 during the blunt dissection. In an alternative implementation, the distal-most tip 216 of the shaft 210 has a sharp cutting configuration for dissecting application and implantation through the scleral wall into the subconjunctival space. In yet another embodiment, the distal-most tip 216 can have a cutting configuration for dissecting and implantation into the Schlemm's Canal or trans-sclerally.

The shaft 210 can be a hypotube that is no greater than about 18 G (0.050" OD, 0.033" ID), 20 G (0.036" OD, 0.023" ID), 21 G (0.032" OD, 0.020" ID), 22 G (0.028" OD, 0.016" ID), 23 G (0.025" OD, 0.013" ID), 25 G (0.020" OD, 0.010" ID), 27 G (0.016" OD, 0.008" ID), 30 G (0.012" OD, 0.006" ID), or 32 G (0.009" OD, 0.004" ID). In some implementations, the shaft 210 is a hypotube having an inner diameter that is less than about 0.036" down to about 0.009". The system can incorporate a 600 micron shaft 210 or an 800 micron shaft 210. Other sizes for the shaft 210 are considered herein depending on particular patient conditions and clinical needs.

In preferred implementations, the stents described herein can be formed as solid strips of material without any lumen although it should be appreciated the stent may have also include a lumen. Thus, the stents are generally not deliverable over a guidewire as many conventional glaucoma shunts are. Additionally, the stents described herein can be formed of relatively soft tissue that is more fragile as typical shunts, which are formed of more rigid polymeric or metal material. Rigid shunts can be implanted such that a distal end of the shunt is used to create a blunt dissection at the interface of the tissues through which the shunt is being inserted. The stents described herein are preferably deployed using a retractable sleeved type of injector or introducer tube that once in proper anatomic position can be retracted leaving the stent more gently externalized and precisely positioned.

The dimensions of the shaft 210 can be selected based on the dimensions desired for the stent to be implanted. The stents 105 can have a dimension that substantially fills the inner lumen 238 of the shaft 210 (or the inner lumen of at least a portion of the shaft 210 through which it is delivered) such that the stent may be urged distally through that portion. In some implementations, the stent substantially filling the lumen is urged distally without wrinkling or being damaged. In other implementations, the stent substantially filling the lumen is urged distally through the shaft 210 in a manner that compacts the tissue into a plug having a denser configuration than the stent when cut from the patch. The dimensional difference or gap between the width and height dimensions of the stent 105 and the inner dimensions of the conduit can be up to about 200% of the dimensions of the stent 105. The maximum size of the conduit and the maximum size of the stent 105 are related. As an example, if the stent width is about 1 mm, the maximum dimension of the conduit can be 3 mm, which results in the total gap between the width of the stent and the outer wall of the conduit being 200% of the stent width. The gap may be less than 5-10% of the maximum dimension of the stent 105. Generally, the smaller the gap between the stent 105 and the conduit, the better the result for advancing the stent 105 through the conduit. If the cross-sectional area of the shaft 210 is greater than 200% the cross-sectional area of the cut stent 105, the stent 105 can buckle as it is being pushed through the shaft 210 to be implanted in the eye. The cross-sectional area of the shaft 210 and the cross-sectional area of the stent 105 are preferably substantially size-matched. The conduit can also be coated with a lubricious or low friction material (e.g., Teflon) to improve advancement of the stent 105 through the conduit during deployment.

The cross-sectional area of the shaft 210 can also be smaller than the cross-sectional area of the stent 105. As mentioned above, the stent 105 can be cut to be oversized relative to the inner diameter of the shaft 210 so that the stent 105 is compressed, compacted, or otherwise minimally manipulated for delivery through the tube. The stent can be cut to have a first size, which is oversized compared to the inner dimension of the shaft 210. The oversized stent can be primed within the shaft such as by compacting with a compacting tool 420 so that the stent 105 when primed within the conduit takes on a second, smaller size. Upon deployment in the eye and release of the stent 105 from the shaft 210, the stent 105 may achieve a third size approaching its original first size. Delivery and deployment will be described in more detail below.

Figure 5A:
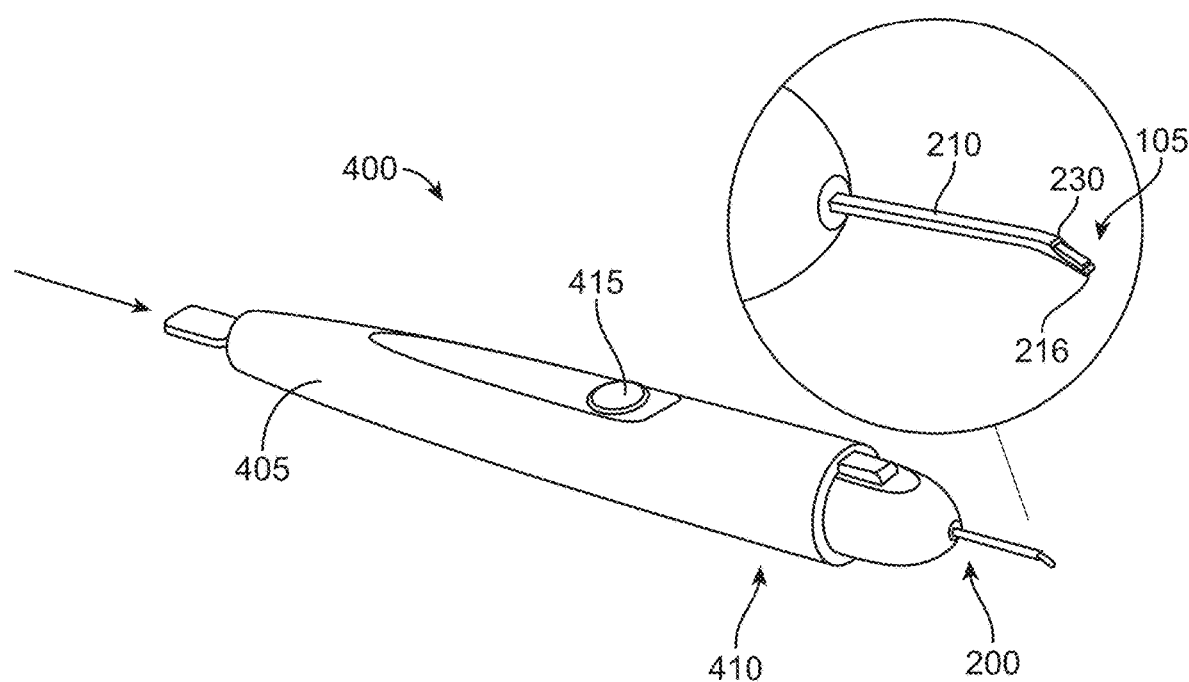
FIG. 5A illustrates an implementation of a delivery device having a tissue cartridge installed and the pusher in the advanced configuration.
Figure 5B:
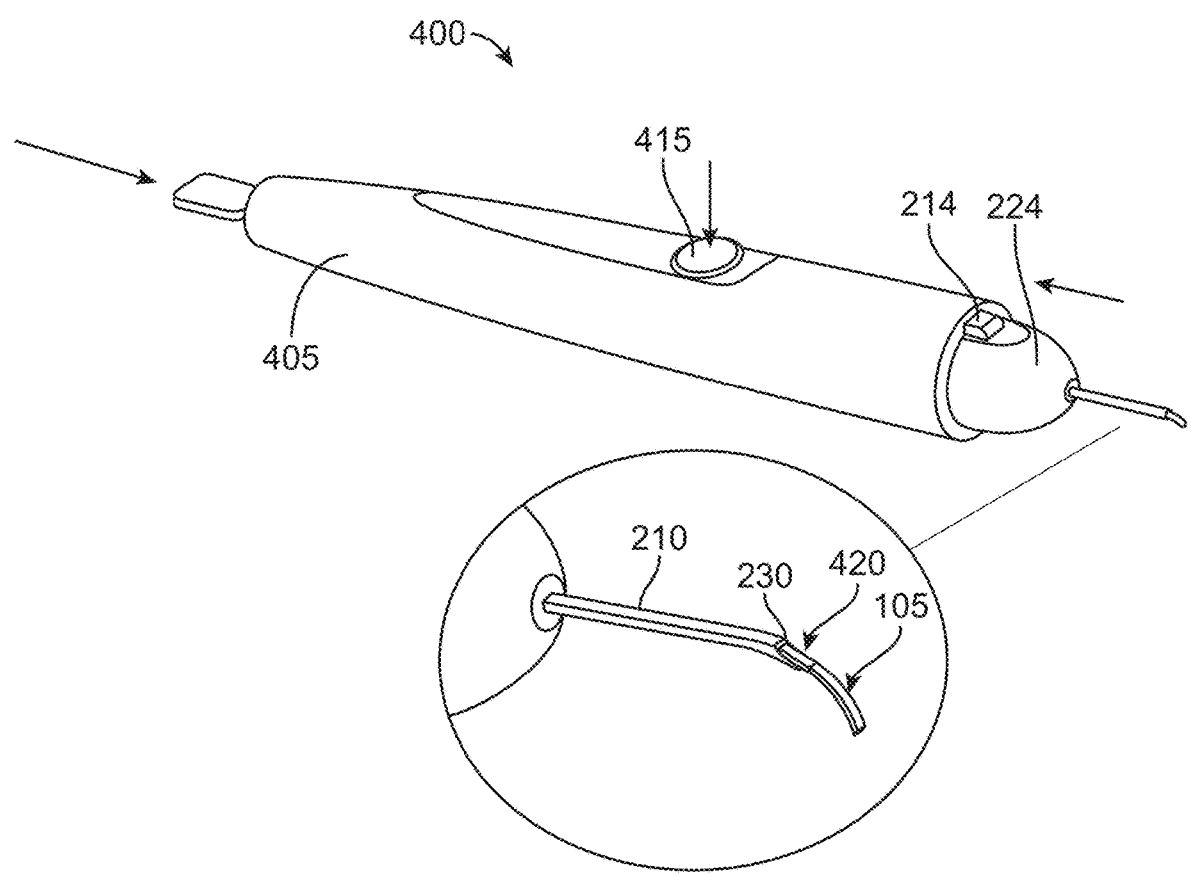
FIG. 5B illustrates the delivery device of FIG. 5A with the cartridge withdrawn relative to the pusher.

The shaft 210 can, but need not be fully tubular, nor does the shaft 210 need to be circular in cross-section. For example, the shaft 210 can be circular, oval, square, rectangular, or other geometry in cross-section. Additionally, the entire length of the shaft 210 need not have the same cross-sectional shape or size. For example, a proximal end of the shaft 210 can have a first shape and a distal end of the shaft 210 can have a second shape. FIGS. 5A-5B shows the shaft 210 is rectangular in cross-section. The lumen 238 of the shaft 210 need not be a fully enclosed channel. For example, the shaft 210 may incorporate one or more fenestrations, openings, segmental windows, or walls having one or more discontinuities such that the lumen 238 through the shaft 210 is a partially enclosed channel.

Again with respect to FIGS. 3A-3C and also FIG. 7A-7C, the proximal portion 207 of the cartridge 200 can include a base 224. A distal end region of the base 224 can be coupled to the shaft 210. A proximal end region of the base 224 can include a recess 221 configured to receive the patch of material 101. The recess 221 can include a projection 271 in the shape of an inverted V can project upward from a center line of the recess 221 that urges the centerline of the patch of material 101 upward while allowing the sides of the patch of material 101 to hang downward into corresponding channels 270 on either side of the centerline. FIGS. 7A-7C illustrate the proximal portion 207 of the cartridge 200 can be reversibly coupled to a nose cone assembly comprising the shaft 210 and the nose cone 274.

The base 224 is configured to mate with the cover 214 and to at least partially enclose the recess 221 containing the patch of material 101. The cover 214 is configured to engage at least some portion of the patch of material 101 to stabilize the tissue before and during cutting of the patch 101, for example, with the cutting device 300. In an implementation, the base 224 can include a slot 215 in an upper surface of the base 225 sized and shaped to receive the cover 214. The cover 214 slides through the slot 215 until a lower surface of the cover 214 abuts against a receiver surface 218 of the base 224. The contact between the lower surface of the cover 214 and the receiver surface 218 of the base 224 ensures the centerline of the patch of material 101 within the recess 221 is in contact with the lower surface of the cover 214 at the projection 271 (see FIG. 3C).

The cover 214 is shown in FIGS. 3A-3C as a completely removable element from the base 224. The cover 214 and base 224 can optionally be coupled together by a hinge or other mechanical feature. For example, the cover 214 can rotate around a pivot axis of the hinge and stay connected to the base 224 even when in a configuration to reveal the recess 221. FIGS. 7A-7C illustrate the cover 214 can toggle between an open and closed configuration by applying a downward pressure on a forward end of the cover 214 (FIG. 7A) to open the cover 214 and a downward pressure on a back end of the cover 214 to close the cover 214 (FIG. 7C). For example, the cover 214 can be lifted into an open configuration revealing the recess 221 of the base 224 within which the patch of material 101 can be positioned. When the cover 214 is positioned back into the closed configuration, the patch 101 can be compressed and/or tensioned between the cover 214 and the base 224. The cartridge 200 can be inserted within 306 of the cutting device 300 once the cover is in the closed configuration (see FIG. 8)

The cover 214 (or some other element) can be configured to additionally apply an amount of tension on at least a portion of the patch of material 101, such as stretching in an outward direction from the centerline of the patch of material 101 before cutting occurs as described in U.S. Pat. No. 10,695,218, issued Jun. 30, 2020, and is incorporated by reference herein in its entirety.

The patch of material 101 can be inserted by a user into the cartridge 200 at the time of surgery. The patch of material 101 may be provided in a size that approximates the size of the recess 221 within the base 224. The user may trim the patch of material 101 before installing it in the recess 221. Alternatively, the cartridge 200 can be provided pre-loaded with a patch of material 101 positioned within the recess.

Figure 10A:
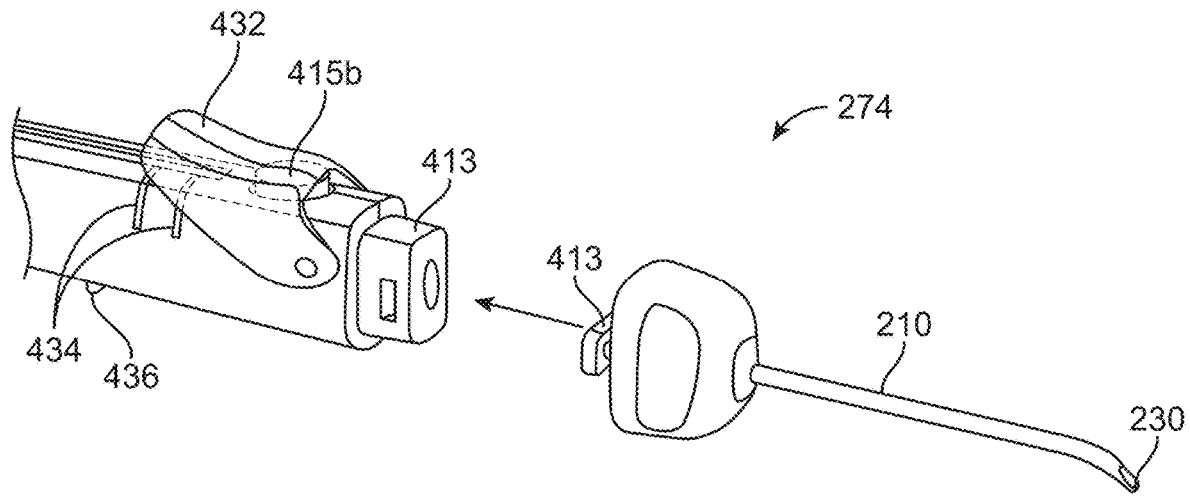
FIG. 10A illustrates the nose cone prior to engagement with a distal end region of the delivery device.
Figure 10B:
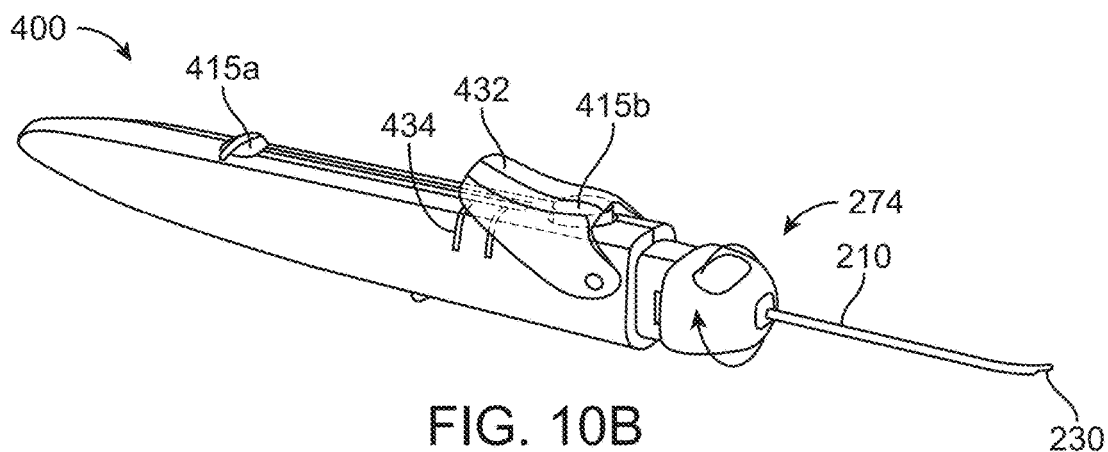
FIG. 10B illustrates the nose cone after engagement with the distal end region of the delivery device and prior to attachment.
Figure 10C:
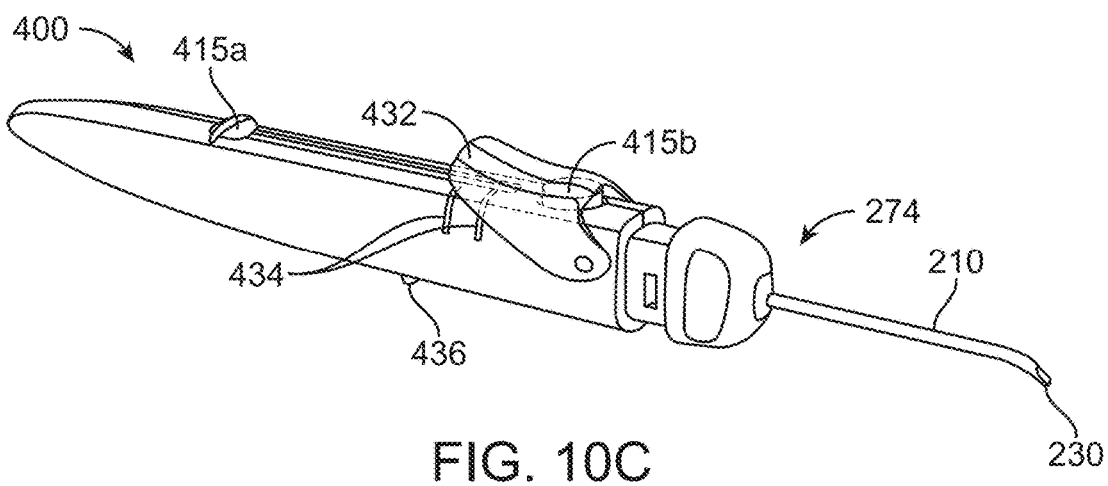
FIG. 10C illustrates the nose cone engaged and attached with the distal end region of the delivery device.

As mentioned elsewhere herein, the cartridge need not be configured to hold the patch of material 101 for cutting by the cutting device 300. Rather, the cutting device 300 can be configured to hold the patch of material 101 for cutting and then transfer the cut stent into the cartridge that is coupled to the cutting device 300. FIGS. 10A-10C illustrate an implementation of a cartridge 200 that forms a nose cone 274 having a shaft 210 into which the cut stent can be loaded prior to insertion in the eye. The nose cone 274 can reversibly couple to a cutting device 300 and, once loaded with the cut stent, can be removed from the cutting device 300 and couple with the delivery device 400. The cartridge 200 can be positioned relative to the cutting device 300 that is configured to hold the patch of material 101 and cut it into a stent 105. The coupling between the cutting device 300 and the cartridge 200 can align the longitudinal axis of the distal shaft 210 relative to a region of the cutting device so that the cut stent 105 can be transferred into the distal shaft 210 such as with a rod or other tool that will be described in more detail below. The cartridge 200 with the distal shaft 210 having the stent 105 positioned inside it can then be uncoupled from the cutting device 300 and transferred to a portion of the delivery device 400. Thus, the cartridge 200 need not include a portion configured to hold the patch of material 101 for cutting and instead includes a transferrable portion that can couple alternatingly with a region of the cutting device 300 and a region of the delivery device 400. This will be described in more detail below.

FIGS. 4A-4J and also FIG. 8 show implementations of a cutting device 300 having a cutting assembly for cutting a stent from a patch of material 101. FIGS. 14A-14H illustrate various implementations of a cutting assembly 500 that can be incorporated into the cutting device 300. The cutting device 300 is configured to cut or otherwise prepare the biologically-derived tissue or patch of a material 101 having a first contour or shape (e.g., a wider, square sheet or patch of material) into a second contour or shape (e.g., a narrower, rectangular strip of material) that conforms to an implantable stent 105 having the dimensions described herein. The cutting performed using the cutting devices 300 described herein can involve guillotine, punch, rotating, sliding, rolling, or pivoting blade cutting motion. In some implementations, the cutting is performed orthogonal to the plane of the patch of material. In some implementations, the cutting is performed axially along the conduit of implantation such that the axis of cutting can be aligned, within, or parallel to an implantation conduit to allow unimpeded tissue loading and transfer for implantation without manipulating, tearing, or damaging the fragile stent tissue.

As mentioned above, the cutting process is preceded by a tissue fixation step wherein the biologically-derived tissue that forms the stent is firmly fixed between two appositional planar surfaces to ensure the tissue is not wrinkled or malformed and the subsequent cut is of accurate dimensions. The fixation can optionally provide compression as well as tension or stretching of the tissue within at least one plane to ensure clean cutting through the tissue. The cutting assembly 500 can hold the patch of material 101 prior to cutting or the patch of material 101 can be held within a region of the tissue cartridge 200 prior to cutting by the cutting assembly 500. In some implementations, the cutting device 300 in combination with the cover 214 of the cartridge 200 can incorporate an anterior-to-posterior capture such that the material 101 to be cut is held fixed on the z-plane preventing movement prior to engaging the tissue with the cutting member 312.

The cutting can be performed within a path or conduit formed within the cartridge 200. Thus, implant 105 cut from the patch of material 101 can simultaneously or subsequently position the implant 105 within the conduit for delivery or align the implant 105 with the conduit for delivery so that the cut implant 105 can be delivered to the eye through the conduit without the cut implant 105 needing to be transferred from the cartridge 200.

As an example, the patch of material 101 held within the recess 221 of the cartridge 200 is cut by the cutting member 312 of the cutting device 300 forming a cut stent 105 within the recess 221 of the cartridge that can be urged distally from the recess 221 into the lumen 238 of the shaft 210 of the cartridge 200 so it can be deployed in the eye all without removing the cut stent 105 from the cartridge 200 or at least the distal portion 205 of the cartridge 200.

Figure 4A:
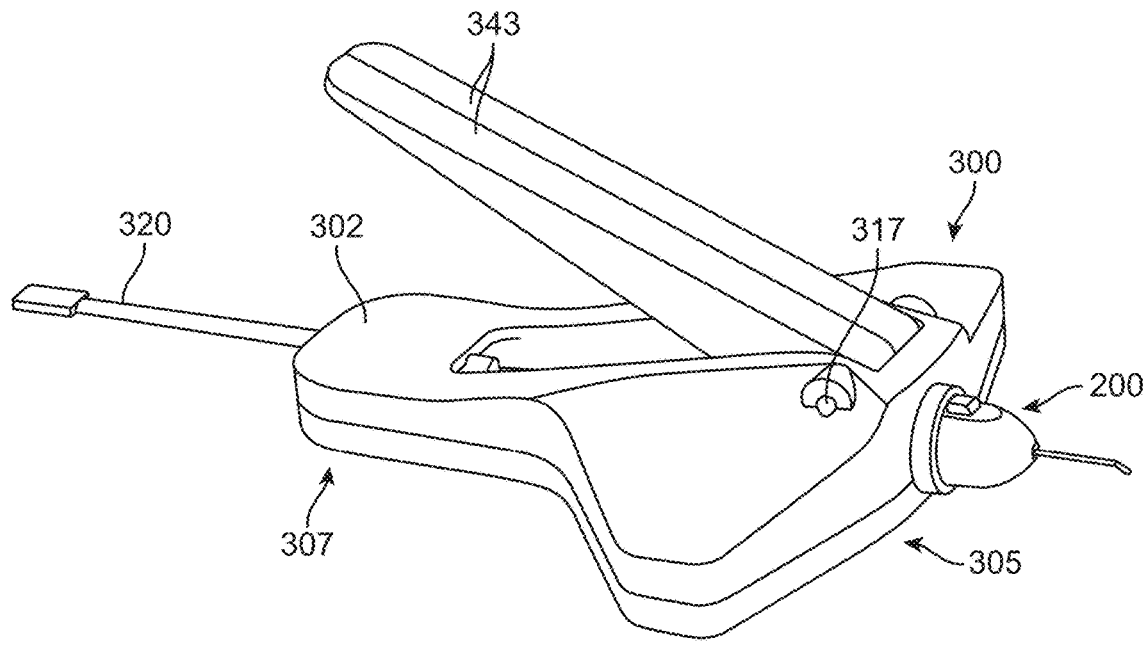
FIG. 4A illustrates an implementation of a cutting device having a tissue cartridge installed and the cutter in the open configuration.
Figure 4B:
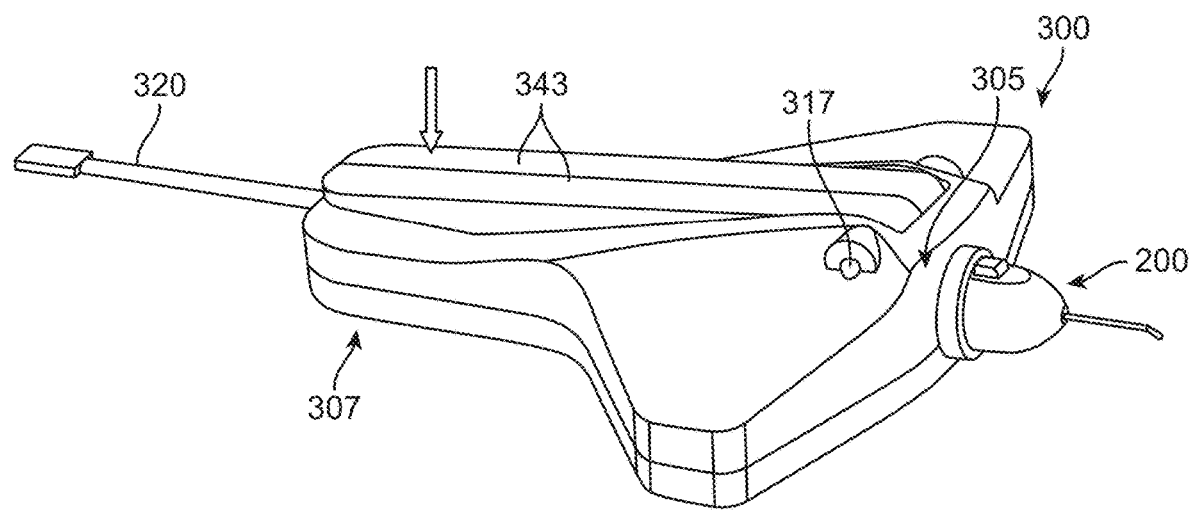
FIG. 4B illustrates the cutting device with the tissue cartridge installed and the cutter in the cut configuration.

With respect to FIGS. 4A-4B and also FIG. 6, the cutting device 300 can include a base 302 having a distal portion 305 and a proximal portion 307. The distal portion 305 can include a distal opening or receptacle 306 sized and shaped to receive the proximal portion 207 of the cartridge 200. The inner diameter of the receptacle 306 can be sufficient to receive an outer dimension of the proximal portion 207 so that the proximal portion 207 can be inserted a distance within the receptacle 306. The cover 214 of the cartridge 200 positioned within the slot 215 to maintain the patch of material 101 within the recess 221. An upper surface of the cover 214 can extend above the upper surface of the base 224 such that the outer dimension of the proximal portion 207 is keyed. In other words, the outer dimension of the cartridge 200 is keyed and can only be inserted within the receptacle 306 of the cutting device 300 in a single orientation (e.g., the cover 214 positioned on an upper side).

Figure 4C:
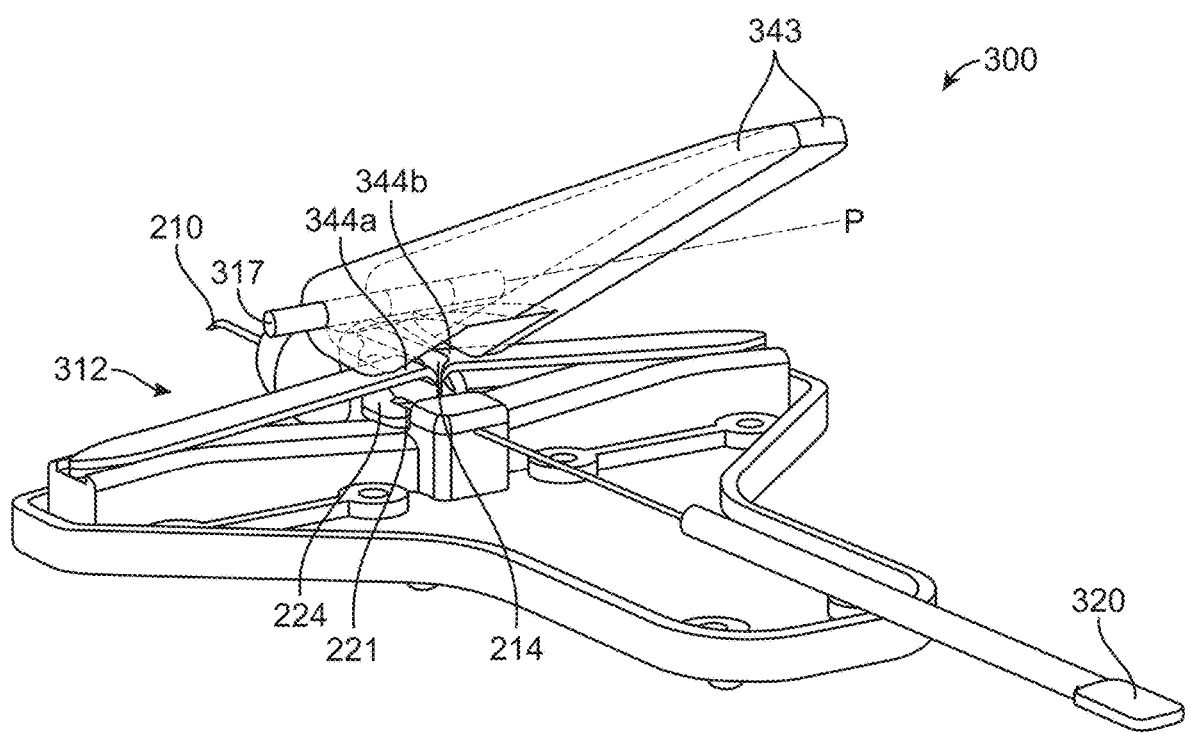
FIG. 4C is a partial view of the cutting device of FIG. 4B showing the cutter.

The cutting device 300 can additionally include a cutting assembly 500 having a cutting member 312 configured to cut the patch of material 101 within the recess 221 of the cartridge into a stent 105 (see FIG. 4C). The configuration of the cutting member 312 can vary. In this configuration, the cutting member 312 can include at least a first blade 344a and a second blade 344b separated a distance from the first blade 344a. The first and second blades 344a, 344b can be positioned above the patch of material 101 when the cartridge 200 is installed within the receptacle 306 of the cutting device 300. Actuation of the cutting member 312 causes the first and second blades 344a, 344b to be urged towards the patch of material 101 cutting through the thickness thereby forming the stent 105. The blades 344a, 344b can have a width along the longitudinal axis A of the cartridge 200 sufficient to cut a full length of the patch of material 101. The distance between the blades 344a, 344b can be designed to achieve the width desired for the cut stent 105.

In some implementations, the blades 344a, 344b can be positioned above the patch of material 101 to be cut and corresponding lower blades 345a, 345b can be positioned below the patch of material 101. Thus, as the blades 344a, 344b are urged downward towards the patch of material 101, they urge the patch of material 101 towards the lower blades 345a, 345b such that the corresponding upper and lower blades cut completely through the material 101 in two locations creating the stent 105.

The cutting member 312 can be actuated by a user to move the blades. The cutting device 300 can include one or more handles 343 that movably coupled to the base 302 to actuate the cutting member 312. The handle(s) 343 can be coupled by a hinge 317 such that the handles 343 rotate around a pivot axis P of the hinge 317 relative to the base 302. For example, the handles 343 can be lifted to pivot into an open configuration as shown in FIG. 4A and rotated back around the pivot axis P into the cutting configuration as shown in FIG. 4B.

Figure 4D:
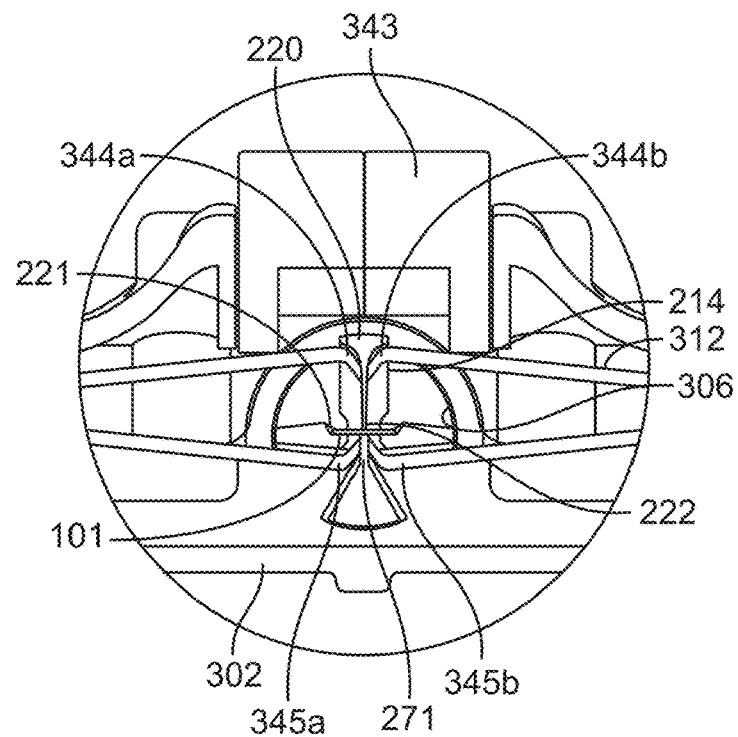
FIG. 4D is a cross-sectional partial view of the cutting device of FIG. 4A.
Figure 4E:
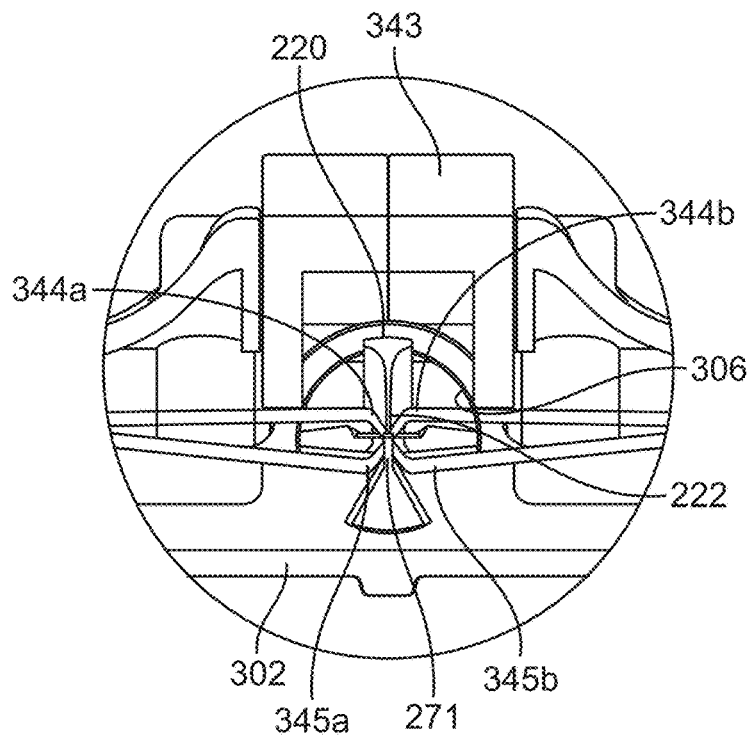
FIG. 4E is a cross-sectional, partial view of the cutting device of FIG. 4B.

The cartridge 200 may be inserted within the receptacle 306 of the cutting device 300 when the handles 343 are lifted into the open configuration and the cutting member 312 is positioned away from the cutting configuration. As best shown in FIGS. 4D-4E, the cartridge 200 may be slid into the receptacle 306 to position the recess 221 holding the patch of material 101 below the upper blades 344a, 344b and above the lower blades 345a, 345b. The cover 214 holding the patch of material 101 within the recess 221 can include an upper portion 220 that tapers into a narrower lower portion 222. The lower portion 222 of the cover 214 is aligned with the projection 271 of the recess 221 and traps the patch of material 101 therebetween. The upper portion 220 of the cover 214 can slide above the upper blades 344a, 344b as the cartridge 200 is installed with the cutting device 300. The lower portion 222 of the cover 214 is sized to slide between the upper blades 344a, 344b as the cartridge 200 is inserted within the receptacle 306 of the cutting device 300. FIG. 4D shows the upper blades 344a, 344b separated a distance from the lower blades 345a, 345b and the narrow lower portion 222 of the cover 214 positioned between them. FIG. 4E shows the handles 343 rotated back down into the cutting configuration and the upper blades 344a, 344b urged downward towards the patch of material 101 and toward the lower blades 345a, 345. The patch of material 101 is cut by the corresponding upper and lower blades forming the stent 105. The distance between the upper and lower blades determines the width of the stent 105 that is cut from the patch of material 101.

The handles 343 can open along any of a number or orientations relative to the base 302. For example, the pivot axis P of the hinge 317 can be substantially orthogonal to the longitudinal axis of the base A. In this implementation, the hinge 317 can be positioned on a distal end of the base 302 such that the handles 343 hinge open by rotating upward and toward the distal end of the base 302. The upper blades 344a, 344b may be spring-loaded such that they readily return to an open configuration as the handle 343 is lifted or released.

The stent 105, once cut, is contained on all sides by the cartridge 200 and the cutting member 312 creating a complete enclosure or stent cutting chamber for the stent 105 within the assembly of the cutting device 300 and the cartridge 200. For example, the floor and ceiling of the stent cutting chamber can be formed by the lower portion 222 of the cover 214 and the projection 271 of the recess 221. The walls of the stent cutting chamber can be formed by the upper blades 344a, 344b, and the lower blades 345a, 345b of the cutting member 312. Together, the walls of the stent cutting chamber can form a rectangle to help constrain and direct the pusher 320 of the cutting device 300 that is advanced to push the stent 105 from the stent cutting chamber distally into the lumen 238 of the shaft 210. In an implementation, the stent cutting chamber can be at least partially arced or circular in cross-section. The upper and lower surfaces of the cutting chamber can be curved or non-planar. As an example, the lower portion 222 of the cover 214 can be recessed forming a concavity forming arched ceiling to the cutting chamber. The floor of the cutting chamber formed by the projection 271 may incorporate a corresponding concavity. The arched ceiling and recessed floor of the cutting chamber reduces the amount of open space created around the cut stent 105 relative to the inner walls of the shaft that could otherwise result in the push rod going off-track or allowing the cut stent 105 to divert off the desired path during deployment. Minimizing the air space within the shaft relative to the trephine stent 105 improves advancement of the stent 105 through the device. The cut stent 105, in turn, can have a cross-sectional shape that conforms more closely to the cross-sectional shape of the delivery conduit through which the stent 105 must be advanced. The corresponding shape eliminates excess space on the upper and lower sides of the cut stent 105 relative to the conduit. This, in turn, provides better guidance for the pusher 320 to advance the cut stent 105 towards the distal end of the shaft. The stent 105 can also be cut to be oversized relative to the conduit as discussed elsewhere herein and compressed, compacted, or otherwise manipulated within the conduit prior to deployment.

Figure 4F:
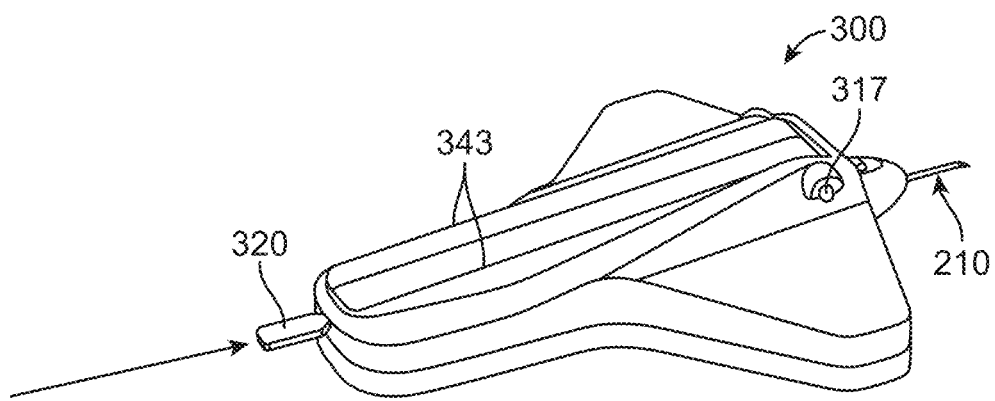
FIGS. 4F-4G illustrate the pusher in advanced and withdrawn configurations relative to the base of the cutting device.
Figure 4G:
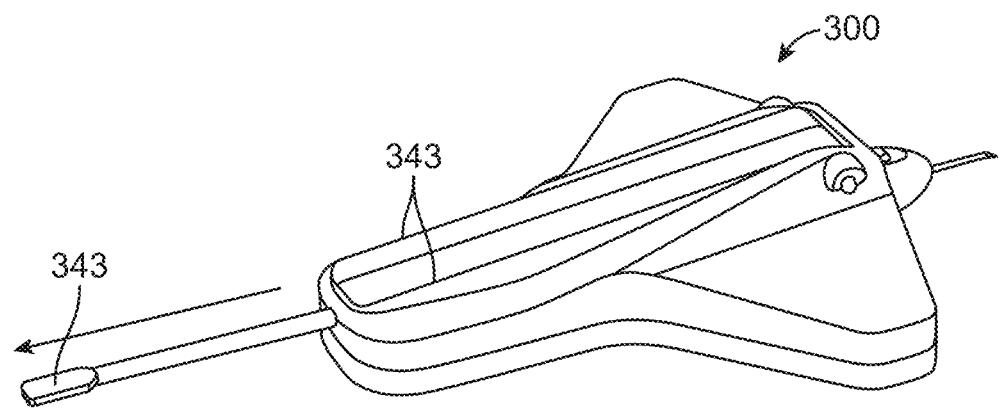
Figure 4H:
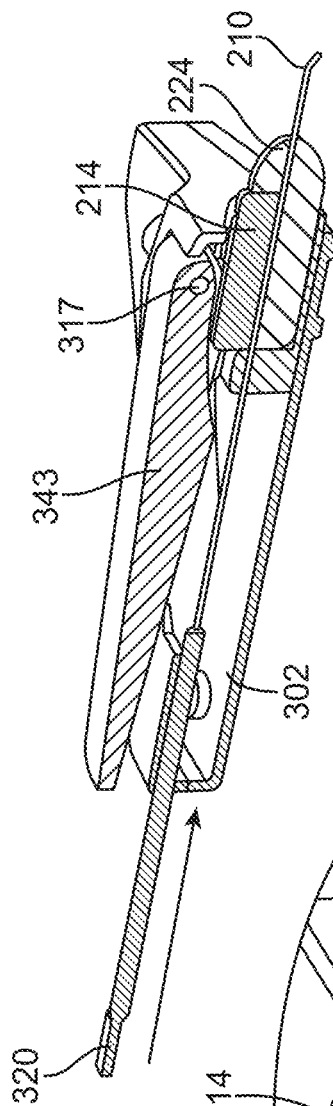
FIG. 4H is a cross-sectional view of the cutting device of FIG. 4G.
Figure 4I:
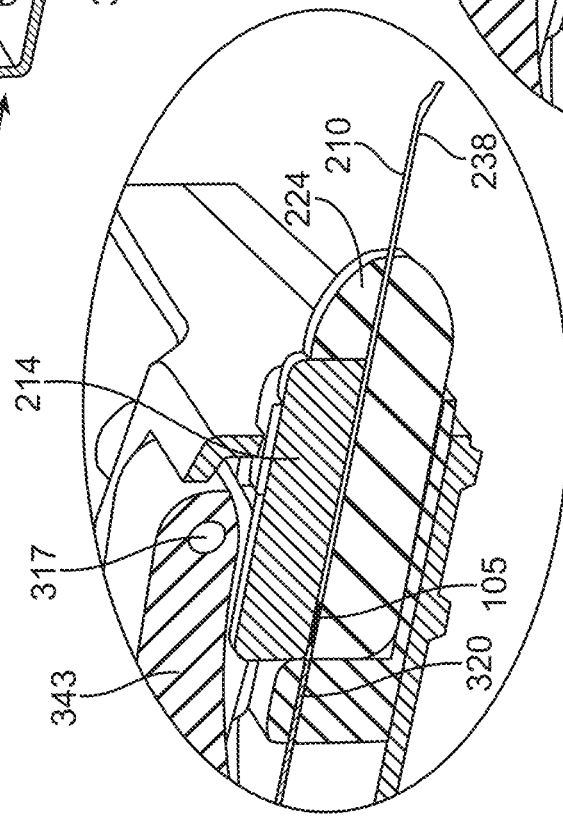
FIGS. 4I-4J are cross-sectional partial view of the cutting device of FIG. 4F.
Figure 4J:
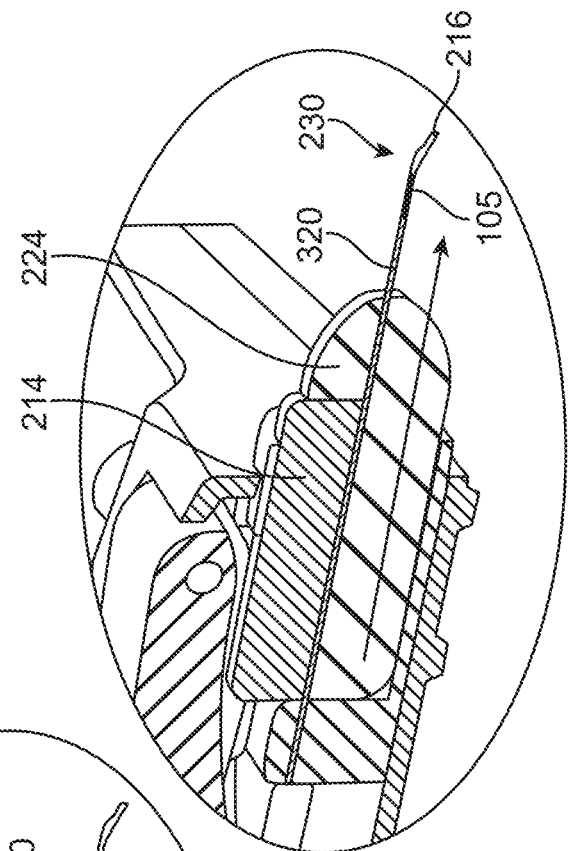

The stent 105, once cut, can be axially aligned with the lumen 238 of the shaft 210 of the cartridge 200. FIGS. 4F-4G and also FIGS. 4H-4J show the cutting device 300 can include a pusher 320 configured to slide distally relative to the base 302 into a proximal end region the cartridge 200 to advance the cut stent 105 from the location of this complete enclosure along the implantation conduit into the lumen 238 of the shaft 210. The pusher 320 is not visible in the implementation of FIG. 6. However, the base 302 can include an actuator 304 such as a dial, button, slider, or other input that is operatively coupled to the pusher 320 that upon actuation causes the pusher 320 to move distally relative to the base 302. Any of a variety of user actuators 304 are considered herein to move the pusher 320 to prime the stent 105 in place relative to the lumen 238. This priming step with the pusher 320 of the cutting device 300 ensures the cut stent 105 is held within a fully enclosed space on all sides (i.e. a region of the shaft 210) after removal of the cartridge 200 from the cutting device 300 and before coupling of the cartridge 200 with the delivery device 400.

FIG. 4H shows that while the handles 343 are urged downward towards the base 302 (e.g., the blades 344 positioned in the cutting configuration relative to the implant 105), the pusher 320 of the cutting device 300 can be advanced distally through the base 302. FIG. 4I shows the pusher 320 ready to engage the stent 105 within the recess 221 on a proximal end. FIG. 4J shows the pusher 320 has advanced the stent 105 distally into the lumen 238 of the shaft 210 of the cartridge 200. As mentioned above, the blades 344 besides, the cover 214 above, and the projection 271 below created the complete enclosure for the cut stent 105 on all sides preventing the stent 105 from buckling within the lumen 238 during this distal advancement into the lumen 238. The conduit within which the stent 105 is held is size-matched (or under-sized) to the outer dimension of the stent being implanted thereby preventing buckling and wrinkling as the stent 105 is urged into the primed position.

The stent 105 can be urged into a distal end region 212 of the shaft 210 and the cartridge 200 removed from the cutting device 300. Once the cutting device 300 and the cartridge 200 are disengaged with one another, the cartridge 200 is ready to be loaded with the delivery device 400 to insert the stent 105 into the eye.

The patch of material 101 can be cut and loaded within the shaft 210 of the cartridge 200 in a variety of ways. As discussed elsewhere, the patch of material 101 can be cut to substantially the same size as the conduit through which it will be delivered. The patch of material 101 can preferably be cut to a size that is slightly larger than the size of the conduit through which it is delivered so that the stent 105 is compressed and packed within the conduit so that it may be more easily advanced through the lumen 238. The cutting can be performed as described above with respect to FIGS. 4A-4E. The cutting of the patch of material and transfer into the shaft 210 can also be performed using other cutting assemblies 500 as described below and with respect to FIGS. 14A-14H. The cutting assemblies 500 described herein can form part of the tissue cartridge 200, the cutting device 300, or the delivery device 400. Preferably, the cutting assembly 500 is part of the cutting device 300. The cutting device 300 can couple to at least a portion of the cartridge 200 such as the nose cone assembly 274 with the distal shaft 210 extending from the nose cone 275 so that the cut stent 105 can be primed within the shaft 210 for delivery using the delivery device 400. The cartridge 200 can include a proximal portion 207 configured to hold the patch of material for cutting as shown in FIG. 2, 3A-3C, or 7A-7C or the removable nose cone 274 and shaft 210 as shown in FIGS. 9A-9D, 10A that does not include a proximal portion 207 for holding the patch of material. The cartridge 200 whether configured to hold a patch of material for cutting or not can be a transferrable component that is designed to couple with a cutting assembly, primed with the cut stent, removed from the cutting assembly, and coupled with a delivery device for deployment of the cut stent in the eye.

Figure 14A:
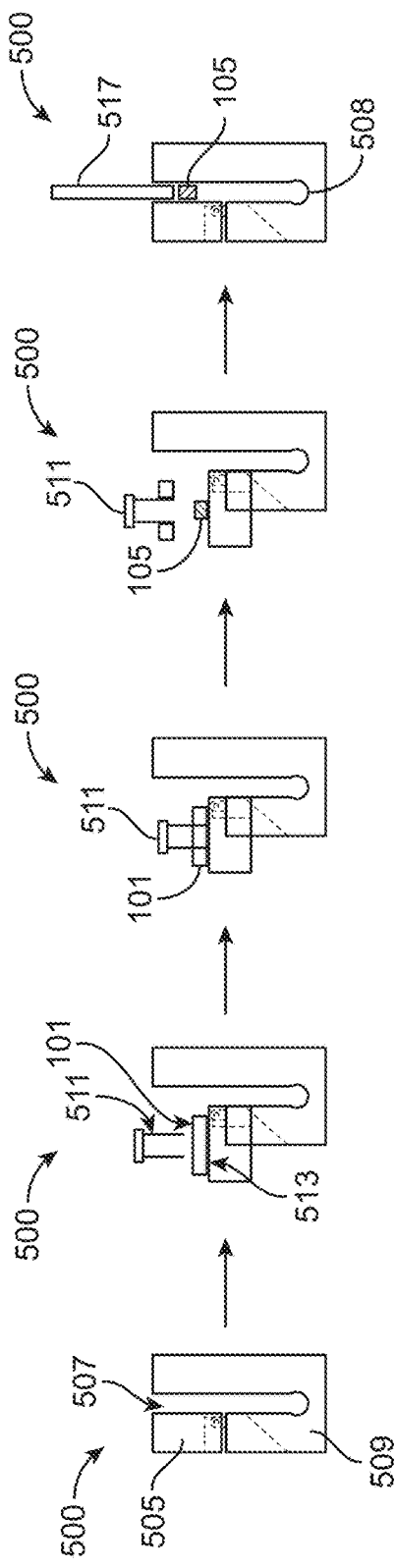

FIG. 14A shows an implementation of a cutting assembly 500. The cutting assembly can be part of a cutting device 300 configured to engage with a cartridge. The cutting assembly 500 can cut a patch of material 101, which can be held within the cartridge or within a region of the cutting assembly 500. The cut stent can be transferred from the cutting assembly 500 into a distal shaft 210 of the cartridge 200 for delivery through the shaft into an eye. The cutting assembly 500 can incorporate a cutting die 511 positioned relative to a slot 507 in a base 509 and a movable member 505 having planar cutting surface 513 coupled to the base 509. The movable member 505 can be swiveled 90 degrees relative to the base 509 from a first position to a second position. When the movable member 505 is swiveled to its second position the patch of material 101 can be placed against the cutting surface 513. The cutting die 511 can compress the patch of material 101 against the cutting surface 513. Advancing the cutting die 511 towards the cutting surface 513 can cut through the patch of material 101 in two locations as described elsewhere herein. The excess tissue can be removed from the cutting surface 513 and the movable member 505 still holding the cut stent 105 on its cutting surface 513 swiveled back towards the first position. This arranges the cut stent 105 on the cutting surface 513 within the path of the slot 507 so that a compacting tool 517 or other member can load the cut stent 105 into the slot 507. The slot 507 can have a terminal region 508 that aligns with a longitudinal axis A of the distal shaft 210 when the cartridge 200 is coupled to the cutting device 300. The terminal region 508 can have a cross-sectional shape that is rounded similar to a cross-sectional shape of the distal shaft 210. The cut stent 105 positioned within the terminal region 508 can then be urged into the lumen of the distal shaft 210 so that it is primed for delivery. The size of the slot 507 and/or the terminal region 508 can be smaller than the size of the cut stent 105 so that advancement of the compacting tool 517 urging the cut stent 105 into the slot 507 causes the stent 105 to be compressed and compacted into a plug. Once the cut stent 105 is positioned within the distal shaft 210 of the cartridge 200, the cartridge 200 can be removed from the cutting device 300 and transferred to a delivery device 400 for deployment in the eye.

Figure 14B:
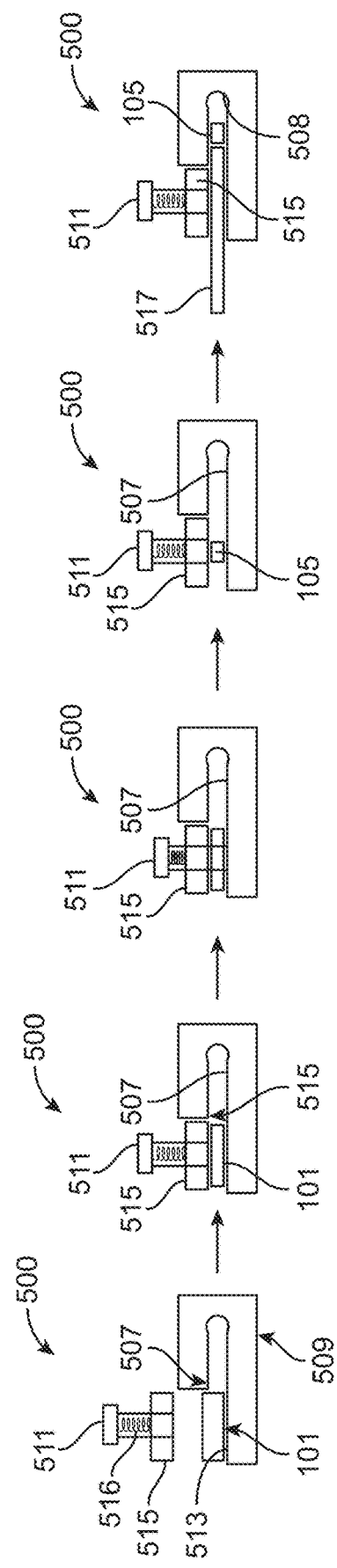

FIG. 14B shows an interrelated implementation of a cutting assembly 500 for cutting the patch of material 101 and transferring the cut stent 105 for delivery. As with the embodiment of FIG. 14A, the cutting assembly 500 can be part of a cutting device 300 configured to engage with a cartridge. The patch of material can be held within a region of the cartridge for cutting or can be held by a portion of the cutting assembly 500. The cutting die 511 can insert through a compression pad 515 to cut the patch of material 101. The patch of material 101 can be positioned against a cutting surface 513. The cutting surface 513 need not be part of a movable member as in the prior implementation, but can be at least a portion of the base 509. The patch of material 101 can be compressed between the cutting surface 513 of the base 509 and the compression pad 515. The cutting die 511 can be advanced through the compression pad 515 so that blades of the cutting die 511 slice through the patch of material 101 in two locations. After the patch of material 101 is cut the excess tissue can be removed and pressure applied by the compression pad 515 released. The cutting die 511 can include a spring 516 so that it returns to its initial position and the pressure pad 515 and cutting die 511 no longer apply a pressure against the cut stent 105. The cut stent 105 can be positioned relative to a slot 507 in the base 509 so that the compacting tool 517 can urge the cut stent 105 through the slot 507 toward the terminal region 508. As discussed elsewhere, the cut stent 105 can be oversized relative to the size of the slot 507 so that urging the stent into the conduit compresses and compacts the stent 105 for delivery. The slot 507 can have a terminal region 508 that aligns with a longitudinal axis A of the distal shaft 210 when the cartridge is coupled to the cutting device 300. The cut stent 105 positioned within the terminal region 508 can then be urged into the distal shaft 210 so that it is primed for delivery. The cartridge, now containing the cut stent 105, can be removed from the cutting device 300 and transferred to a delivery device 400 for deployment in the eye.

Figure 14C:
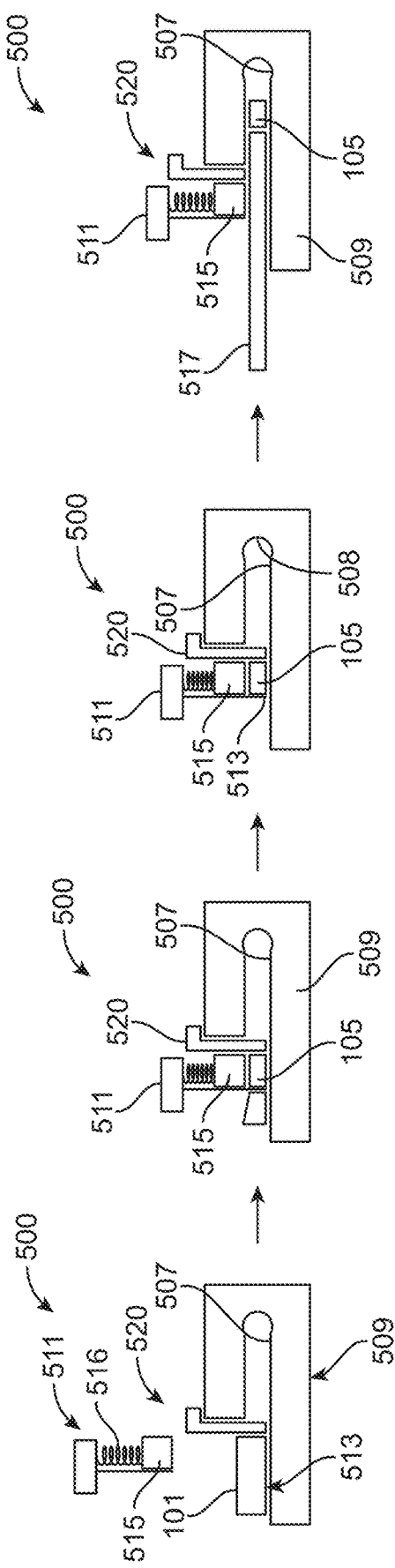

FIG. 14C shows an interrelated implementation of a cutting assembly 500 for cutting the patch of material 101 and transferring the cut stent 105 for delivery. The cutting assembly 500 can additionally incorporate a movable stop 520 positioned between the patch of material 101 and the slot 507 through which the cut stent 105 is to be advanced. The compression pad 515 and cutting die 511 can compress the patch of material 101 against a cutting surface 513 of the base 509. The patch of material 101 can be enclosed between the cutting surface 513 on an underside, the movable stop 520 on a distal side and the compression pad 515 on an upper side. The cutting die 511 can include a single blade and be advanced through the compressed patch of material 101 to cut the patch in a single location creating a stent 105. The cutting die 511, compression pad 515, and movable stop 520 can be withdrawn away from the cut stent 105 so that the compacting tool 517 can urge the cut stent 105 distally into the slot 507 for delivery. The terminal region 508 of the slot 507 can align with a longitudinal axis A of the distal shaft 210 when the cartridge is coupled to the cutting device 300. The cut stent 105 positioned within the terminal region 508 can then be urged into the distal shaft 210 so that it is primed for delivery as described elsewhere. FIG. 14I shows a nose cone assembly 274 arranged relative to the cutting assembly 500 of FIG. 14C. The longitudinal axis A of the distal shaft 210 of the nose cone assembly 274 can be aligned with the terminal region 508 of the slot 507 so that the compacting tool 517 can urge the cut stent 105 into the shaft 210. Once the cut stent 105 is compacted into the lumen 238 of the shaft 210 the nose cone assembly 274 can be removed from its association with the cutting assembly 500 and transferred to a delivery device 400 for deployment in the eye.

The position of the movable stop 520 relative to the cutting blade of the die 511 can be adjusted to achieve different stent widths. For example, the movable stop 520 can be moved toward the single blade of the cutting die 511 to decrease the width of the stent and moved away from the cutting die 511 to increase the width of the stent. The location of the movable stop 520 relative to the cutting die 511 can be selected by a user, for example, via a dial or other user interface that allows for incremental adjustments. The dial range can be between about 0.6 mm and about 1.9 mm and can include markings that are laid out per a ¼ to ⅟16 thread. The cutting die 511 of the cutting assembly 500 can be attached to a lever, handle, or other actuator 343 as described elsewhere herein, to advance the single blade through the patch of material 101 held against the cutting surface 513 by the pad 515 upon selection of the width. In an implementation, the cutting surface 513 can be ⅟16" 90A silicone.

Figure 15A:
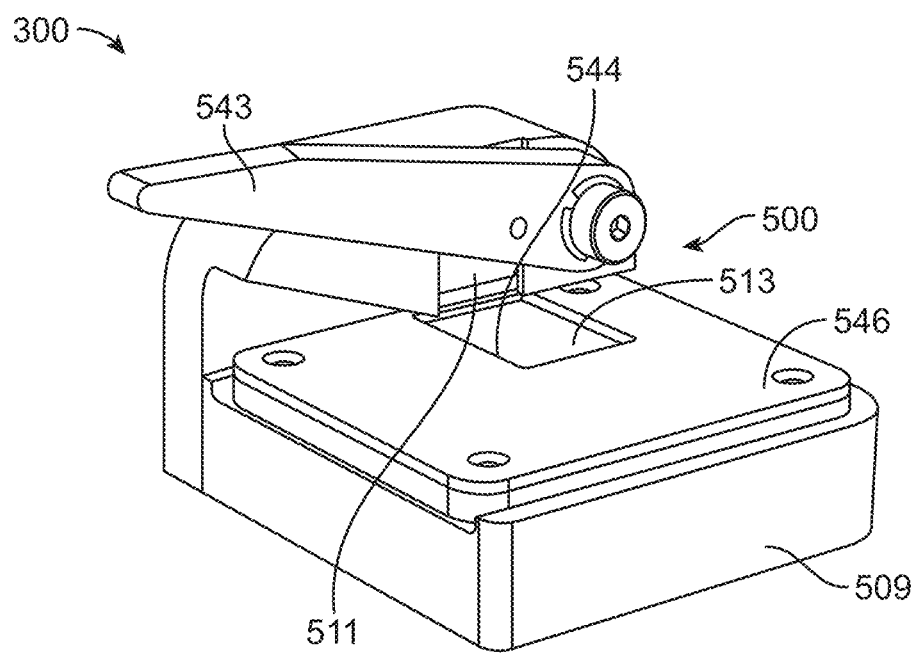
FIGS. 15A-15B illustrate another implementation of a cutting device for cutting a stent.
Figure 15B:
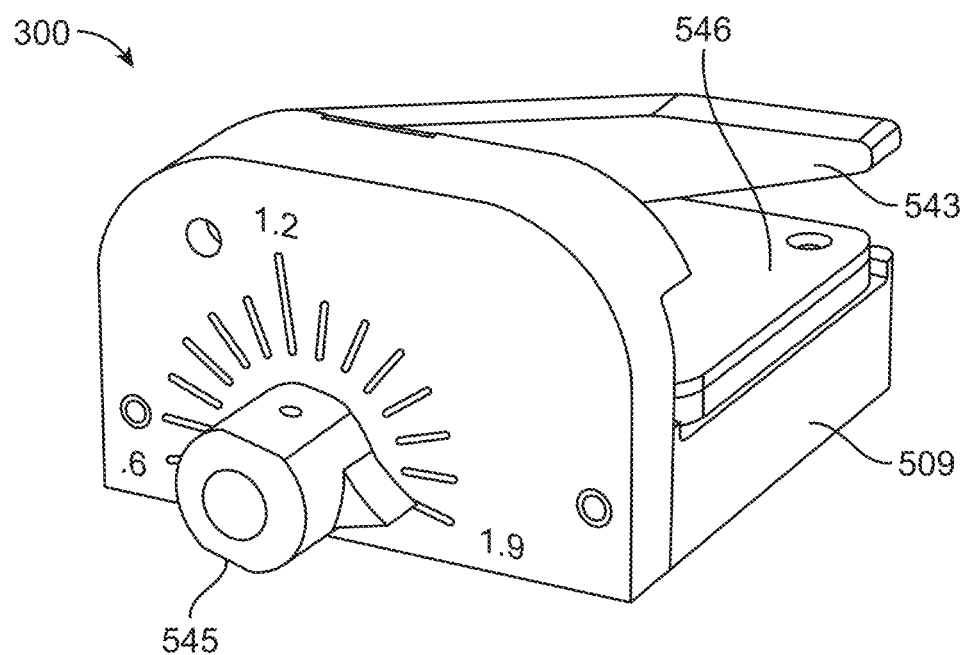

FIGS. 15A-15B illustrate a cutting device 300 having a cutting assembly 500. The cutting device 300 can include a handle 543 movably coupled to the base 509 to actuate the cutting assembly 500. For example, the handle 543 is configured to raise and lower a cutting die 511 relative to the cutting surface 513 of the base 509. The cutting surface 513 can include a recess 544 sized to hold a patch of material (not shown). The cutting surface 513 can be movable relative to the base 509 to expose the recess 544 for positioning the patch of material 101 within the recess 544. The cutting device 300 can incorporate an actuator 545 such as a dial, button, slider, switch, or other type of actuator configured to adjust the position of the blade 511 relative to the cutting surface 513 as discussed above. The actuator 545 can move the base 509 side-to-side via a threaded screw or other mechanism to change the position of the patch of material 101 held within the recess 544 relative to the cutting die 511 and thereby modify the width of the stent cut from the patch. Alternatively, the actuator 545 can move the die 511 relative to the recess 544 to change the width of the stent. The cutting device 300 can incorporate a stage 546 configured to be movable relative to the base 509 such as by sliding, swiveling, or lifting away from the base 509. In some implementations, the stage 546 can slide within a single plane relative to the underlying base 509 while remaining connected to the base 509 at least in part. Alternatively, the stage 546 can be removed entirely from the base 509. Moving the stage 546 relative to the base 509 can reveal the recess 544 out from under the area of the device where the cutting die 511 and handle 543 are located. This allows for loading of a patch within the recess 544 without the components of the cutting assembly 500 obstructing a user's view or blocking access physically. The cutting device 300 can be a solo cutter and need not incorporate a compression or holding mechanism or a transferring mechanism. Rather, the cut stent 105 following cutting with the cutting assembly 500 can be manually transferred to another tool for priming the cut stent 105 for deployment through a shaft.

Figure 14D:
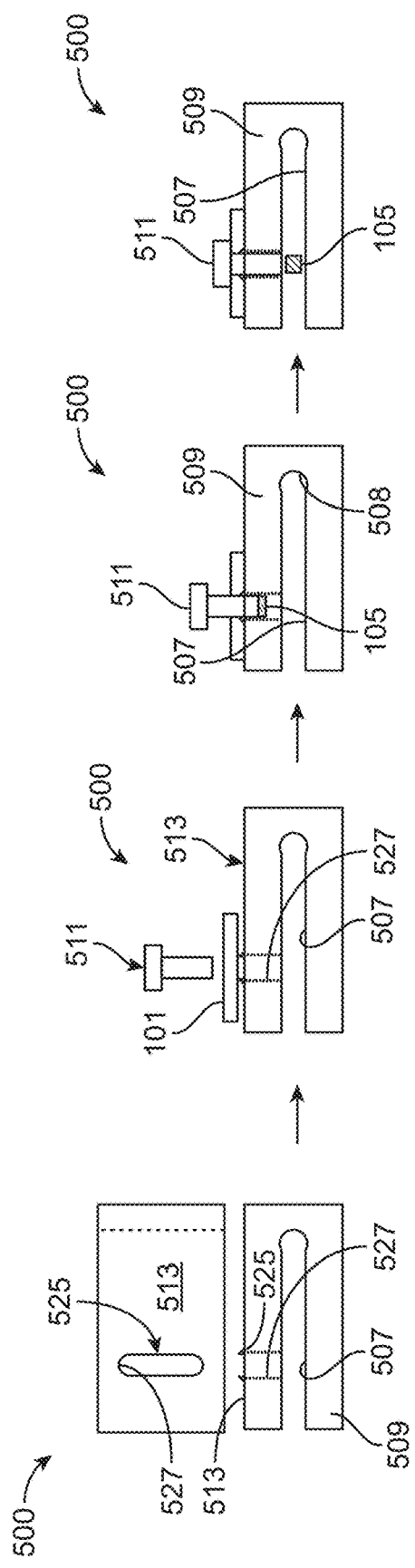

FIG. 14D shows an interrelated implementation of a cutting assembly 500 for cutting the patch of material 101. The cutting assembly 500 can include a paper hole punch sort of cutting. Sharp corners or raised sharp edges 525 can project from the cutting surface 513. The sharp edges 525 can surround a hole 527 through the cutting surface 513 that leads directly into the slot 507 of the base 509. A patch of material 101 can be positioned against the cutting surface 513 over the hole 527 and against the sharp edges 525. A punch 511 can be urged against the patch of material 101 from above so that the patch of material 101 is cut by the sharp edges 525 and the cut stent 105 is urged through the hole 527 into the slot 507 by the punch 511. The cut stent 105 can then be arranged within the slot 507 so that a pusher (not shown in FIG. 14D) may urge the cut stent 105 through the slot 507 towards the terminal end 508. The terminal region 508 of the slot 507 aligns the cut stent 105 with the longitudinal axis A of the distal shaft 210 so that the stent can be urged into the distal shaft 210 so that it is primed for delivery. The cartridge can be removed from the cutting device 300 and transferred to a delivery device 400 for deployment in the eye.

Figure 14E:
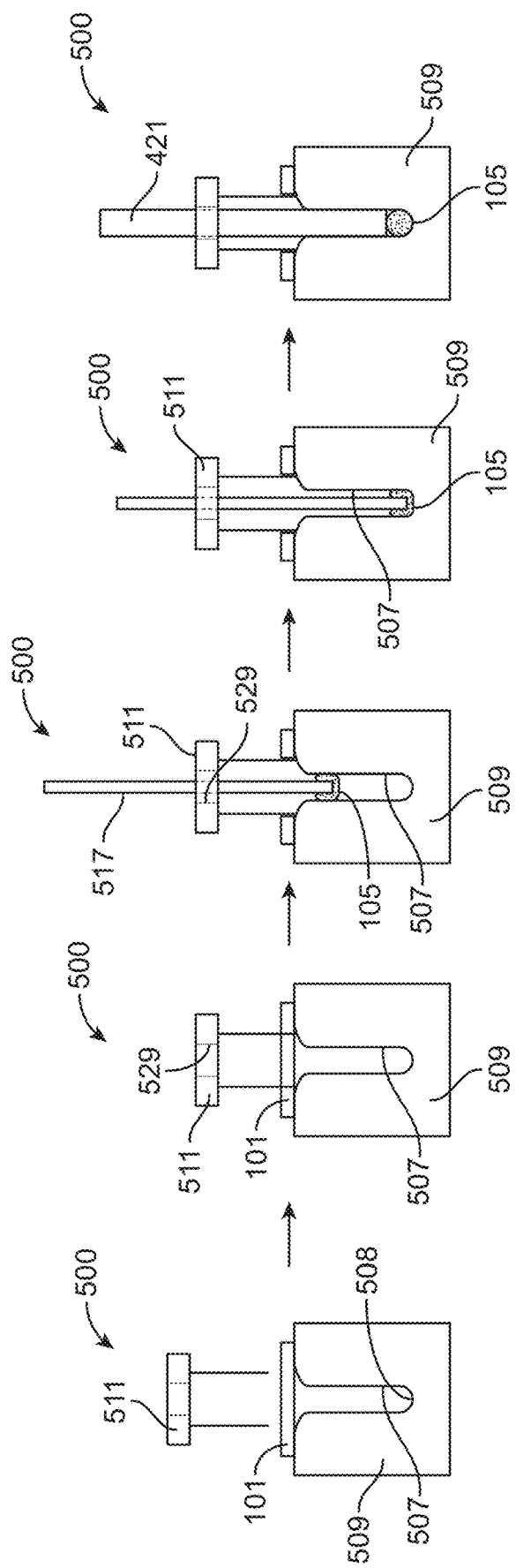

FIG. 14E shows an interrelated implementation of a cutting assembly 500 for cutting the patch of material 101. The cutting assembly 500 can also incorporate a money plunger sort of cutting. The patch of material 101 can be positioned over a slot 507 in a base 509 and a cutting die 511 urged from above against the material 101 so that the cutting edges of the die 511 can slice through the patch of material 101 in two locations to cut the stent 105 to length. A compacting tool 517 can be advanced through a bore 529 in the die 511 to drive the cut stent 105 into the slot 507 urging it to a terminal region 508 of the slot 507. The compacting tool 517 or an additional compression tool 421 can be advanced through the bore 529 in the die 511 to compress the cut stent 105 within the terminal region 508 of the slot 507 to compact it and align the cut stent 105 with the distal shaft 210 so that it is primed for delivery. The cartridge can be removed from the cutting device 300 and transferred to a delivery device 400 for deployment in the eye.

FIG. 14F shows an interrelated implementation of a cutting assembly 500 for cutting the patch of material 101. The cutting assembly 500 can incorporate forceps-like tool 530 to clamp the patch of material 101. A scalpel or other cutting tool 535 can be used to trim the patch of material 101 held by the forceps 530 to length. The forceps 530 holding the cut stent 105 can be arranged relative to a base 509 and the clamp pressure of the forceps 530 released. A compacting tool 517 can be advanced through the forceps 530 to urge the cut stent 105 from the forceps 530 into a slot 507 of the base 509 for compressing and compacting the cut stent 105 for delivery as described above.

FIG. 14G shows an interrelated implementation of a cutting assembly 500 for cutting the patch of material 101. The cutting assembly 500 can incorporate a plunger 511 configured to compress a patch of material 101 within a transfer slot 537 of a transfer base 539. The patch of material 101 can be trimmed to size with a scalpel or other cutting tool 535. The cut stent 105 within the transfer slot 537 can be transferred by attaching to the transfer base 539 to a base 509 with a defined slot 507 in a manner that aligns transfer slot 537 to slot 507 for compressing and loading of the cut stent 105 using a compacting tool 517 for deployment.

Figure 14H:
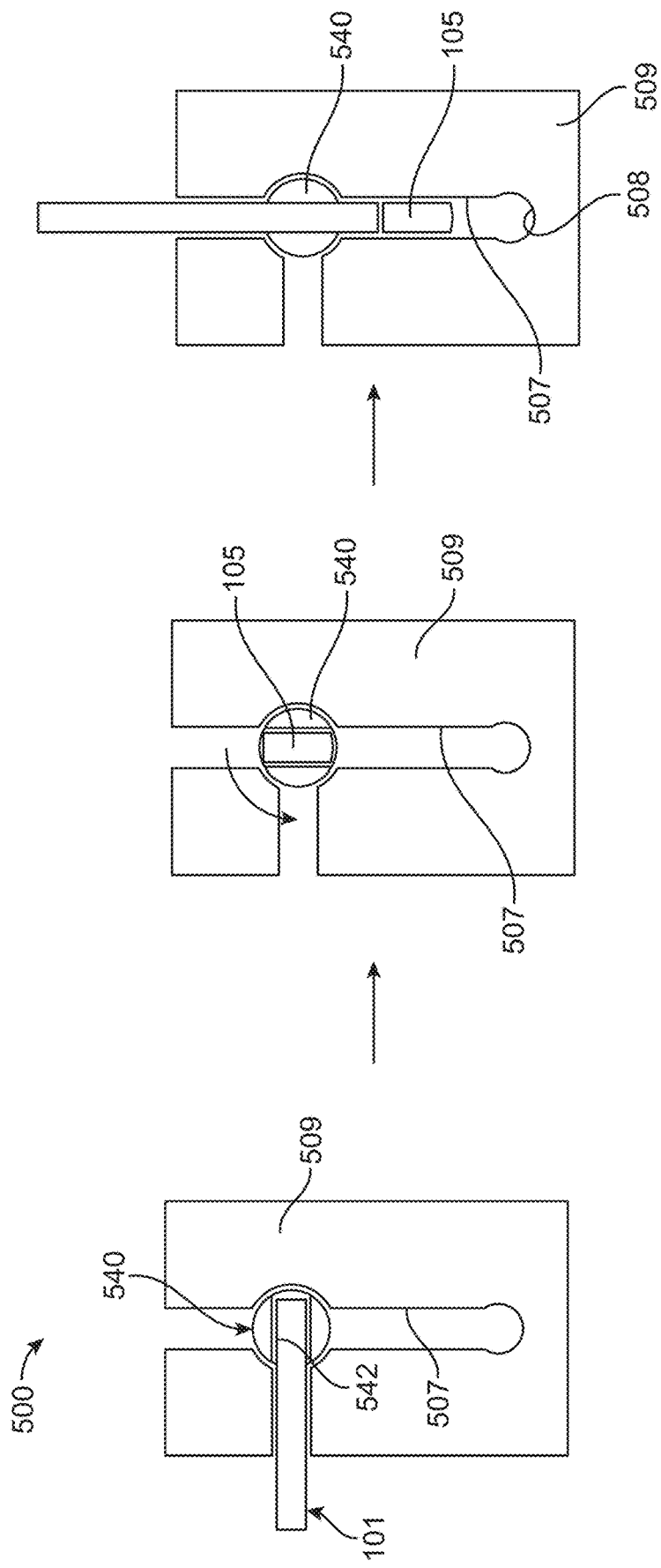
Figure 14I:
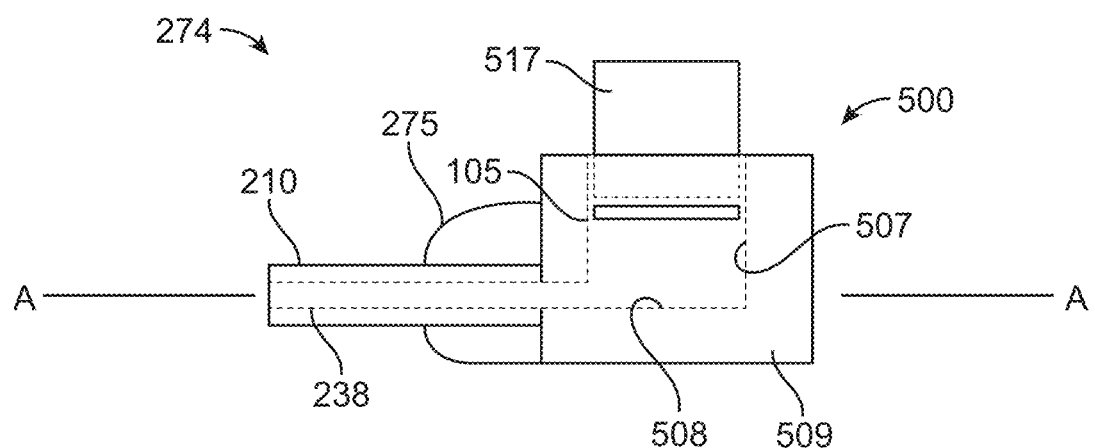
FIG. 14I illustrates in schematic an implementation of a nose cone assembly coupled to a cutting assembly.

FIG. 14H shows an interrelated implementation of a cutting assembly 500 for cutting the patch of material 101. The cutting assembly 500 can incorporate a rotating cylinder 540 configured to cut and arrange the cut stent 105 relative to a slot 507 in a base 509 for loading and compressing the stent 105 for delivery. The rotating cylinder 540 can incorporate an internal slot 542 for receiving at least a portion of the patch of material 101. Rotation of the cylinder 540 trims the excess tissue extending beyond the slot 542 in the cylinder 540. The cut stent 105 trimmed to length within the slot 542 of the cylinder 540 is then arranged relative to the slot 507 in the base 509 for loading and compression for delivery.

The cut stent 105 that is loaded and compressed for delivery can be positioned within at least a portion of the cartridge 200, such as within a lumen 238 of the shaft 210. At least a portion of the cartridge 200 can be removed from the cutting device 300 and engaged with a delivery device 400 for deployment of the stent 105 from the cartridge 200 into the eye. The compression and transfer of the cut stent 105 described above in relation to the cutting assembly 500 prepares the cut stent 105 for delivery without the cut stent 105 being removed from the cartridge 200.

The cartridge 200 is described herein as being configured to couple with a cutting device 300 having a cutting assembly 500 for cutting a patch of material 101 and then removed from engagement with the cutting device 300 so that it can be coupled to a delivery device 400. This relationship can include removing and re-engaging the entire cartridge 200 or just a portion of the cartridge 200, such as just the nose cone assembly 274 (e.g., the nose cone 275 and the shaft 210). Both arrangements are considered herein. The nose cone assembly 274 may be referred to herein simply as the cartridge 200. Where the cartridge 200 is described as removed from the cutting device 300 the description is relevant to just the nose cone assembly 274 being removed or the entire cartridge 200 being removed from the cutting device 300. Where the cartridge 200 is described as configured to engage with the delivery device 400 that the description is relevant to just the nose cone assembly 274 being engaged or the entire cartridge 200 being engaged to the delivery device 400. Each instance of coupling between the cartridge 200 and another component of the system 100 may be the entire cartridge 200 or just a portion of the cartridge 200 such as the nose cone assembly 274.

The patch of material 101 can be placed within a portion of the cartridge 200 for cutting or the patch of material 101 can be placed within a portion of the cutting device 300 for cutting by the cutting assembly 500 and the cut stent 105 transferred to the cartridge 200 (or just a portion of the cartridge 200 such as the nose cone assembly 274). The cut stent 105 can be transferred using a component of the cutting assembly 500 into the cartridge 200, which is then decoupled from the cutting device for coupling with the delivery device. The patch of material 101 can be placed within a region of the cutting assembly 500 for cutting and then the cut stent 105 manually transferred from the cutting assembly 500 for compacting within a delivery shaft 210. The cut stent 105 can be transferred using a separate device from the cutting assembly 500 including manually. In an implementation, the system includes a cutting device 300 having a cutting assembly 500. The cut stent 105 from the cutting assembly 500 can be manually transferred (e.g., by forceps) to a transfer device having a compacting tool 517 to compact the cut stent 105 into a distal shaft 210. The distal shaft 210 having the cut stent 105 compacted therein can then be coupled to a delivery device 400 for deployment of the cut stent 105 in an eye. The system can have separate cutting, transferring, and delivery devices rather than one or more of the devices being integrated. The cutting assemblies 500 shown in FIGS. 14A-14H can be part of a cutting device. The transferring components of the cutting assemblies 500 can be integrated with the cutting device or can be a separate transferring device.

The system 100 can include a delivery device 400 that is configured to couple with at least a portion of the cartridge 200 holding the cut stent 105. In some implementations, the entire cartridge 200 with the cut stent 105 is removed from the cutting device 300 and engaged with the delivery device 400 (see FIG. 2). In interrelated implementations, a portion of the cartridge 200 with the cut stent 105 positioned therein is removed from the cutting device 300 and engaged with the delivery device 400 (see FIGS. 6, 9A-9D).

In the implementation shown in FIGS. 5A-5B, the cartridge 200 holding the cut stent 105 can be removed loaded into the delivery device 400. FIGS. 5C-5F illustrate loading of the tissue cartridge 200 within the delivery device 400 and deployment of the cut stent 105 using the delivery device 400. The delivery device 400 together with the cartridge 200 can be used to deliver the stent 105 into the implanted location, such as via an ab interno delivery pathway. This allows for loading the stent and deploying the stent without having to remove the cut stent 105 from its location within the cartridge 200 in order to load the cut stent 105 into the delivery device 400. At least a portion of the cartridge 200 (e.g., the proximal portion 207 of the cartridge 200 or a region of the nose cone assembly 274) can be held by the delivery device 400 and the distal portion 205 of the cartridge 200 can be inserted into the eye.

The delivery device 400 can include a proximal handle 405 that is sized and shaped to be grasped by a single hand of a user and a distal end region 410 defining an attachment mechanism 425 such as a receptacle 412 sized to engage with at least a portion of the cartridge 200. In an implementation, the receptacle 412 can be sized to receive at least a length of the proximal portion 207 of the cartridge 200 (see FIG. 5C). In an interrelated implementation, the attachment mechanism 425 can incorporate another male-to-female attachment mechanism such as a bayonet connection 413 (see FIGS. 10A-10C). As mentioned above with respect to the cutting device 300, the attachment mechanism 425 can be keyed such that the cartridge 200 with the cover 214 in place on the base 224 can be received within or otherwise engage the attachment mechanism 425 in a single orientation. When the cartridge 200 is coupled with the attachment mechanism 425 of the handle 405, the shaft 210 of the cartridge 200 extends in a distal direction outward from the handle 405. The keying features of the attachment mechanism 425 can prevent attachment in the wrong orientation. The attachment mechanism 425 can also provide a secure connection with tactile feedback to the user to indicate when the connection is fully engaged. The attachment mechanism 425 also is dimensioned to ensure alignment of the lumen 238 of the shaft 210 with the internal mechanisms of the delivery device 400 such as the push rod 420.

Figure 5C:
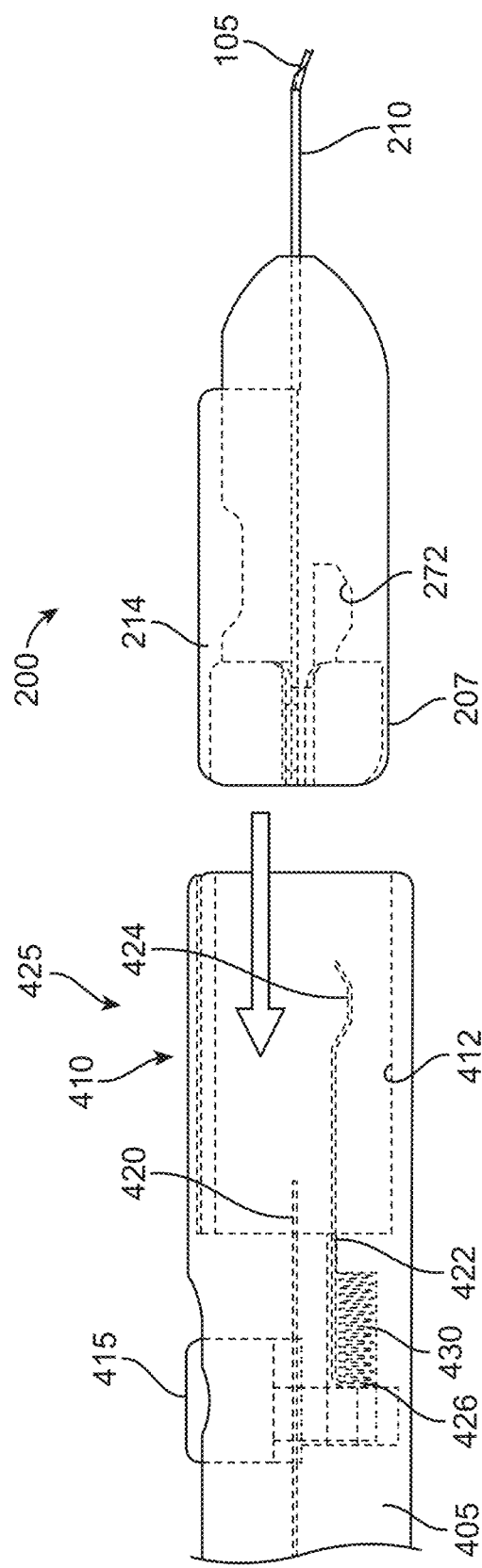
FIG. 5C illustrates the tissue cartridge and distal end region of the delivery device.

The attachment mechanism 425 of FIGS. 5A-5C can be a receptacle 412 having a depth sufficient to contain a length of the proximal portion 207 of the cartridge 200 while the shaft 210 remains outside the receptacle 412. A flexible hook 422 can extend into at least a portion of the receptacle 412 (see FIG. 5C). A distal end 424 of the hook 422 can be received within a correspondingly shaped detent 272 near a proximal end region of the tissue cartridge 200. As the cartridge 200 slides within the receptacle 412, the distal end 424 of the hook 422 can slide through the proximal end 207 of the cartridge 200 and insert within the detent 272. The flexibility of the hook 422 allows for the hook 422 to be urged upward as the distal end 424 of the hook 422 is advanced through a first region of the cartridge 200 and flex back downward as the distal end 424 is advanced further to thereby engage the detent 272 (see FIG. 5D). The spring-loaded hook 422 engaging with the detent 272 can provide a tactile and/or auditory "click" to inform a user that the cartridge 200 is fully installed within the delivery device 400, retained and ready for delivery of the stent 105.

One or more actuators 415 can be positioned on a region of the handle 405. The actuator 415 can also be manipulated by the single hand of the user such as with a thumb or finger. The configuration of the actuator 415 can vary. For example, the actuator 415 can include any of a variety of knob, button, slider, dial, or other type of actuator configured to move one or more components of the delivery device 400 as will be described in more detail below.

The delivery device 400 can include a compacting tool 420 configured to be moved by the one or more actuators 415. The compacting tool 420 can be used together with the cartridge 200 to deliver the stent 105 from the cartridge 200 once the desired position is reached with the distal end of the shaft 210. The compacting tool 420 can be sized and shaped complementary to the inner dimension of the shaft 210. For example, where the shaft 210 of the cartridge 200 has a rectangular cross-sectional shape, the compacting tool 420 may be rectangular in cross-section. This allows the compacting tool 420 to effectively urge the cut stent 105 through the lumen 238 of the shaft 210.

Figure 5D:
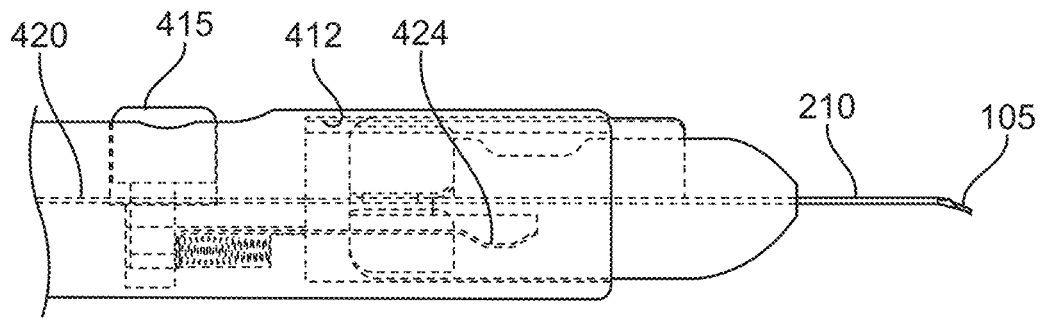
FIG. 5D illustrates the tissue cartridge installed within the delivery device of FIG. 5C.

The compacting tool 420 can be fully retracted in a proximal position prior to coupling of the tissue cartridge 200 within the delivery device 400 so the compacting tool 420 does not interfere with loading of the cartridge 200. Once the cartridge 200 is installed and retained within the delivery device 400 as shown in FIG. 5D and FIG. 9B, the compacting tool 420 can be advanced distally through a proximal port in the cartridge 200 and into the lumen 238 of the shaft 210 (see FIG. 5E and FIG. 9C). In some implementations, the compacting tool 420 can be advanced through the lumen 238 and out the distal opening 230 from the lumen 238 to deploy the stent 105. In other implementations, the compacting tool 420 is advanced to a distal location near the proximal end of the stent 105 within the lumen 238 and the shaft 210 is withdrawn proximally while the compacting tool 420 remains stationary to deploy the stent 105 (see FIG. 5F and FIG. 9D).

Figure 5E:
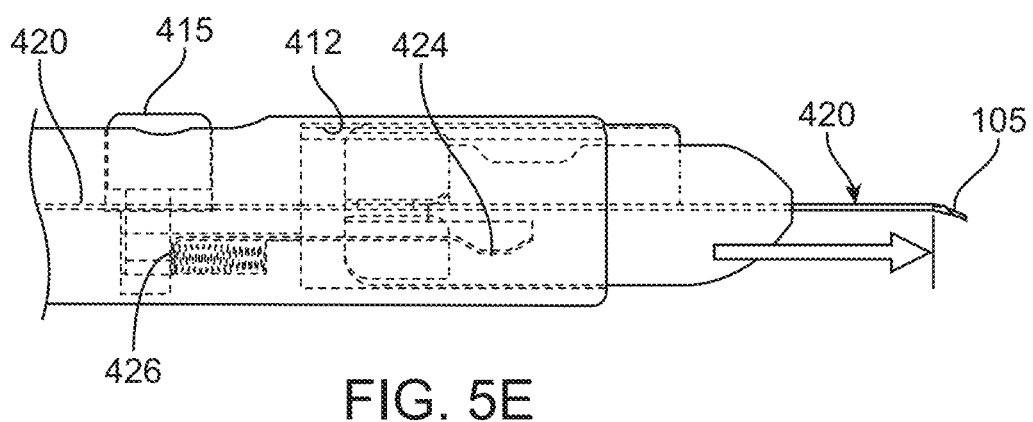
FIG. 5E illustrates the pusher of the delivery device advanced to deployment position.
Figure 5F:
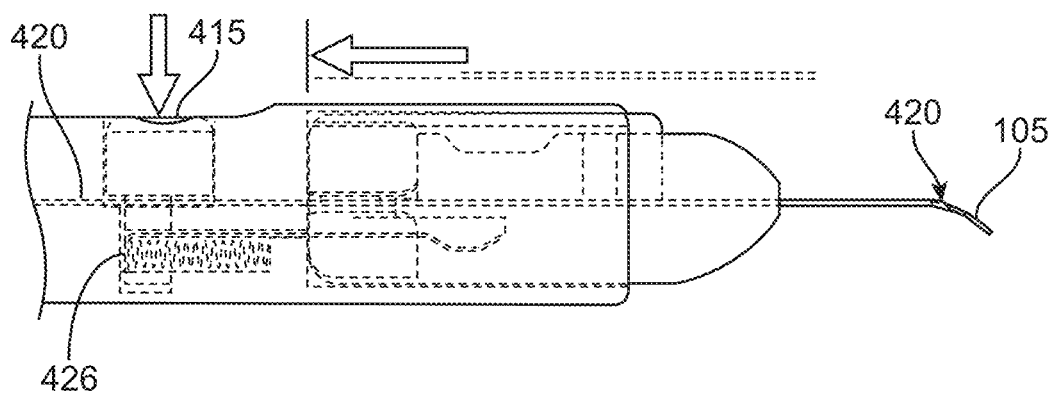
FIG. 5F illustrates the tissue cartridge retracted by the delivery device to deploy the cut stent within the eye.

The shaft 210 can be withdrawn proximally via motion of the cartridge 200 in a proximal direction relative to the delivery device 400 while the compacting tool 420 remains stationary in order to deploy the stent 105 within the eye (see FIG. 5F and FIG. 9D). The compacting tool 420 therefore can act as a stopper thereby preventing the stent 105 from following the shaft 210 as it is retracted. The result is that the stent 105 is unsheathed from the shaft 210 and left within the tissues. In other implementations, both the cartridge 200 and the compacting tool 420 are movable to effect deployment of the stent from the shaft 210.

In some implementations, the compacting tool 420 can be coupled to a first actuator 415 and the cartridge 200 can be coupled to a second actuator 415. The first and second actuators 415 can be sliders, buttons, or other configuration or combination of actuators configured to advance and retract their respective components. The first actuator 415 coupled to the compacting tool 420 can be withdrawn proximally such that the compacting tool 420 is in its most proximal position when the cartridge 200 is engaged by the attachment mechanism 425 of the delivery device 400. The user can advance the first actuator 415 to urge the compacting tool 420 distally to advance the stent 105 within the lumen 238 of the cartridge 200 towards the distal opening 230 of the shaft 210. After the cut stent 105 is primed into its distal position within the lumen 238, the shaft 210 of the cartridge 200 can be used to dissect tissue of the eye until a target location is accessed. Once the shaft 210 is in position to deploy the stent 105 in the eye, the first actuator 415 coupled to the compacting tool 420 can be maintained in this distal position and the second actuator 415 actuated (e.g., withdrawing a slider or pushing a button) to retract the cartridge 200 a distance relative to the delivery device 400. This relative movement of the shaft 210 of the cartridge 200 to the compacting tool 420 deploys the stent 105 from the lumen 238 in the anatomy.

FIG. 5E shows the cartridge 200 installed within the receptacle 412 of the delivery device 400 such that a space exists between the terminal end of the receptacle 412 and the proximal-most end of the cartridge 200. The depth of this space defines the maximum distance the cartridge 200 can be retracted. The stent 105 is located near the distal opening 230 from the lumen 238 and the compacting tool 420 is advanced to its distal position such that the distal end of the compacting tool 420 abuts against a proximal end of the stent 105. The distal end 424 of the hook 422 is retained within the detent 272 and the second actuator 415 is not yet actuated. A proximal end 426 of the hook 422 is coupled to a spring 430. When the second actuator 415 is in a resting state prior to actuation, the hook 422 is urged distally into a first configuration. The spring 430 is compressed between the proximal end 426 of the hook 422 and the distal end of the spring 430 housing when the hook 422 is urged distally into the first configuration. When the second actuator 415 is actuated (e.g., pushed downward), the spring 430 is released and urges the proximal end 426 of the hook 422 towards a proximal end of the handle 405. The hook 422 moves proximally and drags along with it the cartridge 200, which is coupled to the hook 422 due to engagement of the distal end 424 of the hook 422 within the detent 272. The distance the hook 422 moves proximally thus, retracts the cartridge 200 deeper into the receptacle 412. The compacting tool 420 can remain stationary during cartridge 200 retraction. The relative motion between the shaft 210 and the compacting tool 420 deploys the stent 105 from the lumen 238 (see FIG. 5F).

It should be appreciated that additional distal movement of the compacting tool 420 can be used to aid in deployment of the stent 105 from the lumen 238. It should also be appreciated that compacting tool 420 advancement and cartridge 200 retraction can be controlled by dual actuators 415 as described above or by a single actuator 415 capable of both pusher and cartridge 200 movement depending on degree of actuation. Additionally, the shaft 210 can be used to inject a viscous material such as viscoelastic during the procedure using the compacting tool 420 as a plunger. The methods of implantation and delivery of the stent 105 are described in more detail below.

Figure 11A:
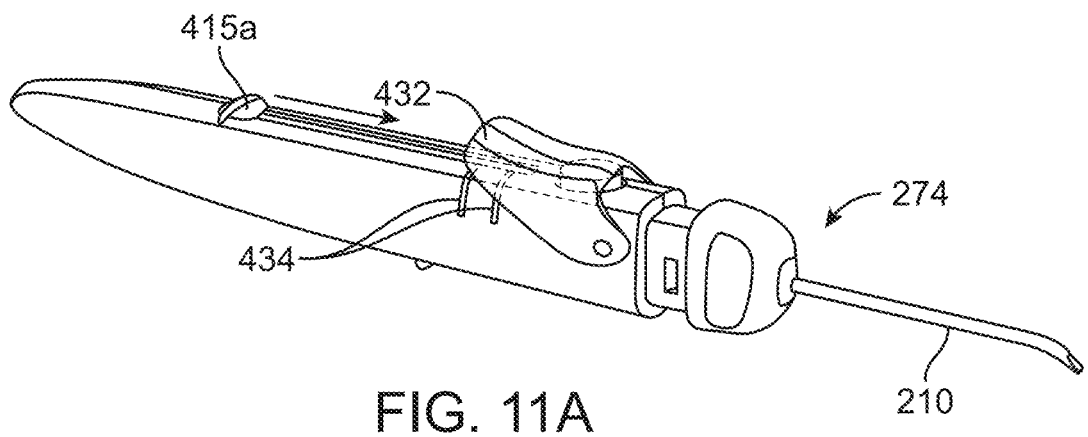
FIG. 11A illustrates the pusher in the first, retracted position.
Figure 11B:
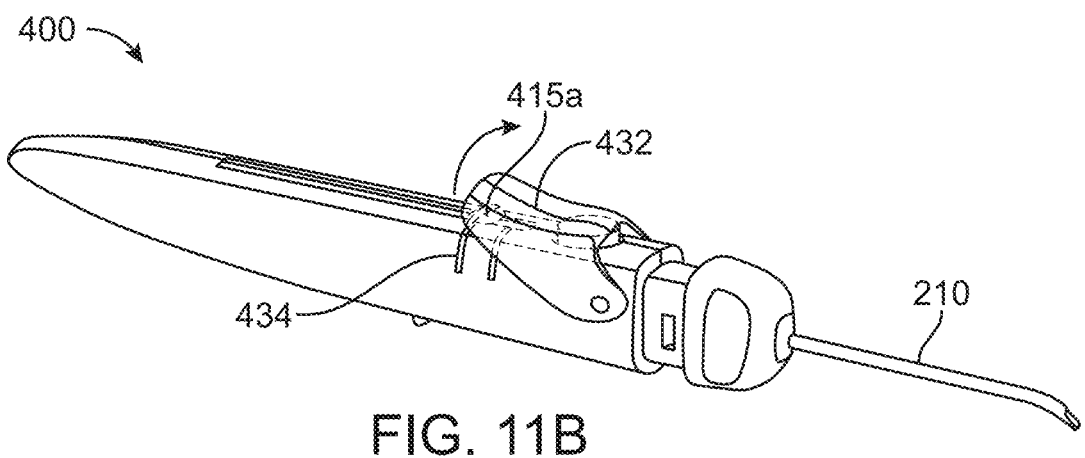
FIG. 11B illustrates the pusher advanced to the second, primed position.
Figure 11C:
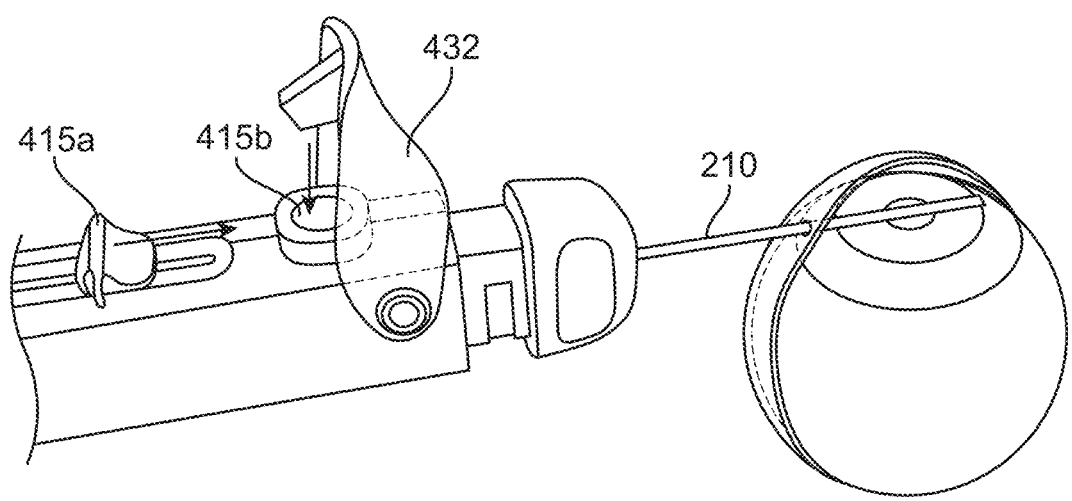
FIG. 11C shows the distal shaft positioned within the eye and the third actuator ready to be activated.
Figures 12A, 12B, 12C, 12D:
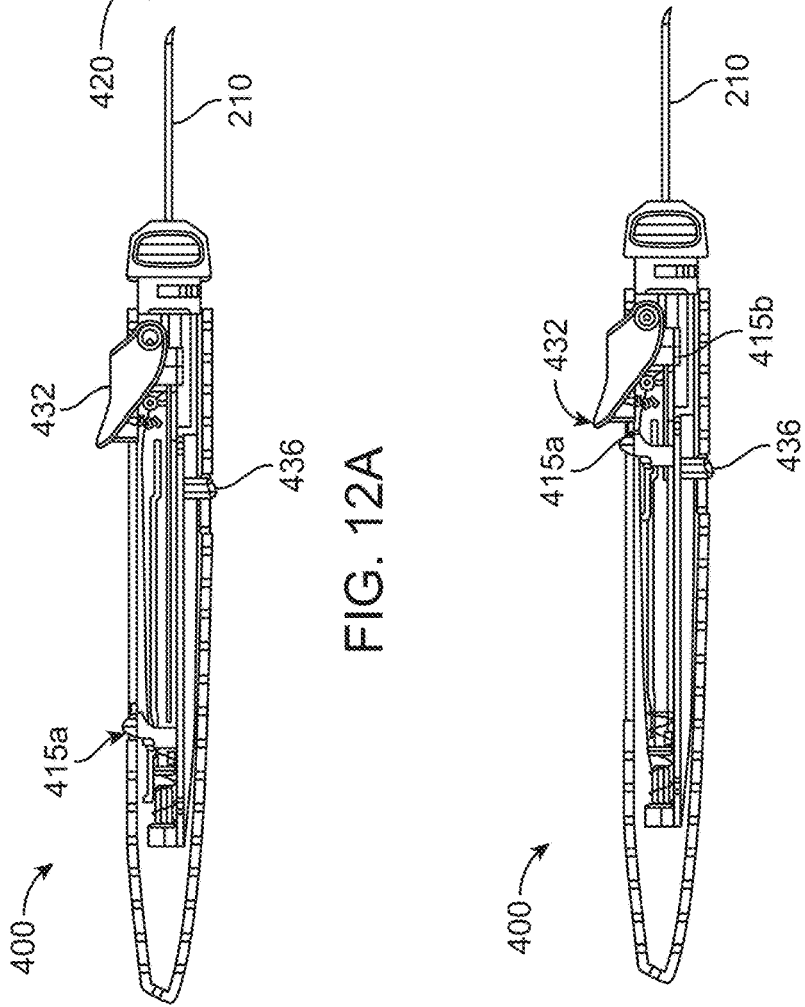
FIGS. 12A-12B are cross-sectional views of the device showing the first, retracted position of FIG. 11A.
FIGS. 12C-12D are cross-sectional views of the device showing the second, primed position of FIG. 11B.

FIGS. 11A-11C illustrate steps in the deployment of the stent using a first actuator 415a, which in this case can be a slider, of the delivery device 400 to move the pusher from a first loading position (fully retracted) to a second primed position (at least partially advanced). The first loading position retracts the pusher away from the distal end region of the delivery device 400 allowing the nose cone assembly 274 (or entire cartridge 200) to be coupled to the delivery device 400. The second, primed position advances the pusher towards the distal end of the delivery device 400 to advance the cut stent 105 through the lumen 238 of the shaft 210. Preferably, the pusher is advanced to the second, primed position prior to insertion of the shaft 210 through the cornea. The delivery device 400 can additionally incorporate a movable guard 432 arranged to prevent a user from inadvertently pushing the slider beyond the second primed position. The guard 432 can be pushed down toward the housing of the delivery device so that a second actuator 415b is covered by the guard 432 preventing the second actuator 415b from being inadvertently activated. The guard 432 has a length so that the guard 432 extends over at least a portion of the slider track thereby blocking the first actuator 415a from moving further distal in addition to blocking the second actuator 415b (FIG. 11B). Once the stent 105 is advanced to the primed position and is ready to be deployed in the eye, the guard 432 can be rotated up out of the way revealing the second actuator 415b. The first actuator 415a is free to slide further distal along the track and the second actuator 415b is available to be depressed (FIG. 11C). The guard 432 can also be fully removed from the device 400 or the device 400 not include any guard 432. The housing of the device 400 can include one or more marks 434 intended to provide feedback to a user regarding the position of the compacting tool 420 through the shaft 210. The advancement of the compacting tool 420 into one or more positions relative to the housing can also provide tactile feedback to a user as described elsewhere herein.

FIGS. 12A-12D illustrate the delivery device 400 in cross-section prior to advancing the pusher rod 420 to the second position and after advancing the pusher rode 420 to the second position. Once the nose cone assembly 274 is attached to the delivery device 400, the first actuator 415 and the compacting tool 420 can be advanced from the initial, retracted first position to a second position. The first actuator 415a and the compacting tool 420 can be advanced to the second position causing the compacting tool 420 to insert into the lumen 238 behind the material to be delivered (e.g. cut stent 105). The guard 432 can prevent the first actuator 415a from sliding beyond the second position. The location of the second position is designed to place the leading face of the compacting tool 420 a predefined distance away from the distal tip of the shaft 210 (e.g. 6 mm). Once the user has created the desired cleft and are ready to deliver material from the lumen, the compacting tool 420 can be advanced to its third, forward-most position (with the guard 432 out of the way or otherwise removed or absent from the device 400). The second actuator 415b can be engaged to release the material from the shaft 210. The second actuator 415b as described elsewhere herein can retract the shaft 210 while the compacting tool 420 remains fixed ultimately releasing the stent 105 from the lumen. The nose cone assembly 274 withdraws and the compacting tool 420 stays fixed.

Figure 13A:
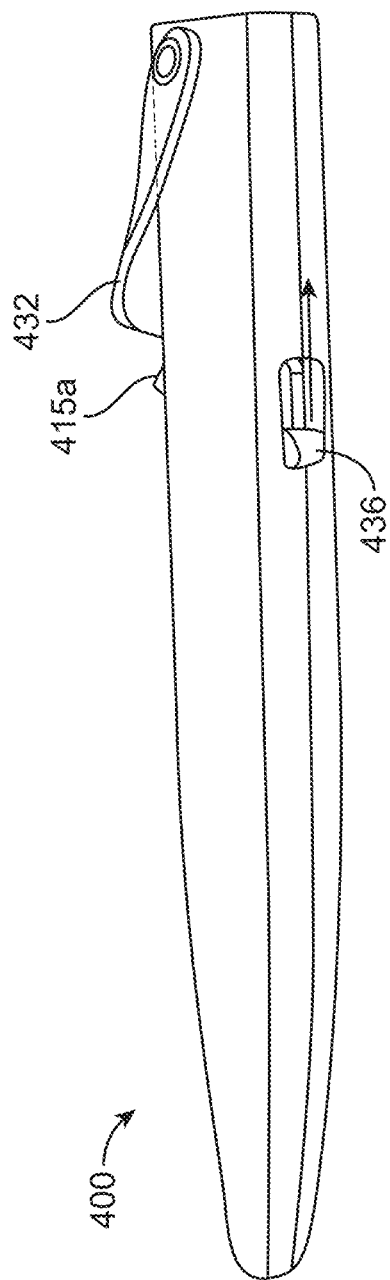
FIGS. 13A-13B illustrate a reset mechanism of the delivery device.
Figure 13B:
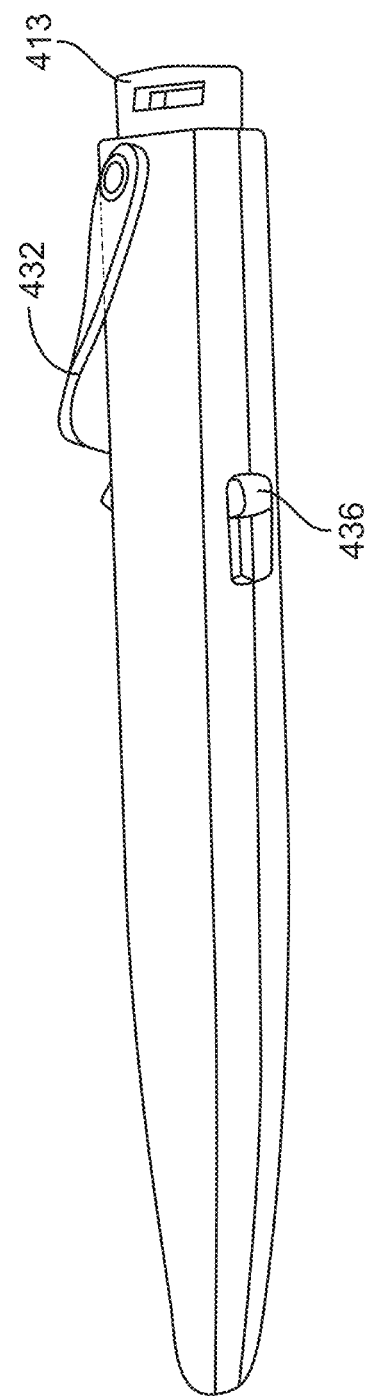

The delivery device 400 and the cartridge 200 (or nose cone assembly 274) can be single use devices or may be sterilized and re-used. FIGS. 13A-13B illustrate a reset mechanism 436 so that the deployment structures can be reset and the delivery device 400 may be re-used. Activating the reset mechanism 436, for example sliding a button forward, can return the deployment structures to an armed position. The reset mechanism 436 may also be performed by pulling on the nose cone assembly 274 or the bayonette connector 413 of the delivery device 400 distally until the second actuator 415 returns to its original armed position. The nose cone assembly 274 can be removed from the delivery device 400, if desired, and additional material loaded into the shaft 210 as described elsewhere herein. The delivery device 400 may be provided in an actuated or unarmed state and a user arm the instrument at the time of use.

A nose cone assembly transferable between the delivery device and the cutting device can be mounted relative to a main assembly of the cutting device. A patch of tissue can be cut by the cutting device and loaded into the nose cone assembly, which in turn, can be transferred from the main assembly of the cutting device back to being coupled with the delivery device for use in deployment in a patient. The configuration of the nose cone assembly can vary including any of the transferrable cartridges described herein. In an implementation, the nose cone assembly may be mounted relative to a cutting assembly by coupling a proximal end of the nose cone to the base such that a longitudinal axis of the lumen of the shaft extending distally from the nose cone aligns with a longitudinal axis of a corresponding conduit out from the slot. A tissue patch can be placed within a loading zone area of the base relative to a movable stopper plate on the main assembly. The loading zone area and movable stopper plate may both be part of the base of the main assembly. The patch can be laid inside of one or more alignment features of the loading zone and slid forward into a cutting zone until the patch abuts the stopper plate. Once positioned against the stopper plate, the tissue patch is positioned a specified width by the cutter. Thus, the stopper plate provides a calibrated stopping point for the tissue patch prior to cutting. An element designed to fix the tissue patch in this position can be activated such as being lowered down over the tissue patch to hold the tissue in place and optionally compress the tissue to a specific height prior to cutting. Once this holding plate is lowered down onto the patch to hold it in place, the cutting lever can be lowered to cut the tissue patch with one or more blades. The stopper plate and holding plate can be moved away from the cut stent and the remainder of the tissue patch removed from the assembly. The cut stent can be loaded using a tissue loader slider. The tissue loader slider can urge the cut stent into position relative to the longitudinal axis of the shaft in the nose cone assembly. For example, the tissue loader slider can be put into place and slid as far forward as possible until the slider abuts a ledge on the main assembly indicating that the cut stent has been fully delivered into the compression channel and is ready to be advanced into the shaft of the nose cone assembly. An elongate tool such as a tissue advancer rod can be inserted into the main assembly along the longitudinal axis to urge the cut stent from the main assembly into the shaft of the nose cone assembly. The rod can be designed to advance the tissue slide towards the tip of the nose cone assembly without pushing the cut stent entirely out of the lumen of the shaft. The nose cone assembly can then be disconnected from the main assembly and attached to a delivery device for deployment into a patient.

In other implementations the cartridge 200 itself holds the patch of tissue for cutting. For example, FIG. 3A shows the cover 214 of the cartridge 200 can be removed from the slot 214 in the base 224 revealing the recess 221. A patch of material 101 may be manually loaded within the recess 221. The patch of material 101 may be sized to be received within the recess 221 or may be trimmed to ensure it is sized to be received within the recess 221. The cover 214 of the cartridge 200 is replaced onto the base 224 and advanced through the slot 215 until the lower portion 222 of the cover 214 engages the patch of material 101 trapping it against the projection 271. The cover 214 can compress and/or tension the patch of material 101 within the cartridge 200 when in the closed configuration. FIG. 2 shows the loaded tissue cartridge 200 can be installed into the receptacle 306 of the cutting device 300 with the handles 343 in the open configuration. Once installed, the cutting member 312 can be actuated by lowering the handles 343 towards the base 302 thereby urging the blades 344 towards the patch of material 101 until the blades 344 of the cutting member 312 fully slice through the patch of material 101 (FIG. 4B). With the blades 344 still in the full cut position relative to the cartridge 200, the pusher 320 of the cutting device 300 can be urged distally to prime the shaft 210 and place the now cut stent 105 within the lumen 238 of the shaft 210 towards the opening 230 from the lumen 238 near the distal end region 212 of the shaft 210. The pusher 320 can be retracted from the cartridge 200 and the cartridge 200 removed from the cutting device 300. As described elsewhere herein, removal of the cartridge 200 from the cutting device 300 can include removing the entire cartridge 200 from the device 300 or detaching a nose cone assembly 274 of the cartridge 200 as shown in FIG. 6.

The primed tissue cartridge 200 having the cut stent 105 positioned within the lumen 238 of the shaft 210 can be installed with the delivery device 400 (e.g., inserted within the receptacle 412 or attached by a bayonet connector 413 or other attachment mechanism 425). The compacting tool 420 of the delivery device 400 is withdrawn in the proximal-most position and the cartridge 200 coupled to the delivery device 400. The compacting tool 420 can be advanced using a first actuator 415 from the first, retracted position suitable for loading the cartridge 200 to a second primed position so that the delivery device 400 and cartridge 200 are now ready to be used on a patient.

In general, the stent 105 positioned within the shaft 210 can be implanted through a clear corneal or scleral incision that is formed using the shaft 210 or a device separate from the cartridge 200. A viewing lens such as a gonioscopy lens can be positioned adjacent the cornea. The viewing lens enables viewing of internal regions of the eye, such as the scleral spur and scleral junction, from a location in front of the eye. The viewing lens may optionally include one or more guide channels sized to receive the shaft 210. An endoscope can also be used during delivery to aid in visualization. Ultrasonic guidance can be used as well using high-resolution bio-microscopy, OCT, and the like. Alternatively, a small endoscope can be inserted through another limbal incision in the eye to image the eye during implantation.

The distal tip 216 of the shaft 210 can penetrate through the cornea (or sclera) to access the anterior chamber. In this regard, the single incision can be made in the eye, such as within the limbus of the cornea. In an embodiment, the incision is very close to the limbus, such as either at the level of the limbus or within 2 mm of the limbus in the clear cornea. The shaft 210 can be used to make the incision or a separate cutting device can be used. For example, a knife-tipped device or diamond knife can be used initially to enter the cornea. A second device with a spatula tip can then be advanced over the knife tip wherein the plane of the spatula is positioned to coincide with the dissection plane. The spatula tip device can be the shaft 210.

The corneal incision can have a size that is sufficient to permit passage of the shaft 210. In an embodiment, the incision is about 1 mm in size. In another embodiment, the incision is no greater than about 2.85 mm in size. In another embodiment, the incision is no greater than about 2.85 mm and is greater than about 1.5 mm. It has been observed that an incision of up to 2.85 mm is a self-sealing incision.

After insertion through the incision, the shaft 210 can be advanced into the anterior chamber along a pathway that enables the stent 105 to be delivered from the anterior chamber into the target location, such as the supraciliary or suprachoroidal space. With the shaft positioned for approach, the shaft 210 can be advanced further into the eye such that the distal-most tip 216 of the shaft 210 penetrates the tissue at the angle of the eye, for example, the iris root or a region of the ciliary body or the iris root part of the ciliary body near its tissue border with the scleral spur.

The scleral spur is an anatomic landmark on the wall of the angle of the eye. The scleral spur is above the level of the iris but below the level of the trabecular meshwork. In some eyes, the scleral spur can be masked by the lower band of the pigmented trabecular meshwork and be directly behind it. The shaft 210 can travel along a pathway that is toward the angle of the eye and the scleral spur such that the shaft 210 passes near the scleral spur on the way to the supraciliary space, but does not necessarily penetrate the scleral spur during delivery. Rather, the shaft 210 can abut the scleral spur and move downward to dissect the tissue boundary between the sclera and the ciliary body, the dissection entry point starting just below the scleral spur near the iris root or the iris root portion of the ciliary body. In another embodiment, the delivery pathway of the implant intersects the scleral spur.

The shaft 210 can approach the angle of the eye from the same side of the anterior chamber as the deployment location such that the shaft 210 does not have to be advanced across the iris. Alternately, the shaft 210 can approach the angle of the eye from across the anterior chamber AC such that the shaft 210 is advanced across the iris and/or the anterior chamber toward the opposite angle of the eye. The shaft 210 can approach the angle of the eye along a variety of pathways. The shaft 210 does not necessarily cross over the eye and does not intersect the center axis of the eye. In other words, the corneal incision and the location where the stent 105 is implanted at the angle of the eye can be in the same quadrant when viewed looking toward the eye along the optical axis. Also, the pathway of the stent 105 from the corneal incision to the angle of the eye ought not to pass through the centerline of the eye to avoid interfering with the pupil.

The shaft 210 can be continuously advanced into the eye, for example approximately 6 mm. The dissection plane of the shaft 210 can follow the curve of the inner scleral wall such that the stent 105 mounted in the shaft, for example after penetrating the iris root or the iris root portion of the ciliary body CB, can bluntly dissect the boundary between tissue layers of the scleral spur and the ciliary body CB such that a distal region of the stent 105 extends through the supraciliary space and then, further on, is positioned between the tissue boundaries of the sclera and the choroid forming the suprachoroidal space.

Once properly positioned, the stent 105 can be released from the shaft 210. In some implementations, the stent 105 can be released by withdrawing the shaft 210 while the compacting tool 420 prevents the stent 105 from withdrawing with the shaft 210.

Once implanted, the stent 105 forms a fluid communication pathway between the anterior chamber and the target pathway (e.g., supraciliary space or suprachoroidal space). As mentioned, the stent 105 is not limited to being implanted into the suprachoroidal or supraciliary space. The stent 105 can be implanted in other locations that provide fluid communication between the anterior chamber and locations in the eye, such as Schlemm's Canal or a subconjunctival location of the eye. In another implementation, the stent 105 is implanted to form a fluid communication pathway between the anterior chamber and the Schlemm's Canal and/or communication pathway between the anterior chamber and a subconjunctival location of the eye. It should be appreciated the device described herein can also be used to deliver a stent trans-sclerally as well from an ab interno approach.

As mentioned above, the material used to form the stent can be impregnated with one or more therapeutic agents for additional treatment of an eye disease process.

A wide variety of systemic and ocular conditions such as inflammation, infection, cancerous growth, may be prevented or treated using the stents described herein. More specifically, ocular conditions such as glaucoma, proliferative vitreoretinopathy, diabetic retinopathy, uveitis, keratitis, cytomegalovirus retinitis, cystoid macular edema, herpes simplex viral and adenoviral infections can be treated or prevented.

The following classes of drugs could be delivered using the devices of the present invention: antiproliferatives, antifibrotics, anesthetics, analgesics, cell transport/mobility impending agents such as colchicine, vincristine, cytochalasin B and related compounds; antiglaucoma drugs including beta-blockers such as timolol, betaxolol, atenolol, and prostaglandin analogues such as bimatoprost, travoprost, latanoprost etc; carbonic anhydrase inhibitors such as acetazolamide, methazolamide, dichlorphenamide, diamox; and neuroprotectants such as nimodipine and related compounds. Additional examples include antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; anti-fungal agents such as fluconazole, nitrofurazone, amphotericine B, ketoconazole, and related compounds; anti-viral agents such as trifluorothymidine, acyclovir, ganciclovir, DDI, AZT, foscamet, vidarabine, trifluorouridine, idoxuridine, ribavirin, protease inhibitors and anti-cytomegalovirus agents; antiallergenics such as methapyriline; chlorpheniramine, pyrilamine and prophenpyridamine; anti-inflammatories such as hydrocortisone, dexamethasone, fluocinolone, prednisone, prednisolone, methylprednisolone, fluorometholone, betamethasone and triamcinolone; decongestants such as phenylephrine, naphazoline, and tetrahydrazoline; miotics and anti-cholinesterases such as pilocarpine, carbachol, di-isopropyl fluorophosphate, phospholine iodine, and demecarium bromide; mydriatics such as atropine sulfate, cyclopentolate, homatropine, scopolamine, tropicamide, eucatropine; sympathomimetics such as epinephrine and vasoconstrictors and vasodilators; Ranibizumab, Bevacizamab, and Triamcinolone.

Non-steroidal anti-inflammatories (NSAIDs) may also be delivered, such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (CELEBREX® from Pharmacia Corp., Peapack, N.J.; COX-1 inhibitors), including a prodrug Nepafenac®; immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Anticlotting agents such as heparin, antifibrinogen, fibrinolysin, anticlotting activase, etc., can also be delivered.

Antidiabetic agents that may be delivered using the present devices include acetohexamide, chlorpropamide, glipizide, glyburide, tolazamide, tolbutamide, insulin, aldose reductase inhibitors, etc. Some examples of anti-cancer agents include 5-fluorouracil, adriamycin, asparaginase, azacitidine, azathioprine, bleomycin, busulfan, carboplatin, carmustine, chlorambucil, cisplatin, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, fluoxymesterone, flutamide, goserelin, hydroxyurea, ifosfamide, leuprolide, levamisole, lomustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblastine, vincristine and vindesine.

Hormones, peptides, nucleic acids, saccharides, lipids, glycolipids, glycoproteins, and other macromolecules can be delivered using the present devices. Examples include: endocrine hormones such as pituitary, insulin, insulin-related growth factor, thyroid, growth hormones; heat shock proteins; immunological response modifiers such as muramyl dipeptide, cyclosporins, interferons (including α, β, and γ interferons), interleukin-2, cytokines, FK506 (an epoxy-pyrido-oxaazcyclotricosine-tetrone, also known as Tacrolimus), tumor necrosis factor, pentostatin, thymopentin, transforming factor beta2, erythropoetin; antineogenesis proteins (e.g., anit VEGF, Interfurons), among others and anticlotting agents including anticlotting activase. Further examples of macromolecules that can be delivered include monoclonal antibodies, brain nerve growth factor (BNGF), celiary nerve growth factor (CNGF), vascular endothelial growth factor (VEGF), and monoclonal antibodies directed against such growth factors. Additional examples of immunomodulators include tumor necrosis factor inhibitors such as thalidomide.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. The reference point used herein may be the operator such that the terms "proximal" and "distal" are in reference to an operator using the device. A region of the device that is closer to an operator may be described herein as "proximal" and a region of the device that is further away from an operator may be described herein as "distal". Similarly, the terms "proximal" and "distal" may also be used herein to refer to anatomical locations of a patient from the perspective of an operator or from the perspective of an entry point or along a path of insertion from the entry point of the system. As such, a location that is proximal may mean a location in the patient that is closer to an entry point of the device along a path of insertion towards a target and a location that is distal may mean a location in a patient that is further away from an entry point of the device along a path of insertion towards the target location. However, such terms are provided to establish relative frames of reference, and are not intended to limit the use or orientation of the devices to a specific configuration described in the various implementations.

As used herein, the term "about" means a range of values including the specified value, which a person of ordinary skill in the art would consider reasonably similar to the specified value. In aspects, about means within a standard deviation using measurements generally acceptable in the art. In aspects, about means a range extending to +/−10% of the specified value. In aspects, about includes the specified value.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

The systems disclosed herein may be packaged together in a single package. The finished package would be sterilized using sterilization methods such as Ethylene oxide or radiation and labeled and boxed. Instructions for use may also be provided in-box or through an internet link printed on the label.

The invention claimed is:

1. A system for ab interno insertion of an implant into an eye of a patient, the system comprising:
   an implant comprising a solid strip of a material having no internal lumen;
   a tissue cartridge comprising a nose cone fixedly coupled to a distal shaft comprising a lumen, the implant located within the lumen of the distal shaft, wherein at least a distal end region of the shaft is sized and shaped for insertion into an anterior chamber of the eye and atraumatic dissection of a cyclodialysis cleft between a sclera and a ciliary body of the eye; and
   a delivery device configured to reversibly couple with the tissue cartridge via a proximal end region of the nose cone for deployment of the implant from the lumen into the cyclodialysis cleft.

2. The system of claim 1, further comprising a cutting device, wherein the cutting device comprises a cutting member configured to cut a patch of the material into the implant.

3. The system of claim 2, wherein the delivery device comprises an actuator configured to deploy the implant through the lumen of the shaft into the eye.

4. The system of claim 1, wherein the shaft of the tissue cartridge is configured to deliver a viscous material.

5. A system for preparation of an implant from a patch of a material and ab interno insertion of the implant into an eye of a patient, the system comprising:
   a tissue cartridge comprising a nose cone fixedly coupled to a distal shaft defining a lumen between the nose cone and a distal end region of the distal shaft, at least the distal end region of the distal shaft being sized and shaped for insertion into an anterior chamber of the eye;
   a cutting device comprising a cutting member configured to cut the patch of the material into the implant; and
   a delivery device configured to reversibly couple to the tissue cartridge via a proximal end region of the nose cone of the tissue cartridge and deploy the implant from the lumen of the distal shaft.

6. The system of claim 5, wherein the cutting device comprises a base configured to receive the patch.

7. The system of claim 6, further comprising a compacting tool configured to urge the implant into the lumen of the distal shaft.

8. The system of claim 7, wherein the delivery device comprises an actuator configured to deploy the implant compacted within the lumen of the distal shaft into the eye.

9. A system for preparation of an implant and ab interno insertion of the implant into an eye of a patient, the system comprising:
   a tissue cartridge comprising:
      a nose cone comprising a proximal connector on a proximal end region and a distal end region; and
      a distal shaft fixedly coupled to the distal end region of the nose cone, the distal shaft defining a lumen from a proximal end region to a distal end region of the distal shaft, at least the distal end region of the distal shaft being sized and shaped for insertion into an anterior chamber of the eye; and
   a delivery device comprising a proximal handle having a distal end region defining a distal connector sized to engage and reversibly couple with the tissue cartridge via the proximal connector on the proximal end region of the nose cone.

10. The system of claim 9, further comprising a cutting device, wherein the cutting device comprises a cutting member configured to cut a patch of a material into the implant.

11. The system of claim 9, wherein the delivery device further comprises at least one actuator configured to deploy the implant, when positioned within the lumen of the distal shaft, out a distal opening and into the eye.

12. The system of claim 9, wherein the shaft of the tissue cartridge is configured to deliver a viscous material.

13. A method of preparing an implant for implantation into, and of inserting said implant into, an eye of a patient, the method comprising:
cutting a patch of a material with a cutting member of a cutting device to form an implant from the patch;
compacting the implant within a lumen of a shaft fixedly coupled to a distal end of a tissue cartridge;
coupling at least a portion of the tissue cartridge to a delivery device;
inserting a distal end region of the shaft into the anterior chamber of the eye;
positioning the distal end region adjacent eye tissue; and
actuating the delivery device to deploy the implant from the tissue cartridge through at least a portion of the lumen such that the implant engages the eye tissue.

14. The method of claim 13, further comprising delivering a viscous material through the shaft.

15. The system of claim 5, wherein a distal-most tip of the distal shaft is configured to dissect tissue for implantation into the Schlemm's canal or trans-sclerally.

16. The system of claim 8, further comprising a movable internal elongate member operatively coupled to the actuator to advance the implant through the lumen and out a distal opening of the distal shaft.

17. The system of claim 9, wherein the proximal connector and the distal connector comprises a male-to-female connection.

18. The system of claim 11, wherein the at least one actuator is configured to advance a tool from a first position at which the tool is retracted to a second position at which the tool inserts into the lumen behind the implant positioned within the lumen.

19. The system of claim 18, wherein the at least one actuator is configured to withdraw the nose cone relative to the tool to cause the implant to be deployed out the distal opening.

20. The system of claim 18, wherein the at least one actuator is configured to advance the tool relative to the nose cone to cause the implant to be deployed out the distal opening.

21. The system of claim 1, wherein the delivery device comprises a proximal handle comprising a distal receptacle sized and shaped to receive the proximal end region of the nose cone.

22. The system of claim 21, wherein the distal receptacle is keyed to receive the proximal end region in a first orientation and prevent the proximal end region from being received within the distal receptacle in another orientation that is different from the first orientation.

23. The system of claim 21, wherein actuation of an actuator on the proximal handle retracts the tissue cartridge proximally further into the distal receptacle to deploy the implant.

24. The system of claim 23, wherein the tissue cartridge retracts proximally relative to a stopper element positioned at least in part within the lumen of the distal shaft to deploy the implant through a distal opening of the distal shaft.

25. The system of claim 1, wherein the material comprises minimally-modified biologically-derived material.

26. The system of claim 25, wherein the biologically-derived material comprises scleral tissue.

* * * * *